(12) United States Patent
Yamasaki et al.

(10) Patent No.: US 6,869,950 B1
(45) Date of Patent: Mar. 22, 2005

(54) BENZIMIDAZOLE DERIVATIVES

(75) Inventors: Noritsugu Yamasaki, Himeji (JP); Takafumi Imoto, Arai (JP); Takahiro Hiramura, Tsukuba (JP); Miho Kawauchi, Tsukuba (JP); Teruo Oku, deceased, late of Takatsuki (JP); by Noriko Oku, legal representative, Takatsuki (JP); by Chikako Oku, legal representative, Takatsuki (JP); by Tomohito Oku, legal representative, Takatsuki (JP); Hiroshi Kayakiri, Suita (JP); Hitoshi Sawada, Tsukuba (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/869,101

(22) PCT Filed: Dec. 22, 1999

(86) PCT No.: PCT/JP99/07222

§ 371 (c)(1),
(2), (4) Date: Aug. 29, 2002

(87) PCT Pub. No.: WO00/39099

PCT Pub. Date: Jul. 6, 2000

(30) Foreign Application Priority Data

Dec. 24, 1998 (JP) ............................. 10/366870

(51) Int. Cl.$^7$ ............... A61K 31/4184; C07D 235/06
(52) U.S. Cl. ............ 514/234.5; 514/394; 544/139; 548/310.1; 548/304.4; 548/304.7
(58) Field of Search ............ 548/310.1, 304.4, 548/304.7; 544/139; 514/234.5, 394

(56) References Cited

U.S. PATENT DOCUMENTS 6,166,219 A * 12/2000 Yamasaki et al. ........ 548/309.4
6,348,032 B1 * 2/2002 Sperl et al. ................ 514/338
6,348,474 B1   2/2002 Kayakiri et al.
6,352,985 B1   3/2002 Yamasaki et al.
6,420,409 B1 * 7/2002 Yamasaki et al. ........... 514/394

FOREIGN PATENT DOCUMENTS

| EP | 0882718 A1 | 12/1998 |
| EP | 1020452 A1 | 7/2000 |
| EP | 1 132 087 A1 | 9/2001 |
| EP | 1 138 674 A1 | 10/2001 |
| WO | WO 097/24334 | 7/1997 |
| WO | WO-97/24334 * | 7/1997 |
| WO | WO 099/00373 | 1/1999 |
| WO | WO-99/00373 * | 1/1999 |

* cited by examiner

Primary Examiner—Laura L. Stockton
(74) Attorney, Agent, or Firm—Fish & Richardson, P.C.

(57) ABSTRACT

The present invention provides novel benzimidazole derivatives of the following formula (I) and salts thereof:

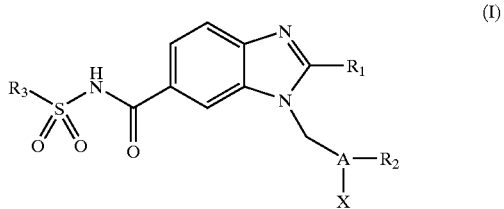

(I)

wherein $R_1$ represents a lower alkyl group or a lower alkyloxy-lower alkyl group; $R_2$ represents a hydrogen atom, a halogen atom, an alkyl group having 1 to 8 carbon atoms, an aryl group, and such; $R_3$ represents a lower alkyl group, a lower alkenyl group, an aryl group, a lower alkylaryl group, an aryl-lower alkenyl group, a halothienyl group, a lower alkylamino group, or an aryl-lower alkylamino group; A represents a benzene ring, a naphthalene ring, or a pyridine ring; and X represents a halogen atom. The derivatives and their salts have blood sugar level-depressing activity or PDE5-inhibiting activity, and are useful as pharmaceutical preparations.

6 Claims, 20 Drawing Sheets

(1)

(2)

(3)

(4)

(5)

(6)

(7)

(8)

(9)

(10)

(11)

(12)

(13)

(14)

(15)

(16)

(17)

(18)

(19)

(20)

(21)

(22)

(23)

(24)

(25)

(26)

(27)

(28)

(29)

(30)

(31)

(32)

(33)

(34)

(35)

(36)

(37)

(38)

(39)

(40)

(41)

(42)

(43)

(44)

(45)

(46)

(47)

(48)

(49)

(50)

(51)

(52)

(53)

(54)

(55)

(56)

(57)

(58)

(59)

(60)

(61)

(62)

(63)

(64)

(65)

(66)

(67)

(68)

(69)

(70)

(71)

(72)

(73)

(74)

(75)

(76)

(77)

(78)

(79)

(80)

(81)

(82)

(83)

(84)

(85)

(86)

(87)

(88)

(89)

(90)

(9 1)

(9 2)

(9 3)

(9 4)

(95)

(96)

(97)

BENZIMIDAZOLE DERIVATIVES

TECHNICAL FIELD

The present invention relates to novel benzimidazole derivatives, and, more specifically, to novel benzimidazole derivatives having blood sugar level-depressing activity or PDE5-inhibiting activity and their pharmaceutically acceptable salts. The present invention also relates to pharmaceutical compositions comprising, as an active ingredient, such benzimidazole derivatives or their pharmaceutically acceptable salts.

DISCLOSURE OF THE INVENTION

An objective of the present invention is to provide novel benzimidazole derivatives and their pharmaceutically acceptable salts, and also pharmaceutical compositions which comprise, as an active ingredient, such benzimidazole derivatives or their pharmaceutically acceptable salts and which can be used as preventive and therapeutic agents for impaired glucose tolerance, diabetes (type II diabetes), diabetic complications (e.g., diabetic gangrene, diabetic arthropathy, diabetic osteopenia, diabetic glomerulosclerosis, diabetic nephropathy, diabetic dermopathy, diabetic neuropathy, diabetic cataract, diabetic retinopathy, etc.), insulin-resistant syndrome (e.g., insulin receptor disorders, Rabson-Mendenhall syndrome, leprechaunism, Kobberling-Dunnigan syndrome, Seip syndrome, Lawrence syndrome, Cushing syndrome, acromegaly, etc.), polycystic ovary syndrome, hyperlipidemia, atherosclerosis, cardiovascular disorders (e.g., stenocardia, cardiac failure, etc.), hyperglycemia (e.g., abnormal saccharometabolism such as feeding disorders, etc.), pancreatitis, osteoporosis, hyperuricemia, hypertension, inflammatory bowel disease, skin disease accompanying abnormal differentation of epidermal cells, stenocardia, pulmonary hypertension, congestive heart failure, glomerulopathy (e.g., diabetic glomerulosclerosis, etc.), tubulointerstitial disorders (e.g., renopathy induced by FK506, cyclosporin, etc.), renal failure, atherosclerosis, angiostenosis (e.g., angiostenosis after percutaneous arterioplasty), distal angiopathy, cerebral apoplexy, chronic reversible obstructions (e.g., bronchitis, asthma (chronic asthma, allergic asthma), etc.), autoimmune disease, allergic rhinitis, urticaria, glaucoma, diseases characterized by enteromotility disorders (e.g., hypersensitive enteropathy syndrome, etc.), impotence (e.g., organic impotence, psychic impotence, etc.), nephritis, cachexia (e.g., progressive weight reduction due to lipolysis, myodegeneration, anaemia, edema, anorexia, and such in chronic diseases such as cancer, tuberculosis, endocrine diseases, and AIDS), pancreatitis, or post-PTCA restenosis.

The present inventors provide novel benzimidazole derivatives of the following formula (I) and their pharmaceutically acceptable salts, and further provide pharmaceutical compositions comprising such compounds or their pharmaceutically acceptable salts as an active ingredient and which can be used as preventive and therapeutic agents for impaired glucose tolerance, diabetes (type II diabetes), diabetic complications (e.g., diabetic gangrene, diabetic arthropathy, diabetic osteopenia, diabetic glomerulosclerosis, diabetic nephropathy, diabetic dermopathy, diabetic neuropathy, diabetic cataract, diabetic retinopathy, etc.), insulin-resistant syndrome (e.g., insulin receptor disorders, Rabson-Mendenhall syndrome, leprechaunism, Kobberling-Dunnigan syndrome, Seip syndrome, Lawrence syndrome, Cushing syndrome, acromegaly, etc.), polycystic ovary syndrome, hyperlipidemia, atherosclerosis, cardiovascular disorders (e.g., stenocardia, cardiac failure, etc.), hyperglycemia (e.g., abnormal saccharometabolism such as feeding disorders, etc.), pancreatitis, osteoporosis, hyperuricemia, hypertension, inflammatory bowel disease, skin disease accompanying abnormal differentation of epidermal cells, stenocardia, pulmonary hypertension, congestive heart failure, glomerulopathy (e.g., diabetic glomerulosclerosis, etc.), tubulointerstitial disorders (e.g., renopathy induced by FK506, cyclosporin, etc.), renal failure, atherosclerosis, angiostenosis (e.g., anglostenosis after percutaneous arterioplasty), distal angiopathy, cerebral apoplexy, chronic reversible obstructions (e.g., bronchitis, asthma (chronic asthma, allergic asthma), etc.), autoimmune disease, allergic rhinitis, urticaria, glaucoma, diseases characterized by enteromotility disorders (e.g., hypersensitive enteropathy syndrome, etc.), impotence (e.g., organic impotence, psychic impotence, etc.), nephritis, cachexia (e.g., progressive weight reduction due to lipolysis, myodegeneration, anaemia, edema, anorexia, and such in chronic diseases such as cancer, tuberculosis, endocrine diseases, and AIDS), pancreatitis, or post-PTCA restenosis.

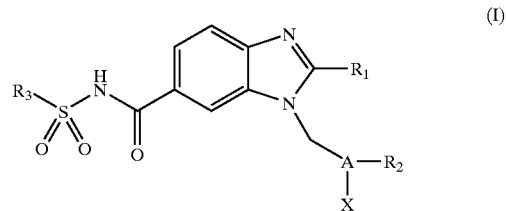

(I)

wherein $R_1$ represents a lower alkyl group or a lower alkyloxy-lower alkyl group; $R_2$ represents a hydrogen atom, a halogen atom, an alkyl group having 1 to 8 carbon atoms, an aryl group, an aryl-lower alkyl group, an aryloxy-lower alkyl group, an alkyloxy group having 1 to 8 carbon atoms, a lower alkyloxy-lower alkyloxy group, a lower cycloalkyl-lower alkyloxy group, an aryl-lower alkyloxy group, an alkynyl group having 3 to 8 carbon atoms, a halo-lower alkyl group, a lower alkylthio group, a lower alkanoylamino group, an N-substituted lower alkylamino group, a thienyl group, a furyl group, or a morpholino group; $R_3$ represents a lower alkyl group, a lower alkenyl group, an aryl group, a lower alkylaryl group, an aryl-lower alkenyl group, a halothienyl group, a lower alkylamino group, or an aryl-lower alkylamino group:

A represents a benzene ring, a naphthalene ring, or a pyridine ring; and

X represents a halogen atom.

In formula (I), A is preferably a benzene ring. The positions of the substituents on A are not specifically defined. Preferably, in the substituents mentioned above, a lower alkyl or a lower alkenyl moiety has 1 to 6 carbon atoms, a lower cycloalkyl moiety has 3 to 7 carbon atoms, and an aryl moiety is a phenyl group. More preferably, $R_1$ is a methyl group or a methyloxymethyl group; $R_2$ is a hydrogen atom, an alkyl group having 2 to 7 carbon atoms, a phenyl group, a phenylethyl group, a phenyloxymethyl group, an alkyloxy group having 1 to 8 carbon atoms, a (2-methyloxyethyl)oxy group, a cyclopentylmethyloxy group, a benzyloxy group, an alkynyl group having 5 to 7 carbon atoms, a trifluoromethyl group, a methylthio group, a butyrylamino group, an N-methylpentylamino group, a thienyl group, a furyl group, or a morpholino group; and $R_3$ is a butyl group, a pentyl group, a pentenyl group, a phenyl group, a methylphenyl group, a phenylethenyl group, a chlorothienyl group, an amino group substituted with an alkyl group having 2 to 6 carbon atoms, or a benzylamino group.

Benzimidazole derivatives to be provided by the present invention can be produced according to the following reaction formulae (a) to (m):

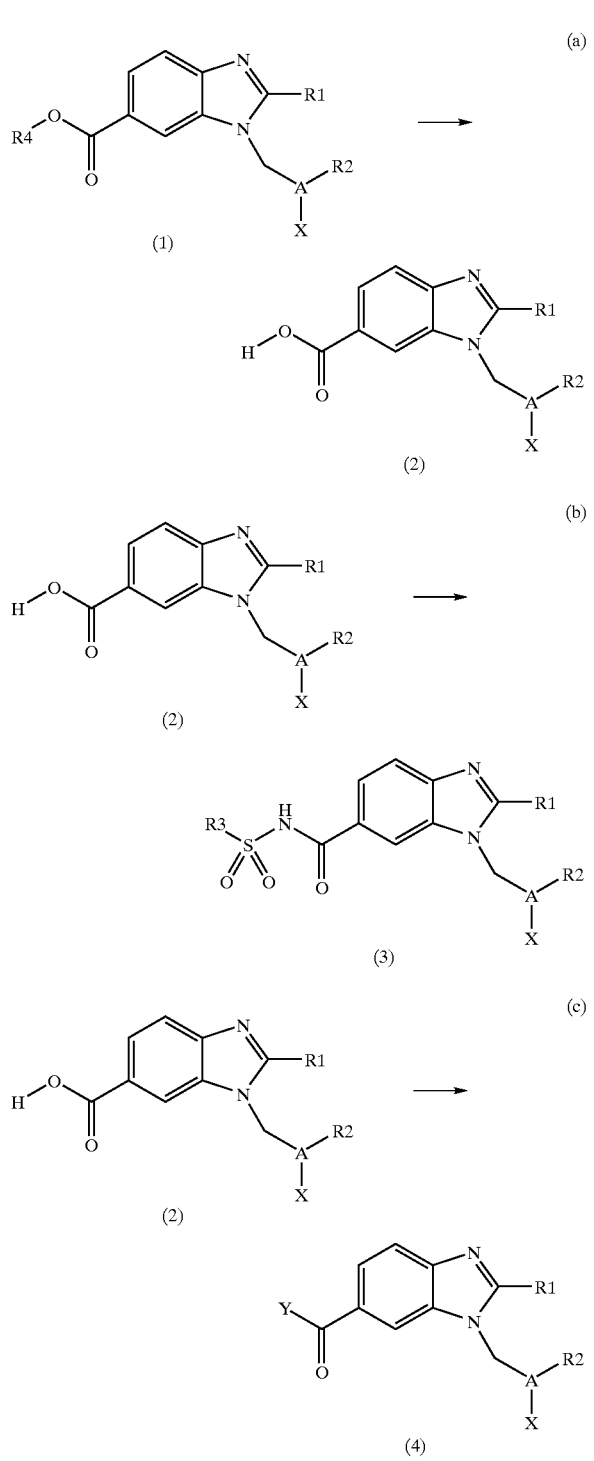

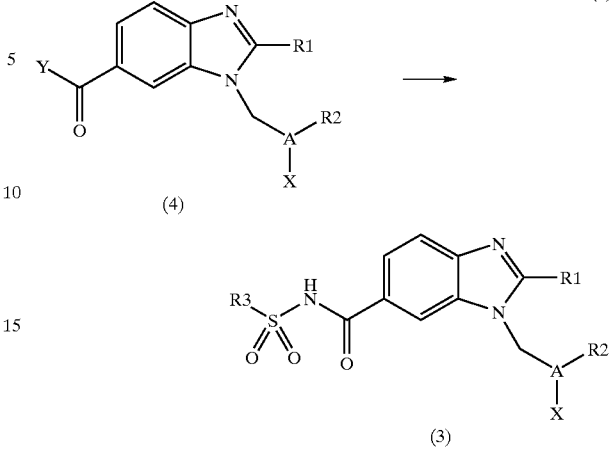

(In the reaction formulae (a) to (d), $R_1$, $R_2$, $R_3$, A, and X have the same meanings as those mentioned above, $R_4$ is a carboxy-protecting group, and Y is a halogen atom.)

In the compound of formula (1), $R_4$ is a carboxy-protecting group, such as an alkyl group, an aryl group, an arylmethyl group, and a trialkylsilyl group, as described in Theodora W. Greene, "Protective Groups In Organic Synthesis", pp. 187–192, John Wiley & Sons, Inc. The compound of formula (1) can be converted into the compound of formula (2) under deprotecting conditions described in the literature above. The most typical carboxy-protecting group is an alkyl group, and the compound of formula (1) can be hydrolyzed into the compound of formula (2) with a base such as lithium hydride, sodium hydroxide, potassium hydroxide, or the like (reaction formula (a)). The compound of formula (2) may be reacted with a carboxylic acid-activating agent, such as N,N'-carbonyldiimidazole 1-(3-dimethylaminopropyl)-3-ethylcarbodiimide or a salt thereof, dicyclohexylcarbodiimide, diisopropyl-carbodiimide, isobutyloxycarbonyl chloride, isobutyloyl chloride, pivaloyl chloride, isobutyl chloroformate, diphenylphosphorylazide, diethyl cyanophosphate, or the like, and then with corresponding sulfonamides or sulfamides in the presence of a base, such as diazabicycloundecene, triethylamine, 4-dimethylaminopyridine, N,N-dimethylaniline, pyridine, N-methylmorpholine, N-ethylpiperidine, potassium hydroxide, sodium hydroxide, potassium phosphate, potassium bicarbonate, potassium carbonate, sodium carbonate, sodium hydride, potassium t-butoxide, sodium ethoxide, or the like, to give the compound of formula (3) (reaction formula (b)). A compound obtained from the reaction of the compound of formula (2) and the carboxylic acid-activating agent may either be isolated or not. The compound of formula (3) can also be synthesized by reacting the compound obtained from the reaction of the compound of formula (2) and the carboxylic acid-activating agent with a salt of sulfonamides or a salt of sulfamides. The term "salt" as used herein refers to an inorganic salt such as a lithium salt, a sodium salt, a potassium salt, a calcium salt, a magnesium salt, a barium salt, or the like, or a salt with an organic base such as diazabicycloundecene, triethylamine, 4-dimethylaminopyridine, N,N-dimethylaniline, pyridine, N-methylmorpholine, N-ethylpiperidine, or the like.

The compound of formula (2) may be processed with thionyl chloride, thionyl bromide, phosphorus trichloride, phosphorus pentachloride, phosphorus oxychloride, oxalyl chloride, phosphorus tribromide, or the like to be converted into an acid halide of formula (4) or its salt (reaction formula (c)). The compound of formula (3) can be synthesized from the compound of formula (4) and sulfonamides or their salts or sulfamides or their salts in the presence or absense of a base.

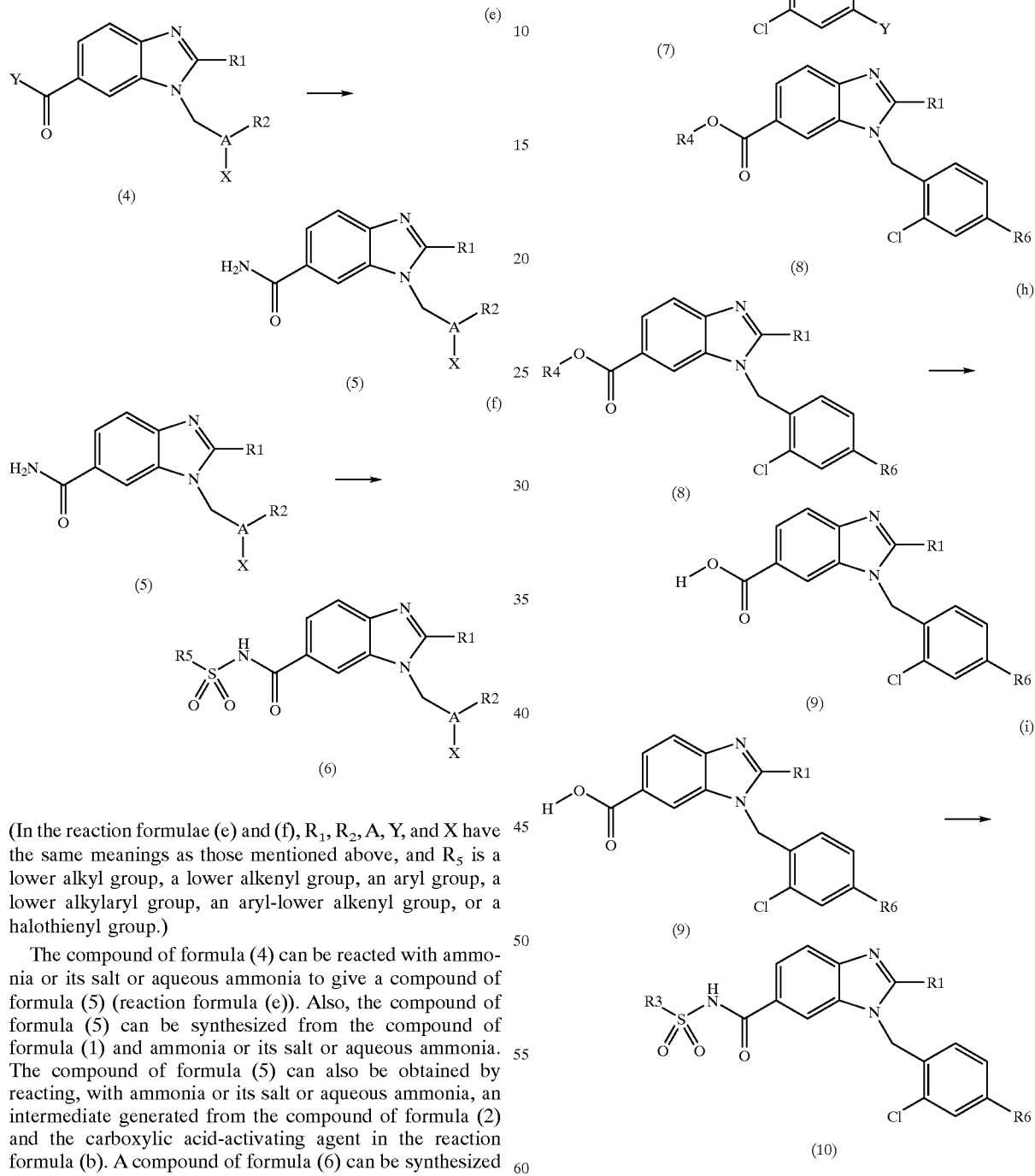

(In the reaction formulae (e) and (f), $R_1$, $R_2$, A, Y, and X have the same meanings as those mentioned above, and $R_5$ is a lower alkyl group, a lower alkenyl group, an aryl group, a lower alkylaryl group, an aryl-lower alkenyl group, or a halothienyl group.)

The compound of formula (4) can be reacted with ammonia or its salt or aqueous ammonia to give a compound of formula (5) (reaction formula (e)). Also, the compound of formula (5) can be synthesized from the compound of formula (1) and ammonia or its salt or aqueous ammonia. The compound of formula (5) can also be obtained by reacting, with ammonia or its salt or aqueous ammonia, an intermediate generated from the compound of formula (2) and the carboxylic acid-activating agent in the reaction formula (b). A compound of formula (6) can be synthesized from the compound of formula (5) and sulfonyl chlorides in the presence or absence of a base.

In the compounds of formulae (1) to (6), if $R_1$, $R_2$, $R_3$, or $R_5$ is substituted by one or more reactive substituents, the substituents can be changed during the steps of the reaction formulae (a) to (f) or in the final step. For example, methods of the reaction formulae (g) to (m) can be used.

(In the reactions formulae (g) to (i), R1, R3, R4, and Y have the same meanings as those mentioned above. R6 is an alkenyl group, an aryl-lower alkenyl group, an alkynyl group, an aryl group, a thienyl group, or a furyl group.)

As shown in the reaction formulae (g) to (i), a compound of formulae (7) can be reacted with an aryl borate, a thienyl borate, a furyl borate, an alkene, an arylalkene, or an alkyne in the presence of a palladium catalyst to give a compound of formula (8). The compound of formula (8) can be led to a compound of formula (10) by the methods of formulae (h) and (i) similar to those of formulae (a) and (b), respectively.

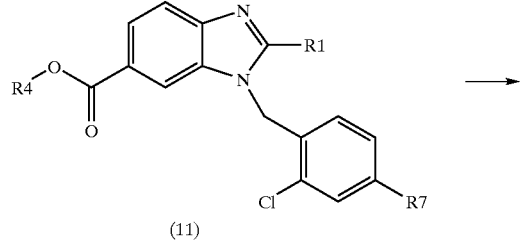
(j)

(11)

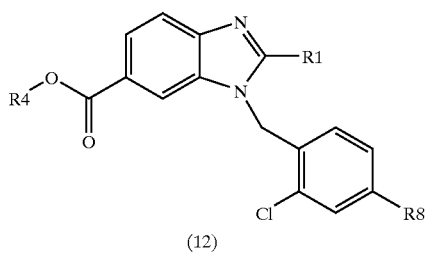

(12)

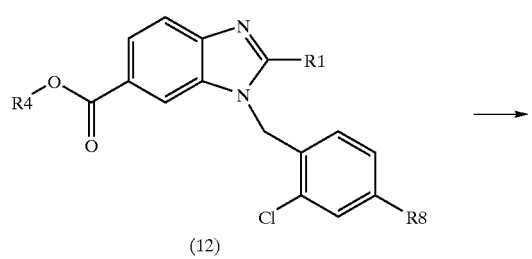

(12)

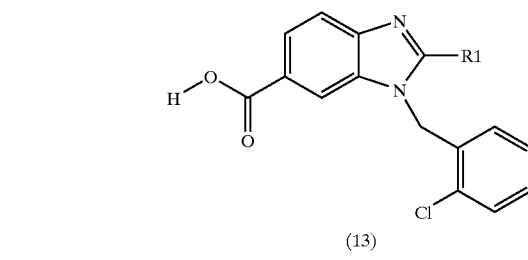

(13)

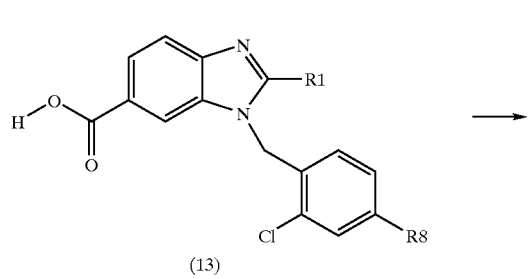

(13)

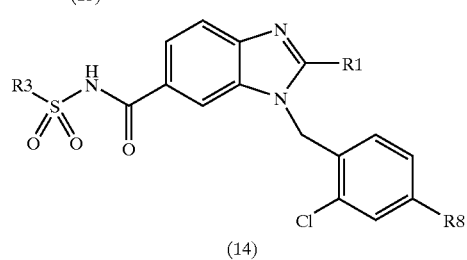

(14)

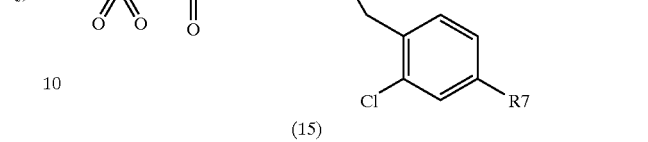
(m)

(15)

(14)

(In the reaction formulae (j) to (m), $R_1$, $R_3$, and $R_4$ have the same meanings as those mentioned above. $R_7$ is an alkenyl group, an aryl-lower alkenyl group, or an alkynyl group, and $R_8$ is an alkyl group or an arylalkyl group.)

As shown in the reaction formula (j), the compound of formula (11) can be reduced with a hydrogenation catalyst, such as platinum oxide, to give the compound of formula (12). The compound of formula (12) can be led to the compound of formula (14) by the methods of formulae (k) and (l) similar to those of formulae (a) and (b), respectively. The compound of formula (14) can also, be synthesized from the compound of formula (15) by the reduction with a hydrogenation catalyst typically such as platinum oxide (reaction formula (m)).

If desired, the intermediates formed in the above-mentioned steps may optionally be purified, prior to being subjected to the next step, through any conventional purification including, for example, recrystallization, column chromatography, thin-layer chromatography, high-performance liquid chromatography, and the like. If desired, the final products, i.e., the compounds of the present invention, may optionally be purified through any conventional purification, which includes, for example, recrystallization, column chromatography, thin-layer chromatography, high-performance liquid chromatography, and the like. Identification of compounds can be performed by NMR spectrometry, mass spectrometry, IR spectrometry, elementary analysis, measurement of melting point, and others.

Preferred embodiments and their details of various definitions as referred to herein to be within the scope of the present invention are described below.

A halogen atom includes a fluorine atom, a chlorine atom, a bromine atom, and an iodine atom. Preferred are a chlorine atom and a bromine atom.

Unless otherwise specifically indicated herein, the terminology "lower" indicates that the group has from 1 to 6 carbon atoms. As preferred examples of lower alkyl groups referred to herein, mentioned are linear and branched alkyl groups including a methyl group, an ethyl group, an n-propyl group, an i-propyl group, an n-butyl group, an i-butyl group, a sec-butyl group, a t-butyl group, an n-pentyl group, an i-pentyl group, a sec-pentyl group, a t-pentyl group, a 2-methylbutyl group, an n-hexyl group, a 1-methylpentyl group, a 2-methylpentyl group, a 3-methylpentyl group, a 4-methylpentyl group, a 1-ethylbutyl group, a 2-ethylbutyl group, a 1,1-dimethylbutyl group, a 2,2-dimethylbutyl group, a 3,3-dimethylbutyl group, a 1-ethyl-1-methyl propyl groups, etc. Preferred examples of lower alkyl groups include those having 1 to 3 carbon atoms.

Preferred examples of lower alkenyl groups include linear and branched lower alkenyl groups, for example, an ethenyl group, a 1-propenyl group, a 2-propenyl group, a 1-butenyl group, a 2-butenyl group, a 3-butenyl group, a 1,3-butadienyl group, a 1-pentenyl group, a 2-pentenyl group, a 3-pentenyl group, a 4-pentenyl group, a 1-hexenyl group, a 2-hexenyl group, a 3-hexenyl group, a 4-hexenyl group, a 5-hexenyl group, and a 1,4-methylpentenyl group.

An alkyl group having 1 to 8 carbon atoms that is linear or branched includes a methyl group, an ethyl group, an n-propyl group, an i-propyl group, an n-butyl group, an i-butyl group, a sec-butyl group, a t-butyl group, an n-pentyl group, an i-pentyl group, a sec-pentyl group, a t-pentyl group, a 2-methylbutyl group, an n-hexyl group, a 1-methylpentyl group, a 2-methylpentyl group, a 3-methylpentyl group, a 4-methylpentyl group, a 1-ethylbutyl group, a 2-ethylbutyl group, a 3-ethylbutyl group, a 1,1-dimethylbutyl group, a 2,2-dimethylbutyl group, a 3,3-dimethylbutyl group, a 1-ethyl-1-methylpropyl group, an n-heptyl group, a 1-methylhexyl group, a 2-methylhexyl group, a 3-methylhexyl group, a 4-methylhexyl group, a 5-methylhexyl group, a 1-ethylpentyl group, a 2-ethylpentyl group, a 3-ethylpentyl group, a 4-ethylpentyl group, a 1,1-dimethylpentyl group, a 2,2-dimethylpentyl group, a 3,3-dimethylpentyl group, a 4,4-dimethylpentyl group, a 1-propylbutyl group, an n-octyl group, a 1-methylheptyl group, a 6-methylheptyl group, a 1,1-dimethylhexyl group, a 2,2-dimethylhexyl group, a 5,5-dimethylhexyl group, a 2,3-dimethylhexyl group, a 3,5-dimethylhexyl group, etc.

An alkyloxy group having 1 to 8 carbon atoms includes, for example, a methoxy group, an ethoxy group, an n-propyloxy group, an i-propyloxy group, an n-butyloxy group, an i-butyloxy group, a sec-butyloxy group, a t-butyloxy group, an n-pentyloxy group, an i-pentyloxy group, a sec-pentyloxy group, a 2,2-dimethylpropyloxy group, a 2-methylbutoxy group, an n-hexyloxy group, an i-hexyloxy group, a t-hexyloxy group, a sec-hexyloxy group, a 2-methylpentyloxy group, a 3-methylpentyloxy group, a 1-ethylbutyloxy group, a 2-ethylbutyloxy group, a 1,1-dimethylbutyloxy group, a 2,2-dimethylbutyloxy group, a 3,3-dimethylbutyloxy group, a 1-ethyl-1-methylpropyloxy group, an n-heptyloxy group, a 1-methylhexyloxy group, a 1-ethylpentyloxy group, a 1,1-dimethylpentyloxy group, a 2,2-dimethylpentyloxy group, a 1-propylbutyloxy group, an n-octyloxy group, a 3-methylheptyloxy group, a 2-ethylhexyloxy group, a 2,2-dimethylhexyloxy group, a 3,3-dimethylhexyloxy group, a 1-propylpentyloxy group, etc.

A lower alkyloxy-lower alkyl group is an alkyloxy group, such as that mentioned herein above, having 1 to 6 carbon atoms, to which is bonded an lower alkyl group, such as that mentioned herein above, and includes, for example, a methyloxymethyl group, a 1-methyloxyethyl group, a 2-methyloxyethyl group, a 2-methyloxypropyl group, a 3-methyloxypropyl group, a 4-methyloxybutyl group, a 5-methyloxypentyl group, a 1-methyloxyhexyl group, a 2-methyloxyhexyl group, a 3-methyloxyhexyl group, a 4-methyloxyhexyl group, a 5-methyloxyhexyl group, a 6-methyloxyhexyl group, an ethyloxymethyl group, an n-propyloxymethyl group, an i-propyloxymethyl group, an n-butyloxymethyl group, a sec-butyloxymethyl group, a t-butyloxymethyl group, a 2-butyloxybutyl group, a 4-i-butyloxybutyl group, a 6-n-butyloxyhexyl group, a 3-methyloxy-2,2-dimethylpropyl group, etc.

A lower alkyloxy-lower alkyloxy group is a lower alkyloxy-lower alkyl group, such as that mentioned herein above, to which is bonded an oxygen atom, and includes, for example, a (methyloxymethyl)oxy group, a (1-methyloxyethyl)oxy group, a (2-methyloxyethyl)oxy group, a (2-methyloxypropyl)oxy group, a (3-methyloxypropyl)oxy group, a (4-methyloxybutyl)oxy group, a (5-methyloxypentyl)oxy group, a (1-methyloxyhexyl)oxy group, a (2-methyloxyhexyl)oxy group, a (3-methyloxyhexyl)oxy group, a (4-methyloxyhexyl)oxy group, a (5-methyloxyhexyl)oxy group, a (6-methyloxyhexyl)oxy group, an (ethyloxymethyl)oxy group, an (n-propyloxymethyl)oxy group, an (i-propyloxymethyl)oxy group, an (n-butyloxymethyl)oxy group, a (sec-butyloxymethyl)oxy group, a (t-butyloxymethyl)oxy group, a (2-butyloxybutyl)oxy group, a (4-i-butyloxybutyl)oxy group, a (6-n-butyloxyhexyl)oxy group, a (3-methyloxy-2,2-dimethylpropyl)oxy group, and so on.

A lower cycloalkyl-lower alkyloxy group is an alkyloxy group, such as that mentioned herein above, having 1 to 6 carbon atoms, to which is bonded a cycloalkyl group having 3 to 7 carbon atoms including, for example, a cyclopropyl group, a cyclobutyl group, a cyclopentyl group, a cyclohexyl group, a cycloheptyl group, etc., and includes a (cyclopropylmethyl)oxy group, a (2-cyclopropylethyl)oxy group, a (cyclobutylmethyl)oxy group, a (3-cyclobutylpropyl)oxy group, a (cyclopentylmethyl)oxy group, a (2-cyclopentylethyl)oxy group, a (4-cyclopentylbutyl)oxy group, a (cyclohexylmethyl)oxy group, a (1-cyclohexylethyl)oxy group, a (2-cyclohexylethyl)oxy group, a (3-cyclohexylpropyl)oxy group, a (2-cyclohexylpropyl)oxy group, a (1-cyclohexylpropyl)oxy group, a (4-cyclohexylbutyl)oxy group, a (3-cyclohexylbutyl)oxy group, a (2-cyclohexylbutyl)oxy group, a (6-cyclohexylhexyl)oxy group, a (1-cyclohexylbutyl)oxy group, cycloheptylmethyloxy group, etc.

An aryl group includes those having 6 to 10 carbon atoms, for example, a phenyl group, a naphthyl group, etc. The terminology "naphthyl" as referred to herein includes 1-naphthyl and 2-naphthyl.

An aryl-lower alkyl group is a lower alkyl group, such as that mentioned herein above, to which is bonded an aryl group, such as that mentioned herein above, and includes, for example, a benzyl group, a 1-phenylethyl group, a 2-phenylethyl group, a phenylpropyl group, a phenylbutyl group, a phenylpentyl group, a phenylhexyl group, a naphthylmethyl group, a naphthylethyl group, a naphthylpropyl group, a naphthylbutyl group, a naphthylpentyl group, a naphthylhexyl group, and so on.

An aryloxy-lower alkyl group is a lower alkyl group, such as that mentioned herein above, to which via an oxygen atom is bonded an aryl group, such as that mentioned herein above, and includes, for example, a (phenyloxy)methyl group, a (1-naphthyloxy)methyl group, a (2-naphthyloxy)methyl group, a 1-(phenyloxy)ethyl group, a 2-(phenyloxy)ethyl group, a 1-(1-naphthyloxy)ethyl group, a 1-(2-naphthyloxy)ethyl group, a 2-(1-naphthyloxy)ethyl group, a 2-(2-naphthyloxy)ethyl group, a 1-(phenyloxy)propyl group, a 2-(phenyloxy)propyl group, a 3-(phenyloxy)propyl group, a 1-(1-naphthyloxy)propyl group, a 1-(2- naphthyloxy)propyl group, a 2-(1-naphthyloxy)propyl group, a 2-(2-naphthyloxy)propyl group, a 3-(1-naphthyloxy)propyl group, a 3-(2-naphthyloxy)propyl group, a 4-(phenyloxy)butyl group, a 5-(phenyloxy)pentyl group, a 6-(phenyloxy)hexyl group, etc.

A aryl-lower alkyloxy group is an alkyloxy group, such as that mentioned herein above, having 1 to 6 carbon atoms, to which is bonded an aryl group such as that mentioned herein above, and includes, for example, a benzyloxy group, a 1-naphthylmethyloxy group, a 2-naphthylmethyloxy group, a (1-phenylethyl)oxy group, a (2-phenylethyl)oxy group, a (1-naphthylethan-1-yl)oxy group, a (2-naphthylethan-1-yl)oxy group, a (1-naphthylethan-2-yl)oxy group, a (2-naphthylethan-2-yl)oxy group, a (1-phenylpropyl)oxy group, a (2-phenylpropyl)oxy group, a (3-phenylpropyl)oxy group, a (1-naphthylpropan-1-yl)oxy group, a (2-naphthylpropan-1-yl)oxy group, a (1-naphthylpropan-2-yl)oxy group, a (2-naphthylpropan-2-yl)oxy group, a (1-naphthylpropan-3-yl)oxy group, a (2-naphthylpropan-3-yl)oxy group, a (4-phenylbutyl)oxy group, a (2-naphthylbutan-4-yl)oxy group, a (5-phenylpentyl)oxy group, a (2-naphthylpentan-5-yl)oxy group, a (6-phenylhexyl)oxy group, a (1-naphthylhexan-6-yl)oxy group, etc.

A lower alkylaryl group is an aryl group, such as that mentioned herein above, to which is bonded a lower alkyl group, such as that mentioned herein above, and includes, for example, a 2-methylphenyl group, a 3-methylphenyl group, a 4-methylphenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 2,3,5,6-tetramethylphenyl group, a pentamethylphenyl group, a 2-ethylphenyl group, a 3-ethylphenyl group, a 4-ethylphenyl group, a 2-n-propylphenyl group, a 2-i-propylphenyl group, a 3-n-propylphenyl group, a 3-i-propylphenyl group, a 4-n-propylphenyl group, a 4-i-propylphenyl group, a 2,4,6-tri-i-propylphenyl group, a 2-n-butylphenyl group, a 2-i-butylphenyl group, a 2-t-butylphenyl group, a 3-n-butylphenyl group, a 3-i-butylphenyl group, a 3-t-butylphenyl group, a 4-n-butylphenyl group, a 4-i-butylphenyl group, a 4-t-butylphenyl group, a 4-n-pentylphenyl group, a 4-i-pentylphenyl group, a 4-t-pentylphenyl group, a 4-n-hexylphenyl group, a 2-methylnaphthalen-1-yl group, a 3-methylnaphthalen-1-yl group, a 4-methylnaphthalen-1-yl group, a 5-methylnaphthalen-1-yl group, a 6-methylnaphthalen-1-yl group, a 7-methylnaphthalen-1-yl group, a 8-methylnaphthalen-1-yl group, a 1-methylnaphthalen-2-yl group, a 3-methylnaphthalen-2-yl group, a 4-methylnaphthalen-2-yl group, a 5-methylnaphthalen-2-yl group, a 6-methylnaphthalen-2-yl group, a 7-methylnaphthalen-2-yl group, a 8-methylnaphthalen-2-yl group, a 5,8-dimethylnaphthalen-1-yl group, a 5,8-dimethylnaphthalen-2-yl group, etc.

An aryl-lower alkenyl group is a lower alkenyl group, such as that mentioned herein above, to which is bonded an aryl group, such as that mentioned herein above, and includes, for example, a 1-phenylethenyl group, a 2-phenylethenyl group, a 1-phenyl-1-propenyl group, a 2-phenyl-1-propenyl group, a 3-phenyl-1-propenyl group, a 1-phenyl-2-propenyl group, a 2-phenyl-2-propenyl group, a 3-phenyl-2-propenyl group, a 1-phenyl-1-butenyl group, a 2-phenyl-1-butenyl group, a 4-phenyl-2-butenyl group, a 3-phenyl-2-propenyl group, a 2-phenyl-1-pentenyl group, a 2-phenyl-3-pentenyl group, a 2-phenyl-1-pentenyl group, a 2-phenyl-1-hexenyl group, etc.

An alkynyl group, having 3 to 8 carbon atoms includes a 1-propyn-1-yl group, a 2-propyn-1-yl group, a 1-butyn-1-yl group, a 2-butyn-1-yl group, a 3-butyn-1-yl group, a 3-butyn-2-yl group, a 1-pentyn-1-yl group, a 2-pentyn-1-yl group, a 4-pentyn-1-yl group, a 3-pentyn-2-yl group, a 1-hexyn-1-yl group, a 3-hexyn-1-yl group, a 5-hexyn-1-yl group, a 1-hexyn-3-yl group, a 2-hexyn-4-yl group, a 1-heptyn-1-yl group, a 1-octyn-1-yl group, a 3-methyl-1-pentyn-1-yl group, a 4-methyl-1-methyl-1-pentyn-1-yl group, etc.

A halo-lower alkyl group is a lower alkyl group, such as that mentioned herein above, which is substituted with one or more halogen atoms, such as that mentioned herein above, and includes a fluoromethyl group, a difluoromethyl group, a trifluoromethyl group, a chloromethyl group, a dichloromethyl group, a trichloromethyl group, a bromomethyl group, a dibromomethyl group, a tribromomethyl group, an iodomethyl group, a 1-fluoroethyl group, a 1-chloromethyl group, a 1-bromomethyl group, a 2-fluoroethyl group, a 2-chloromethyl group, a 2-bromomethyl group, a 1,1-difluoroethyl group, a 1,1-dichloroethyl group, a 1,1-dibromoethyl group, a 2,2-difluoroethyl group, a 2,2-dichloroethyl group, a 2,2-dibromoethyl group, a 1,2-difluoroethyl group, a 1,2-dichloroethyl group, a 1,2-dibromoethyl group, a 2,2,2-trifluoroethyl group, a heptafluoroethyl group, a 1-fluoropropyl group, a 1-chloropropyl group, a 1-bromopropyl group, a 2-fluoropropyl group, a 2-chloropropyl group, a 2-bromopropyl group, a 3-fluoropropyl group, a 3-chloropropyl group, a 3-bromopropyl group, a 1,1-difluoropropyl group, a 1,1-dichloropropyl group, a 1,1-dibromopropyl group, a 1,2-difluoropropyl group, a 1,2-dichloropropyl group, a 1,2-dibromopropyl group, a 2,3-difluoropropyl group, a 2,3-dichloropropyl group, a 2,3-dibromopropyl group, a 3,3,3-trifluoropropyl group, a 2,2,3,3,3-pentafluoropropyl group, a 2-fluorobutyl group, a 2-chlorobutyl group, a 2-bromobutyl group, a 4-fluorobutyl group, a 4-chlorobutyl group, a 4-bromobutyl group, a 4-iodobutyl group, a 3,4-dichlorobutyl group, a 2,4-dibromopentyl group, a 4,4,4-pentafluorobutyl group, a 2,2,3,3,4,4,4-heptafluorobutyl group, a perfluorobutyl group, a 2-fluoropentyl group, a 2-chloropentyl group, a 2-bromopentyl group, a 5-fluoropentyl group, a 5-chloropentyl group, a 3-iodopentyl group, a 5-bromopentyl group, a 2-fluorohexyl group, a 2-chlorohexyl group, a 2-bromohexyl group, a 6-fluorohexyl group, a 6-chlorohexyl group, a 6-bromohexyl group, a 1,3,5-trifluorohexyl group, a perfluorohexyl group, etc.

A lower alkylthio group is a linear or branched alkylthio group having up to 6 carbon atoms. This includes, for example, a methylthio group, an ethylthio group, an n-propylthio group, an i-propylthio group, an n-butylthio group, an i-butylthio group, a sec-butylthio group, a t-butylthio group, an n-pentylthio group, an i-pentylthio group, a sec-pentylthio group, a t-dimethylpropylthio group, a 2-methylbutylthio group, an n-hexylthio group, an i-hexylthio group, a t-hexylthio group, a sec-hexylthio groups a 2-methylpentylthio group, a 3-methylpentylthio group, a 1-ethylbutylthio group, a 2-ethylbutylthio group, a 1,1-dimethylbutylthio group, a 2,2-dimethylbutylthio group, a 3,3-dimethylbutylthio group, a 1-ethyl-1-methylpropylthio group, etc.

A lower alkylamino group is a lower alkyl group, such as that mentioned hereinabove, to which is bonded an amino group, and includes, for example, a methylamino group, an ethylamino group, an n-propylamino group, an i-propylamino group, an n-butylamino group, an i-butylamino group, a sec-butylamino group, a t-butylamino group, an n-pentylamino group, an i-pentylamino group, a sec-pentylamino group, a t-pentylamino group, a 2-methylbutylamino group, an n-hexylamino group, a 1-methylpentylamino group, a 2-methylpentylamino group, a 3-methylpentylamino group, a 4-methylpentylamino group, a 1-ethylbutylamino group, a 2-ethylbutylamino group, a 3-ethylbutylamino group, a 1,1-dimethylbutylamino group, a 2,2-dimethylbutylamino group, a 3,3-dimethylbutylamino group, a 1-ethyl-1-methylpropylamino group, etc.

A lower alkanoylamino group is an amino group to which is bonded a lower alkanoyl group. The lower alkanoyl group includes, for example, a methylcarbonyl group, an ethylcarbonyl group, an n-propylcarbonyl group, an i-propylcarbonyl group, an n-butylcarbonyl group, an i-butylcarbonyl group, a sec-butylcarbonyl group, a t-butylcarbonyl group, an n-pentylcarbonyl group, an i-pentylcarbonyl group, a sec-pentylcarbonyl group, a t-pentylcarbonyl group, a 2-methylbutylcarbonyl group, an n-hexylcarbonyl group, an i-hexylcarbonyl group, a t-hexylcarbonyl group, a sec-hexylcarbonyl group, a 2-methylpentylcarbonyl group, a 3-methylpentylcarbonyl group, a 1-ethylbutylcarbonyl group, a 2-ethylbutylcarbonyl group, an 1,1-dimethylbutylcarbonyl group, a 2,2-dimethylbutylcarbonyl group, a 3,3-dimethylbutylcarbonyl group, a 1-ethyl-1-methylpropylcarbonyl group, etc.

An N-substituted lower alkylamino group is a lower alkylamino group, such as that mentioned herein above, in which the nitrogen atom is substituted with, for example, a lower alkyl group, such as that mentioned herein above or a lower alkanoyl group, such as that mentioned herein above.

An aryl-lower alkylamino group is an amino group to which is bonded an aryl-lower alkyl group, such as that mentioned herein above, and includes, for example, a benzylamino group, a 1-naphthylmethylamino group, a 2-naphthylmethylamino group, a (1-phenylethyl)amino group, a (2-phenylethyl)amino group, a (1-naphthylethan-1-yl)amino group, a (2-naphthylethan-1-yl)amino group, a (1-naphthylethan-2-yl)amino group, a (2-naphthylethan-2-yl)amino group, a (1-phenylpropyl)amino group, a (2-phenylpropyl)amino group, a (3-phenylpropyl)amino group, a (1-naphthylpropan-1-yl)amino group, a (2-naphthylpropan-1-yl)amino group, a (1-naphthylpropan-2-yl)amino group, a (2-naphthylpropan-2-yl)amino group, a (1-naphthylpropan-3-yl)amino group, a (2-naphthylpropan-3-yl)amino group, a (4-phenylbutyl)amino group, a (2-naphthylbutan-4-yl)amino group, a (5-phenylpentyl)amino group, a (2-naphthylpentan-5-yl)amino group, a (6-phenylhexyl)amino group, a (1-naphthylhexan-6-yl)amino group, etc.

A halothienyl group is a thienyl group substituted with a halogen atom, including a fluorothienyl group, a chlorothienyl group, a bromothienyl group, etc., and a chlorothlenyl group is preferred.

Preferred salts of the benzimidazole derivatives of the present invention are non-toxic, ordinary pharmaceutically acceptable salts thereof. For example, mentioned are salts of the derivatives with bases or acid-addition salts of the derivatives, which include, for example, salts thereof with inorganic bases, such as salts with alkali metals (e.g., sodium, potassium, etc.), salts with alkaline earth metals (e.g., calcium, magnesium, etc.), ammonium salts, etc.; salts with organic amines (e.g., triethylamine, pyridine, picoline, ethanolamine, triethanolamine, dicyclohexylamine, N,N'-dibenzylethylenediamine, etc.); salts with inorganic acids (e.g., hydrochloric acid, hydrobromic acid, sulfuric acid, phosphoric acid, etc.); salts with organic carboxylic acids (e.g., formic acid, acetic acid, trifluoroacetic acid, maleic acid, tartaric acid, etc.); salts with sulfonic acids (e.g., methanesulfonic acid, benzenesulfonic acid, p-toluenesulfonic acid, etc.); salts with basic or acidic amino acids (e.g., arginine, aspartic acid, glutamic acid, etc.), etc.

The compounds of the invention can contain one or more chiral centers, and therefore can be enantiomers or blastereomers. Few of the compounds containing alkenyl group can also be cis- or trans-lsomers. In both cases, the mixture of such isomers and each of them are within the scope of this invention.

The compounds of the invention can also exist as tautomers, and individual of such tautmers and the mixture thereof are within the scope of this invention.

The compounds of the invention and their salts can be solvates, which are also within the invention. The solvent for the solvates is preferably water or ethanol.

Specific examples of the compounds of the present invention include 1-(2,4-dichlorobenzyl)-2-methyl-6-((3-methylbenzene)sulfonylcarbamoyl)benzimidazole, 1-((1-bromonaphthalen-2-yl)methyl)-2-methyl-6-((4-methylbenzene)sulfonylcarbamoyl)benzimidazole, 6-(1-butanesulfonylcarbamoyl)-1-(4-bromo-2-chlorobenzyl)-2-methylbenzimidazole, 1-(4-bromo-2-chlorobenzyl)-2-methyl-6-((3-methylbenzene)sulfonylcarbamoyl) benzimidazole, 6-(1-butanesulfonylcarbamoyl)-1-(2-chloro-4-phenylbenzyl)-2-methylbenzimidazole, 1-(2-chloro-4-(2-phenylethyl)benzyl)-2-methyl-6-((4-methylbenzene) sulfonylcarbamoyl)benzimidazole, 1-(2-chloro-4-(phenyloxymethyl)benzyl)-2-methyl-6-((E)-(1-pent-1-ene) sulfonylcarbamoyl)benzimidazole, 1-(2-chloro-4-(phenyloxymethyl)benzyl)-2-methyl-6-((E)-(2-phenylethene)sulfonylcarbamoyl)benzimidazole, 6-(1-butanesulfonylcarbamoyl)-1-(2-chloro-4-(phenyloxymethyl)benzyl)-2-methylbenzimidazole, 1-(2-chloro-4-(phenyloxymethyl)benzyl)-2-methyl-6-((3-methylbenzene)sulfonylcarbamoyl)benzimidazole, 1-(2-chloro-4-(n-octyloxy)benzyl)-2-methyl-6-(1-pentanesulfonylcarbamoyl)benzimidazole, 1-(2-chloro-4-(n-octyloxy)benzyl)-2-methyl-6-((4-methylbenzene) sulfonylcarbamoyl)benzimidadzole, 1-(2-chloro-4-(n-hexyloxy)benzyl)-2-methyl-6-(1-pentanesulfonylcarbamoyl)benzimidazole, 1-(2-chloro-4-(n-pentyloxy)benzyl)-2-methyl-6-(1-pentanesulfonylcarbamoyl)benzimidazole, 1-(2-chloro-4-(n-pentyloxy)benzyl)-2-methyl-6-((4-methylbenzene) sulfonylcarbamoyl)benzimidazole, 1-(4-n-butyloxy-2-chlorobenzyl)-2-methyl-6-((4-methylbenzene) sulfonylcarbamoyl)benzimidazole, 1-(2-chloro-4-(n-propyloxy)benzyl)-2-methyl-6-(1-pentanesulfonylcarbamoyl)benzimidazole, 1-(2-chloro-4-(n-propyloxy)benzyl)-2-methyl-6-((4-methylbenzene) sulfonylcarbamoyl)benzimidazole, 1-(2-chloro-4-(methyloxy)benzyl)-2-methyl-6-(1-pentanesulfonylcarbamoyl)benzimidazole, 1-(2-chloro-4-(methyloxy)benzyl)-2-methyl-6-((4-methylbenzene) sulfonylcarbamoyl)benzimidazole, 1-(2-chloro-4-((2-methyloxyethyl)oxy)benzyl)-2-methyl-6-(1-pentanesulfonylcarbamoyl)benzimidazole, 1-(2-chloro-4-((2-methyloxyethyl)oxy)benzyl)-2-methyl-6-((4-methylbenzene)sulfonylcarbamoyl)benzimidazole, 1-(2-chloro-4-(cyclopentylmethyloxy)benzyl)-2-methyl-6-(1-pentanesulfonylcarbamoyl)benzimidazole, 1-(2-chloro-4-(cyclopentylmethyloxy)benzyl)-2-methyl-6-((4-methylbenzene)sulfonylcarbamoyl)benzimidazole, 1-(2-chloro-4-(cyclopentylmethyloxy)benzyl)-2-methyl-6-((E)-

1-pent-1-enesulfonylcarbamoyl)benzimidazole, 6-(benzenesulfonylcarbamoyl)-1-(4-benzyloxy-2-chlorobenzyl)-2-methylbenzimidazole, 1-(4-benzyloxy-2-chlorobenzyl)-2-methyl-6-((3-methylbenzene)sulfonylcarbamoyl)benzimidazole, 1-(4-benzyloxy-2-chlorobenzyl)-2-methyl-6-((E)-(2-phenylethene)sulfonylcarbamoyl)benzimidazole, 1-(4-benzyloxy-2-chlorobenzyl)-2-methyl-6-((5-chloro-2-thiophene)sulfonylcarbamoyl)benzimidazole, 1-(4-benzyloxy-2-chlorobenzyl)-6-(1-butanesulfonylcarbamoyl)-2-methylbenzimidazole, 1-(4-benzyloxy-2-chlorobenzyl)-2-methyl-6-((E)-1-pent-1-enesulfonylcarbamoyl)benzimidazole, 6-(1-butanesulfonylcarbamoyl)-1-(2-chloro-4-(2-thienyl)benzyl)-2-methylbenzimidazole, 1-(2-chloro-4-(2-thienyl)benzyl)-2-methyl-6-((E)-1-pent-1-enesulfonylcarbamoyl)benzimidazole, 6-(benzenesulfonylcarbamoyl)-1-(2-chloro-4-(2-furyl)benzyl)-2-methylbenzimidazole, 1-(2-chloro-4-(2-furyl)benzyl)-2-methyl-6-((3-methylbenzene)sulfonylcarbamoyl)benzimidazole, 1-(2-chloro-4-(2-furyl)benzyl)-2-methyl-6-((E)-(2-phenylethene)sulfonylcarbamoyl)benzimidazole, 1-(2-chloro-4-(2-furyl)benzyl)-6-((5-chloro-2-thiophene)sulfonylcarbamoyl)-2-methylbenzimidazole, 6-(1-butanesulfonylcarbamoyl)-1-(2-chloro-4-(2-furyl)benzyl)-2-methylbenzimidazole, 1-(2-chloro-4-(2-furyl)benzyl)-2-methyl-6-((E)-1-pent-1-enesulfonylcarbamoyl)benzimidazole, 1-(2-chloro-4-phenylbenzyl)-2-(methyloxymethyl)-6-(1-pentanesulfonylcarbamoyl)benzimidazole, 1-(2-chloro-4-phenylbenzyl)-6-((4-methylbenzene)sulfonylcarbamoyl)-2-(methyloxymethyl)benzimidazole, 1-(2-chloro-4-(1-pentyn-1-yl)benzyl)-2-methyl-6-(1-pentanesulfonylcarbamoyl)benzimidazole, 1-(2-chloro-4-(1-pentyn-1-yl)benzyl)-2-methyl-6-((4-methylbenzene)sulfonylcarbamoyl)benzimidazole, 1-(2-chloro-4-(1-hexyn-1-yl)benzyl)-2-methyl-6-(1-pentanesulfonylcarbamoyl)benzimidazole, 1-(2-chloro-4-(1-hexyn-1-yl)benzyl)-2-methyl-6-((4-methylbenzene)sulfonylcarbamoyl)benzimidazole, 1-(2-chloro-4-(1-heptyn-1-yl)benzyl)-2-methyl-6-(1-pentanesulfonylcarbamoyl)benzimidazole, 1-(2-chloro-4-(1-heptyn-1-yl)benzyl)-2-methyl-6-((4-methylbenzene)sulfonylcarbamoyl)benzimidazole, 1-(2-chloro-4-ethylbenzyl)-2-methyl-6-(1-pentanesulfonylcarbamoyl)benzimidazole, 1-(2-chloro-4-ethylbenzyl)-2-methyl-6-((4-methylbenzene)sulfonylcarbamoyl)benzimidazole, 1-(4-n-butyl-2-chlorobenzyl)-2-methyl-6-(1-pentanesulfonylcarbamoyl)benzimidazole, 1-(4-n-butyl-2-chlorobenzyl)-2-methyl-6-((4-methylbenzene)sulfonylcarbamoyl)benzimidazole, 1-(2-chloro-4-(1-pentyl)benzyl)-2-methyl-6-(1-pentanesulfonylcarbamoyl)benzimidazole, 1-(2-chloro-4-(1-pentyl)benzyl)-2-methyl-6-((4-methylbenzene)sulfonylcarbamoyl)benzimidazole, 6-(1-butanesulfonylcarbamoyl)-1-(2-chloro-4-(1-hexyl)benzyl)-2-methylbenzimidazole, 1-(2-chloro-4-(1-hexyl)benzyl)-2-methyl-6-(1-pentanesulfonylcarbamoyl)benzimidazole, 1-(2-chloro-4-(1-hexyl)benzyl)-2-methyl-6-((E)-1-pent-1-enesulfonylcarbamoyl)benzimidazole, 1-(2-chloro-4-(1-hexyl)benzyl)-2-methyl-6-((E)-(2-phenylethene)sulfonylcarbamoyl)benzimidazole, 1-(2-chloro-4-(1-hexyl)benzyl)-2-methyl-6-((5-chloro-2-thiophene)sulfonylcarbamoyl)benzimidazole, 1-(2-chloro-4-(1-heptyl)benzyl)-2-methyl-6-(1-pentanesulfonylcarbamoyl)benzimidazole, 1-(2-chloro6-4-(1-heptyl)benzyl)-2-methyl-6-((4-methylbenzene)sulfonylcarbamoyl)benzimidazole, 6-(1-butanesulfonylcarbamoyl)-1-(2-chloro-4-(trifluoromethyl)benzyl)-2-methylbenzimidazole, 6-(benzenesulfonylcarbamoyl)-1-(2-chloro-4-(trifluoromethyl)benzyl)-2-methylbenzimidazole, 1-(2-chloro-4-(trifluoromethyl)benzyl)-2-methyl-6-((3-methylbenzene)sulfonylcarbamoyl)benzimidazole, 1-(2-chloro-4-(trifluoromethyl)benzyl)-2-methyl-6-((E)-(2-phenylethene)sulfonylcarbamoyl)benzimidazole, 1-(2-chloro-4-(trifluoromethyl)benzyl)-2-methyl-6-((5-chloro-2-thiophene)sulfonylcarbamoyl)benzimidazole, 1-(2-chloro-4-(N-methyl-N-(1-pentyl)amino)benzyl)-2-methyl-6-(1-pentanesulfonylcarbamoyl)benzimidazole, 1-(2-chloro-4-(N-methyl-N-(1-pentyl)amino)benzyl)-2-methyl-6-((4-methylbenzene)sulfonylcarbamoyl)benzimidazole, 1-(4-(N-1-butyrylamino)-2-chlorobenzyl)-2-methyl-6-(1-pentanesulfonylcarbamoyl)benzimidazole, 1-(4-(N-1-butyrylamino)-2-chlorobenzyl)-2-methyl-6-((4-methylbenzene)sulfonylcarbamoyl)benzimidazole, 1-(2-chloro-4-morpholinobenzyl)-2-methyl-6-((4-methylbenzene)sulfonylcarbamoyl)benzimidazole, 1-(2-chloro-4-morpholinobenzyl)-2-methyl-6-(1-pentanesulfonylcarbamoyl)benzimidazole, 1-(2-chloro-4-(methylthio)benzyl)-2-methyl-6-(1-pentanesulfonylcarbamoyl)benzimidazole, 1-(2-chloro-4-(methylthio)benzyl)-2-methyl-6-((4-methylbenzene)sulfonylcarbamoyl)benzimidazole, 1-(2-chloro-4-(trifluoromethyl)benzyl)-2-methyl-6-((N-1-propylaminosulfonyl)carbamoyl)benzimidazole, 1-(2-chloro-4-phenylbenzyl)-2-methyl-6-((N-1-propylaminosulfonyl)carbamoyl)benzimidazole, 6-((N-1-butylaminosulfonyl)carbamoyl)-1-(2-chloro-4-phenylbenzyl)-2-methylbenzimidazole, 1-(2-chloro-4-phenylbenzyl)-6-((N-1-hexylaminosulfonyl)carbamoyl)-2-methylbenzimidazole, 6-((benzylaminosulfonyl)carbamoyl)-1-(2-chloro-4-phenylbenzyl)-2-methylbenzimidazole, 1-(4-bromo-2-chlorobenzyl)-6-((N-ethylaminosulfonyl)carbamoyl)-2-methylbenzimidazole, 1-(4-bromo-2-chlorobenzyl)-2-methyl-6-((N-1-propylaminosulfonyl)carbamoyl)benzimidazole, 1-(4-bromo-2-chlorobenzyl)-2-methyl-6-((N-1-butylaminosulfonyl)carbamoyl)-2-methylbenzimidazole, 1-(4-bromo-2-chlorobenzyl)-2-methyl-6-((N-1-pentylaminosulfonyl)carbamoyl)benzimidazole, 6-((benzylaminosulfonyl)carbamoyl)-1-(4-bromo-2-chlorobenzyl)-2-methylbenzimidazole, 6-((N-1-butylaminosulfonyl)carbamoyl)-1-(2-chloro-4-(methyloxy)benzyl)-2-methylbenzimidazole, 1-(2-chloro-4-(ethyloxy)benzyl)-6-((N-ethylaminosulfonyl)carbamoyl)-2-methylbenzimidazole, 1-(2-chloro-4-(ethyloxy)benzyl)-2-methyl-6-((N-1-propylaminosulfonyl)carbamoyl)benzimidazole, 6-((N-1-butylaminosulfonyl)carbamoyl)-1-(2-chloro-4-(ethyloxy)benzyl)-2-methylbenzimidazole, 1-(2-chloro-4-(pentyloxy)benzyl)-6-((N-ethylaminosulfonyl)carbamoyl)-2-methylbenzimidazole, 1-(2-chloro-4-(pentyloxy)benzyl)-2-methyl-6-((N-1-propylaminosulfonyl)carbamoyl)benzimidazole, 6-((N-1-butylaminosulfonyl)carbamoyl)-1-(2-chloro-4-(pentyloxy)benzyl)-2-methylbenzimidazole, 1-(2-chloro-4-(2-furyl)benzyl)-6-((N-ethylaminosulfonyl)carbamoyl)-2-methylbenzimidazole, 1-(2-chloro-4-(2-furyl)benzyl)-2-methyl-6-((N-1-propylaminosulfonyl)carbamoyl)benzimidazole, 6-((N-1-butylaminosulfonyl)carbamoyl)-1-(2-chloro-4-(2-furyl)benzyl)-2-methylbenzimidazole, 6-((benzylaminosulfonyl)carbamoyl)-1(2-chloro-4-(2-furyl)benzyl)-2-methylbenzimidazole, 1-(2-chloro-4-ethylbenzyl)-2-methyl-6-((N-1-propylaminosulfonyl)carbamoyl)benzimidazole, 6-((N-1-butylaminosulfonyl)carbamoyl)-1-(2-chloro-4-ethylbenzyl)-2-methylbenzimidazole, 6-((N-1-butylaminosulfonyl)

carbamoyl)-1-(2-chloro-4-n-hexylbenzyl)-2-methylbenzimidazole, etc.

The benzimidazole derivatives and their pharmaceutically acceptable salts of the present invention that are mentioned herein above, based on their blood sugar level-depressing activity, are effective for preventing and treating various disorders, such as impaired glucose tolerance, diabetes (type II diabetes), diabetic complications (e.g., diabetic nephropathy, diabetic neuropathy, diabetic retinopathy, etc.), insulin-resistant syndrome (e.g., insulin receptor disorders, Rabson-Mendenhall syndrome, leprechaunism, Kobberling-Dunnigan syndrome, Seip syndrome, Lawrence syndrome, Cushing syndrome, acromegaly, etc.), polycystic ovary syndrome, hyperlipidemia, atherosclerosis, cardiovascular disorders (e.g., stenocardia, cardiac failure, etc.), hyperglycemia (e.g., abnormal saccharometabolism such as feeding disorders, etc.), pancreatitis, osteoporosis, hyperuricemia, hypertension, inflammatory bowel disease, skin disease accompanying abnormal differentation of epidermal cells, and further, based on their cGMP-PDE (especially PDE-V)-inhibiting activity, smooth muscle relaxing activity, bronchodilating activity, vasodilating activity, smooth muscle cell suppressing activity, and antiallergic activity, stenocardia, hypertension, pulmonary hypertension, congestive heart failure, glomerulopathy (e.g., diabetic glomerulosclerosis, etc.), tubulointerstitial disorders (e.g., renopathy induced by FK506, cyclosporin, etc.), renal failure, atherosclerosis, angiostenosis (e.g., angiostenosis after percutaneous arterioplasty), distal angiopathy, cerebral apoplexy, chronic reversible obstructions (e.g., bronchitis, asthma (chronic asthma, allergic asthma), etc.), autoimmune disease, allergic rhinitis, urticaria, glaucoma, diseases characterized by enteromotility disorders (e.g., hypersensitive enteropathy syndrome, etc.), impotence (e.g., organic impotence, psychic impotence, etc.), diabetic complications (e.g., diabetic gangrene, diabetic arthropathy, diabetic glomerulosclerosis, diabetic dermopathy, diabetic neuropathy, diabetic cataract, diabetic retinopathy, etc.), nephritis, cachexia (e.g., progressive weight reduction due to lipolysis, myodegeneration, anaemia, edema, anorexia, etc. in chronic diseases such as cancer, tuberculosis, endocrine diseases, and AIDS), pancreatitis, post-PTCA restenosis, etc. In addition, they, in combination with a retinoid, are effective for treating diseases associated with cell proliferative disorders including cancer, restenosis, and atherosclerosis.

For use in the treatment of diseases or disorders, such as those mentioned herein above, the benzimidazole derivatives of the present invention may be formulated into pharmaceutical compositions of ordinary forms, which comprise, as an active ingredient, any of the derivatives along with pharmaceutically acceptable carriers, such as organic or inorganic solid or liquid vehicles, and which are suitable for peroral administration, parenteral administration or external application. The pharmaceutical compositions may be of any solid form of tablets, granules, powders, capsules, etc., or may be of any liquid form of solutions, suspensions, syrups, emulsions, lemonades, etc.

If desired, the pharmaceutical compositions may further contain a pharmaceutical aid, a stabilizer, or a wetting agent, and also any ordinary additive of, for example, lactose, citric acid, tartaric acid, stearic acid, magnesium stearate, terra alba, sucrose, corn starch, talc, gelatin, agar, pectin, peanut oil, olive oil, cacao butter, ethylene glycol, etc.

The amount of the above-mentioned derivative of the present invention to be used shall vary, depending on the age and the condition of patients, the type and the condition of diseases or disorders, and the type of the derivative to be used. In general, for peroral administration, the dose of the derivative may be from 1 to 100 mg/kg; and for intramuscular injection or intravenous injection, it may be from 0.1 to 10 mg/kg. Such a unit dose may be applied to a patient once to four times a day.

BEST MODE FOR CARRYING OUT THE INVENTION

Figure 1:
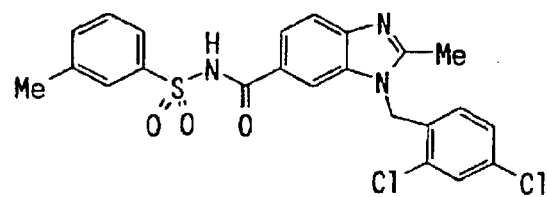
FIG. 1 shows chemical formulae of compound (1) to compound (5).
Figure 1:
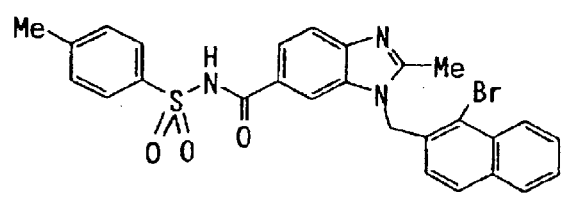
Figure 1:
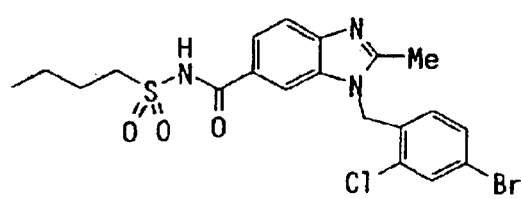
Figure 1:
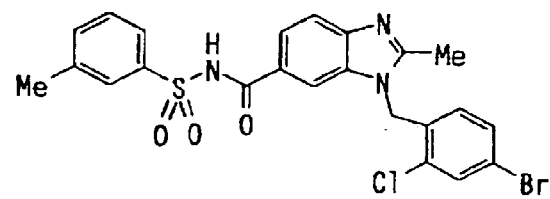
Figure 1:
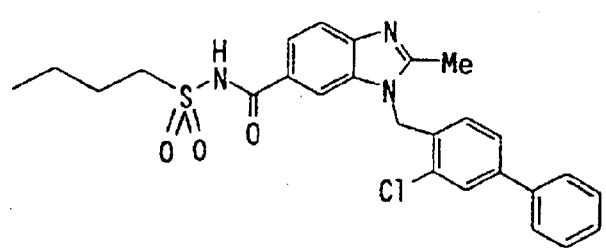
Figure 2:
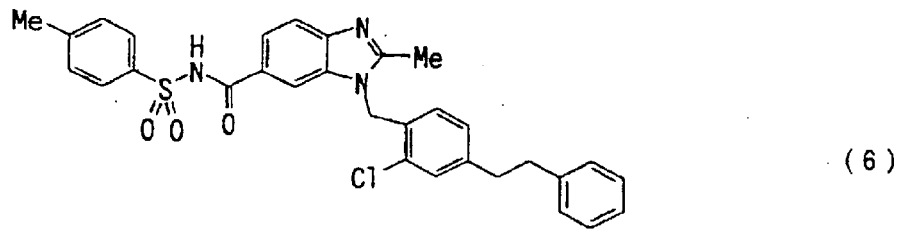
FIG. 2 shows chemical formulae of compound (6) to compound (10).
Figure 2:
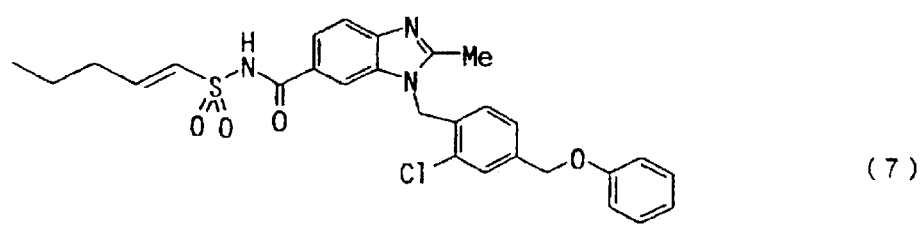
Figure 2:
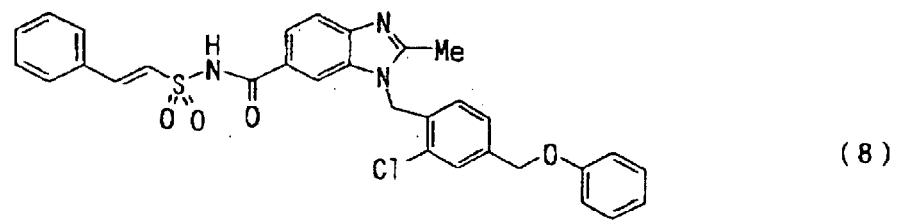
Figure 2:
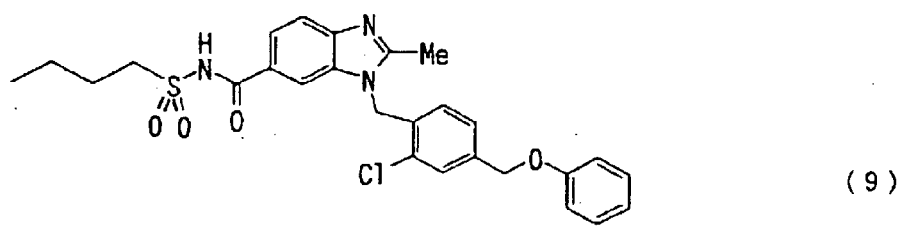
Figure 2:
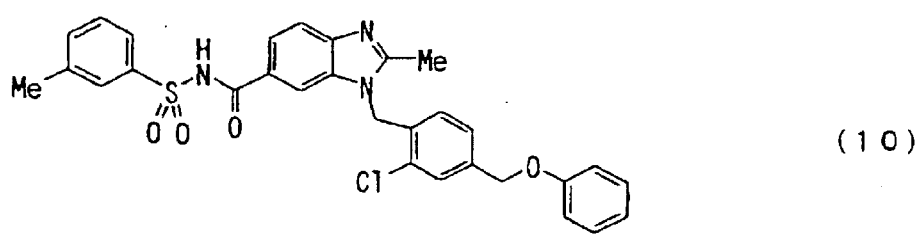
Figure 3:
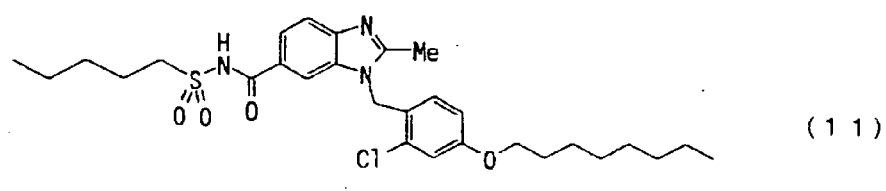
FIG. 3 shows chemical formulae of compound (11) to compound (15).
Figure 3:
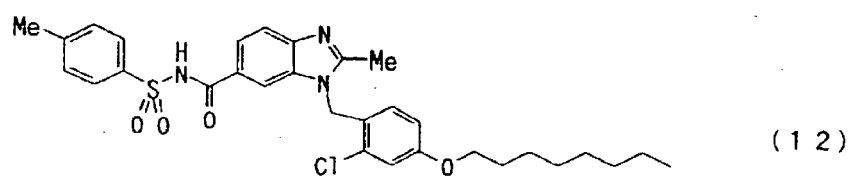
Figure 3:
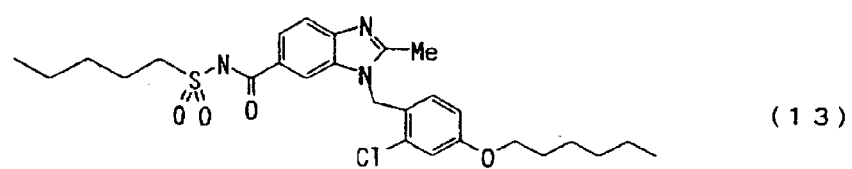
Figure 3:
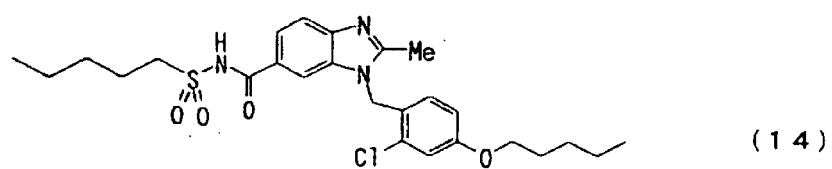
Figure 3:
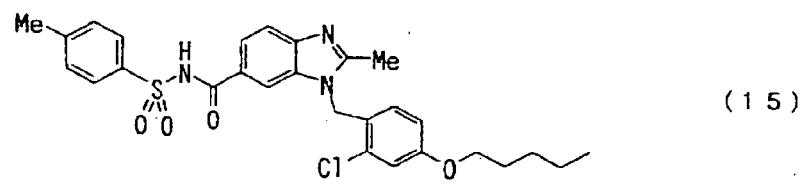
Figure 4:
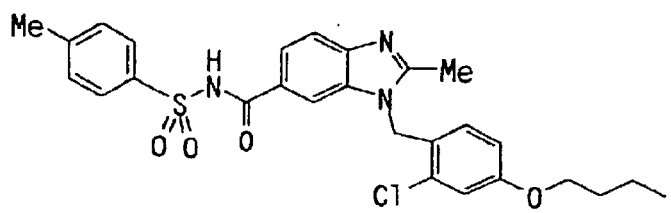
FIG. 4 shows chemical formulae of compound (16) to compound (20).
Figure 4:
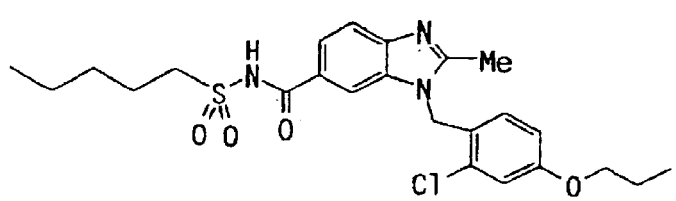
Figure 4:
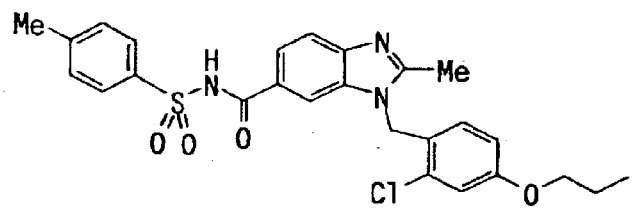
Figure 4:
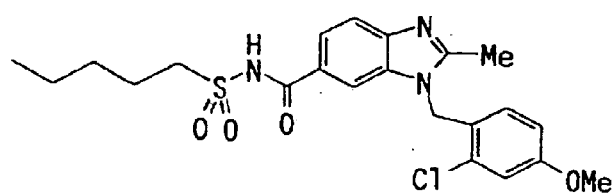
Figure 4:
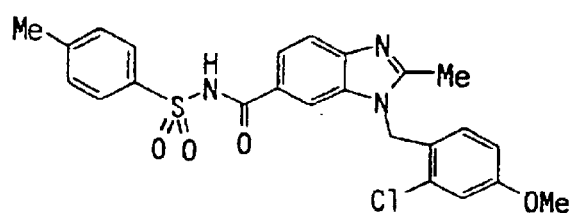
Figure 5:
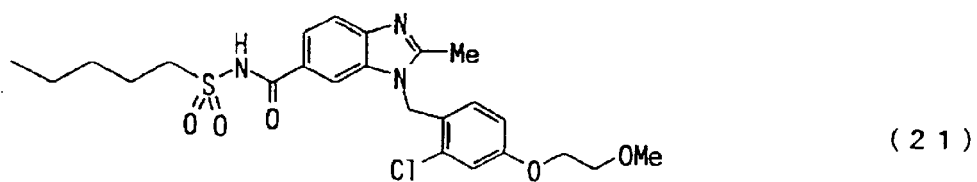
FIG. 5 shows chemical formulae of compound (21) to compound (25).
Figure 5:
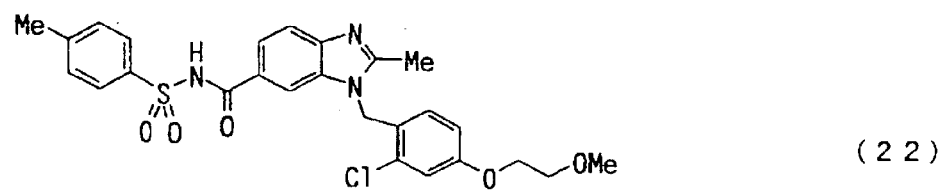
Figure 5:
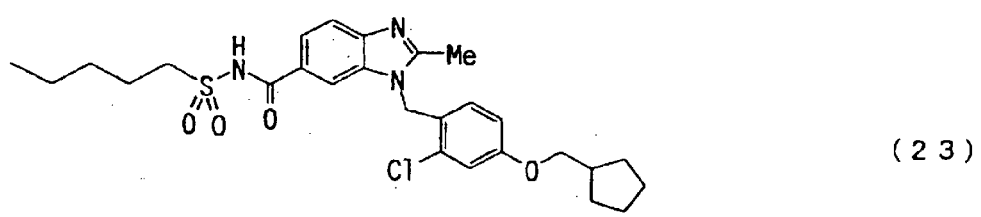
Figure 5:
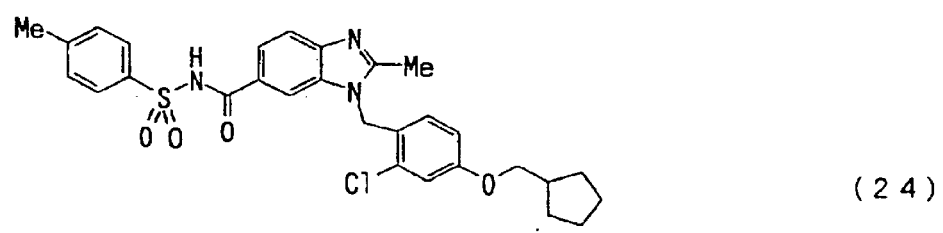
Figure 5:
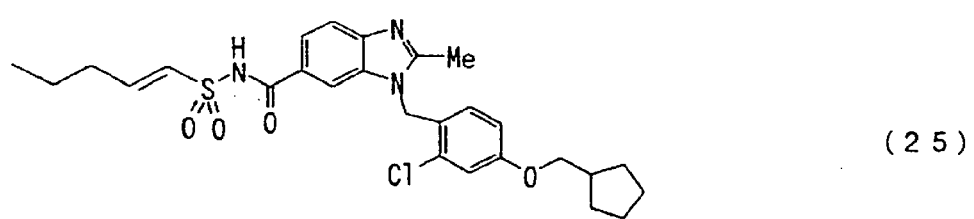
Figure 6:
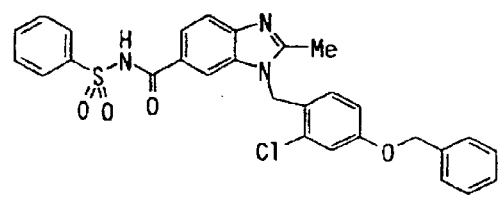
FIG. 6 shows chemical formulae of compound (26) to compound (30).
Figure 6:
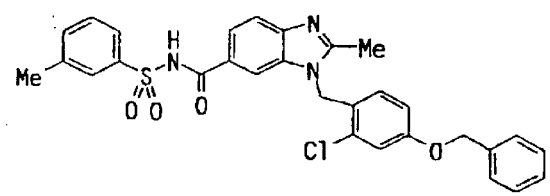
Figure 6:
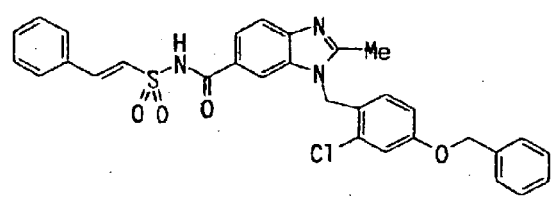
Figure 6:
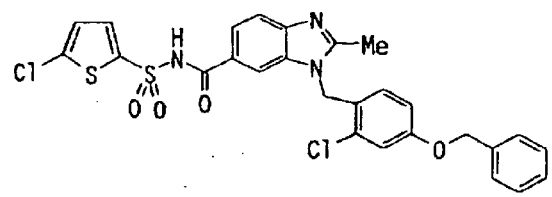
Figure 6:
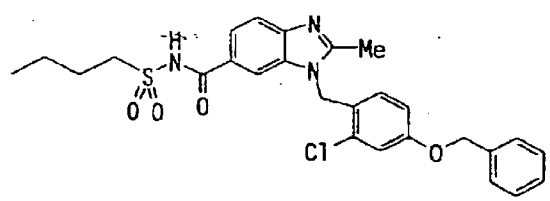
Figure 7:
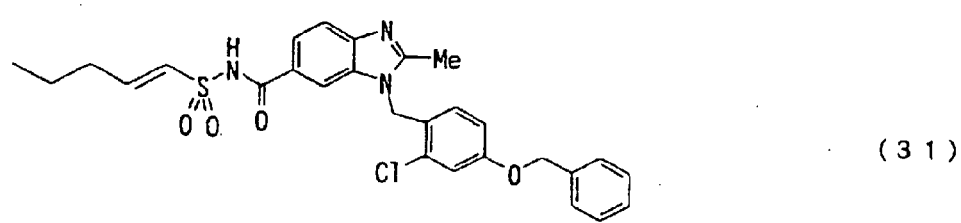
FIG. 7 shows chemical formulae of compound (31) to compound (35).
Figure 7:
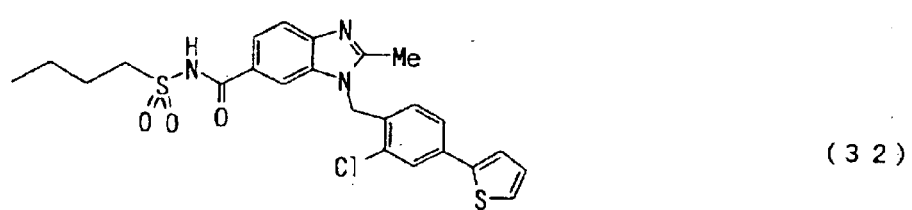
Figure 7:
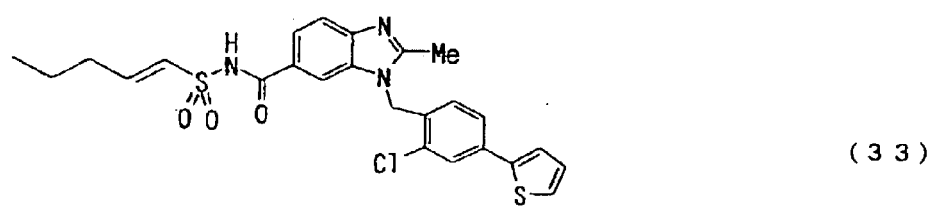
Figure 7:
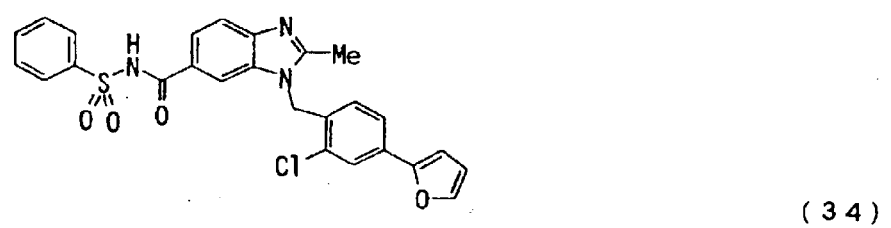
Figure 7:
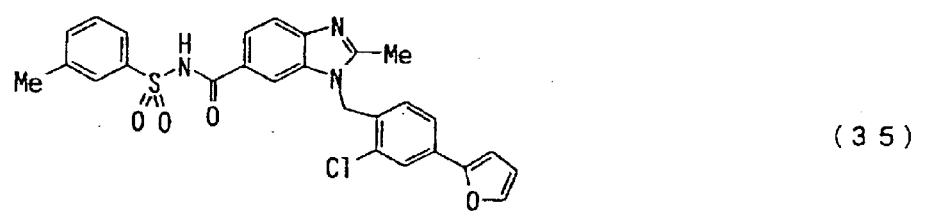
Figure 8:
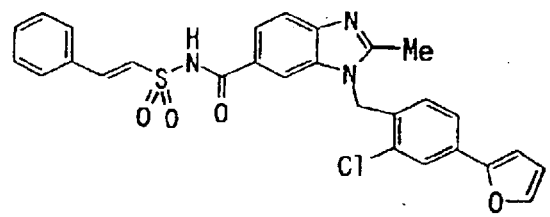
FIG. 8 shows chemical formulae of compound (36) to compound (40).
Figure 8:
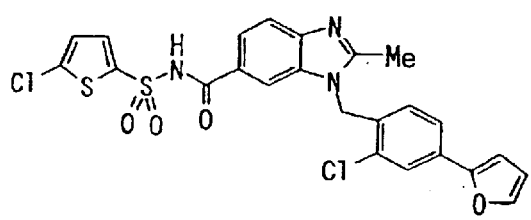
Figure 8:
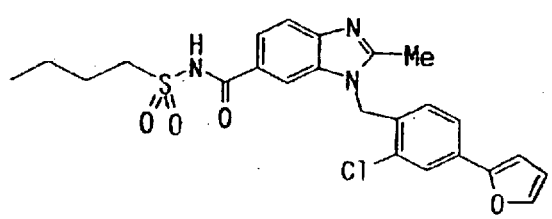
Figure 8:
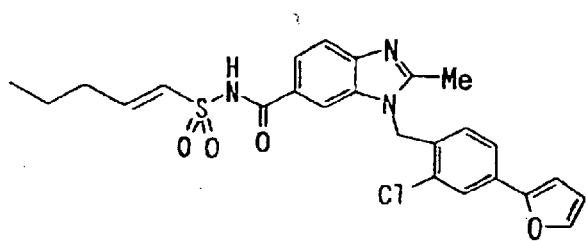
Figure 8:
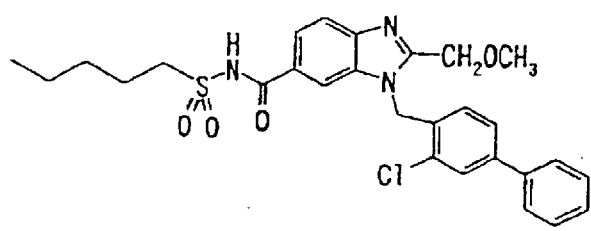
Figure 9:
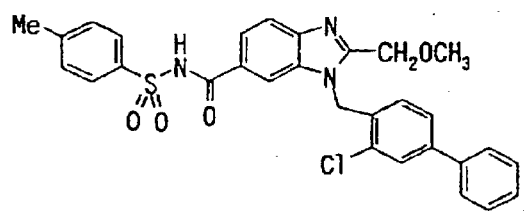
FIG. 9 shows chemical formulae of compound (41) to compound (45).
Figure 9:
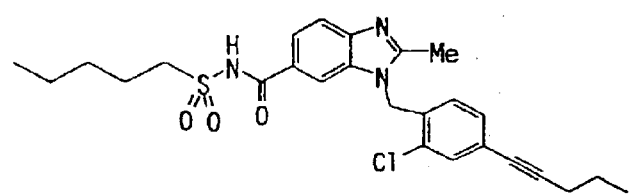
Figure 9:
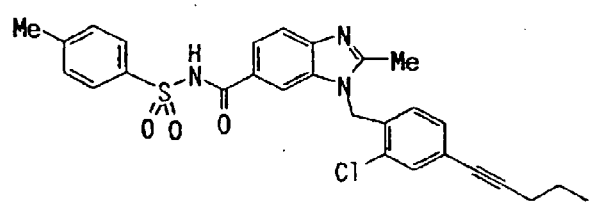
Figure 9:
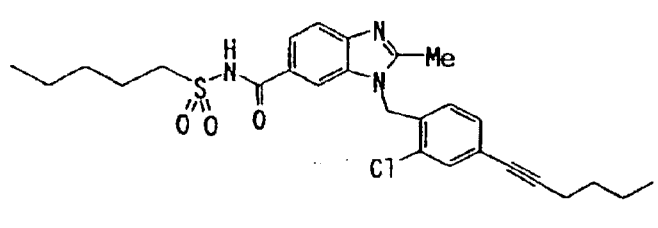
Figure 9:
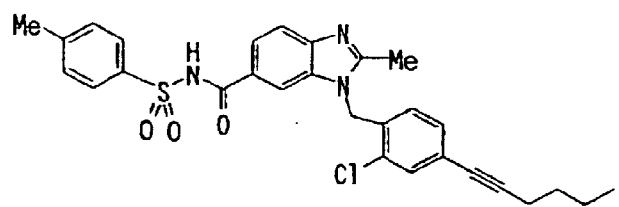
Figure 10:
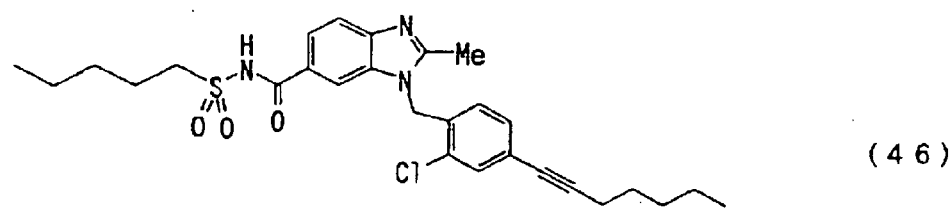
FIG. 10 shows chemical formulae of compound (46) to compound (50).
Figure 10:
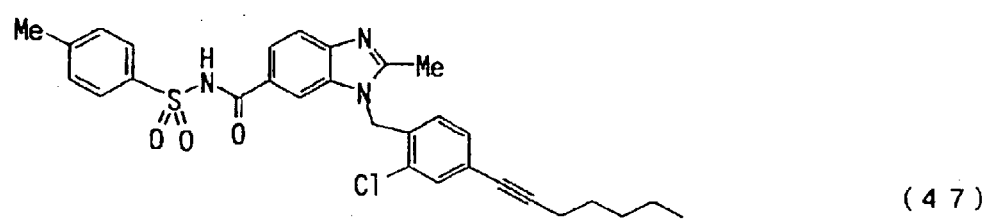
Figure 10:
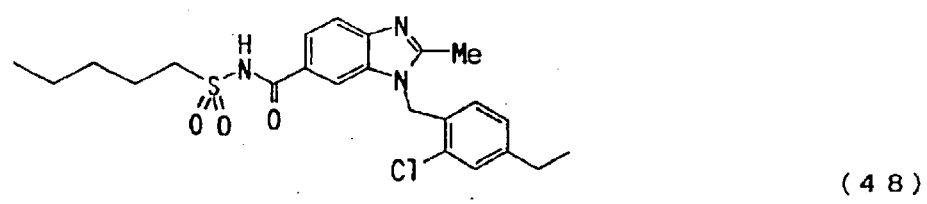
Figure 10:
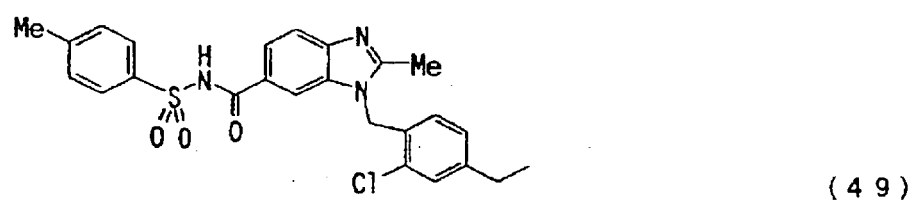
Figure 10:
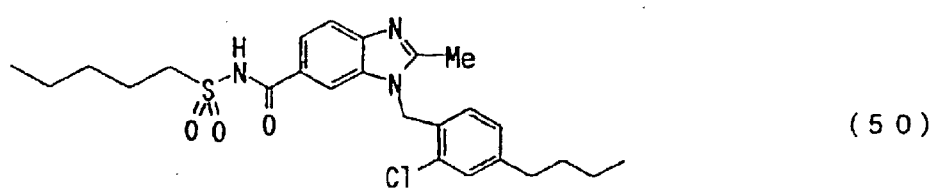
Figure 11:
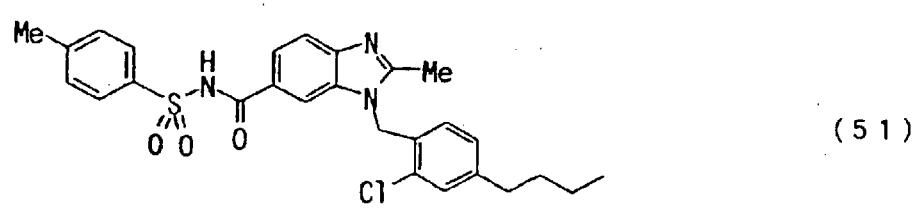
FIG. 11 shows chemical formulae of compound (51) to compound (55).
Figure 11:
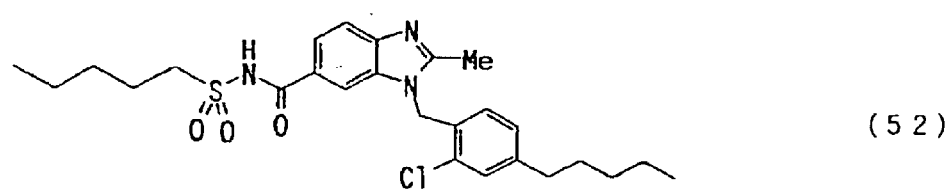
Figure 11:
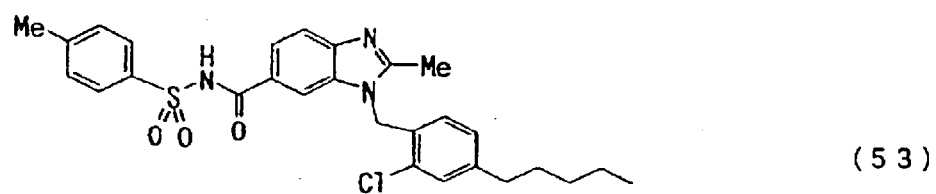
Figure 11:
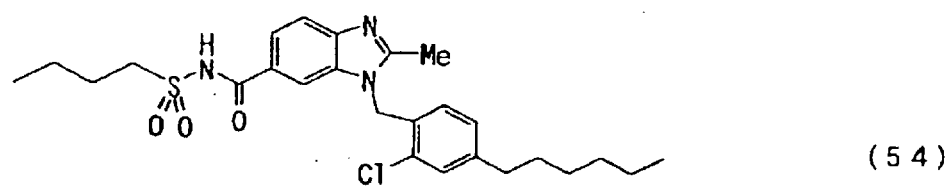
Figure 11:
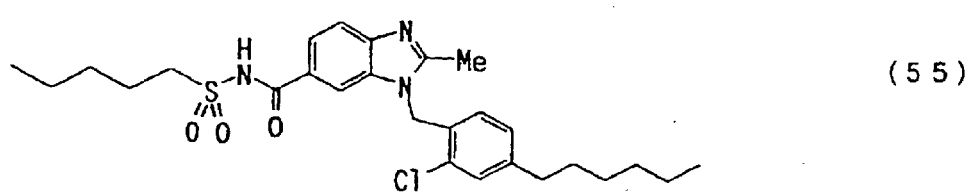
Figure 12:
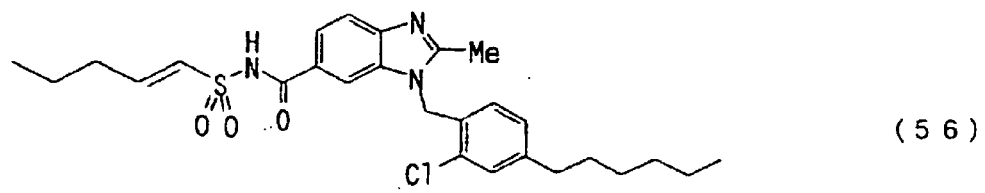
FIG. 12 shows chemical formulae of compound (56) to compound (60).
Figure 12:
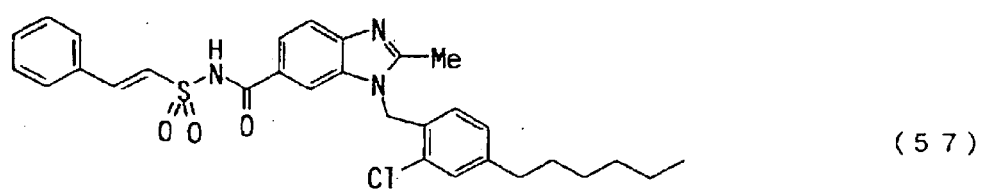
Figure 12:
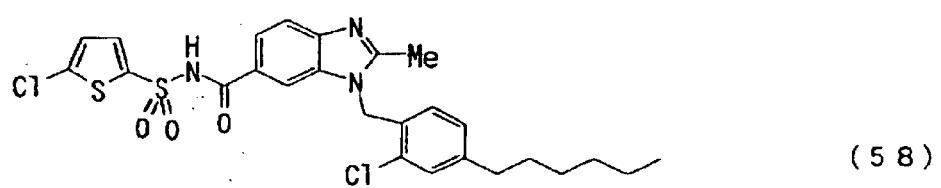
Figure 12:
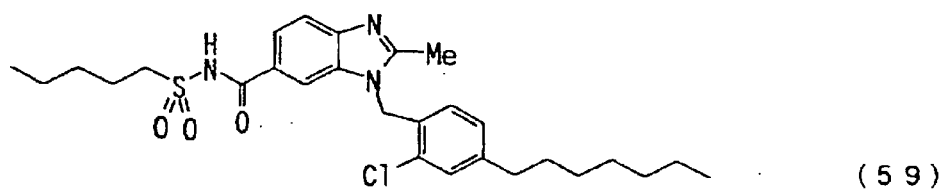
Figure 12:
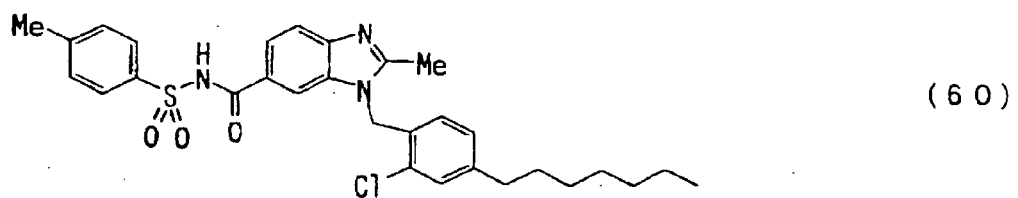
Figure 13:
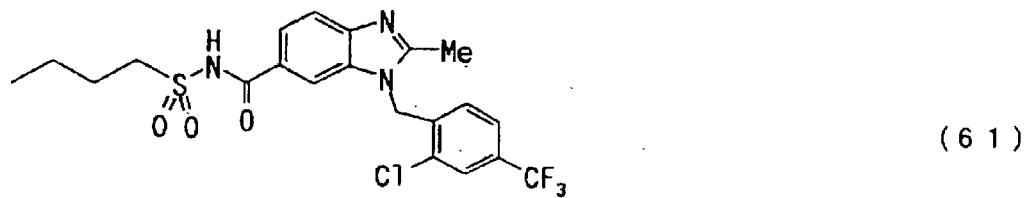
FIG. 13 shows chemical formulae of compound (61) to compound (65).
Figure 13:
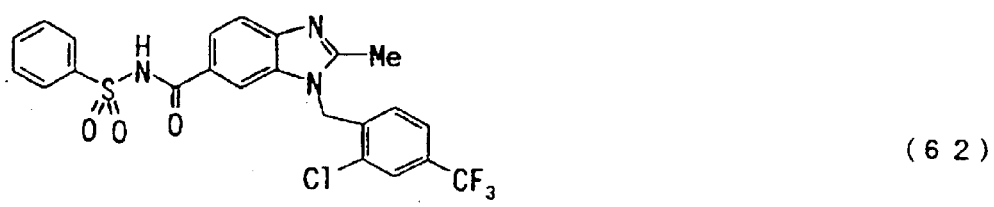
Figure 13:
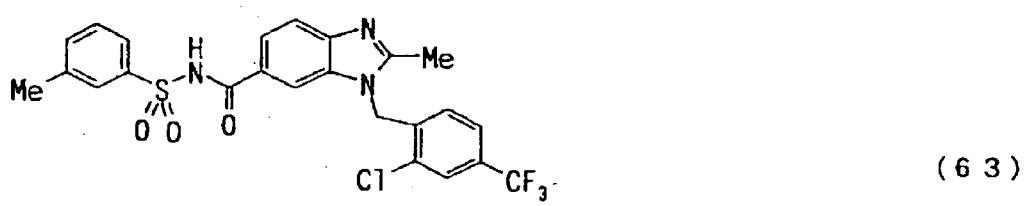
Figure 13:
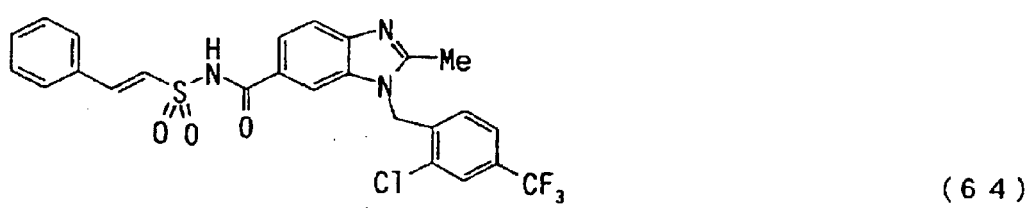
Figure 13:
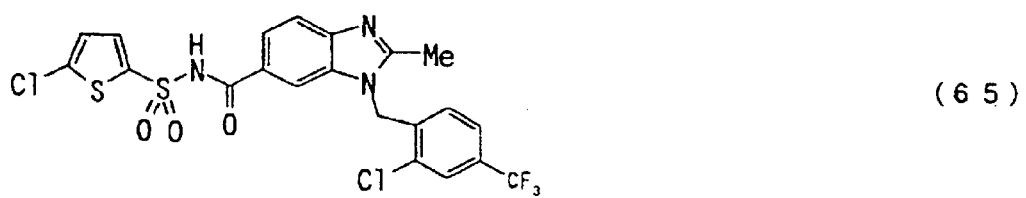
Figure 14:
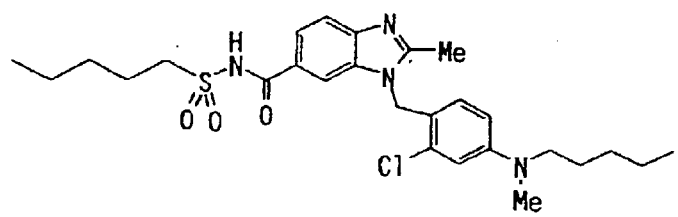
FIG. 14 shows chemical formulae of compound (66) to compound (70).
Figure 14:
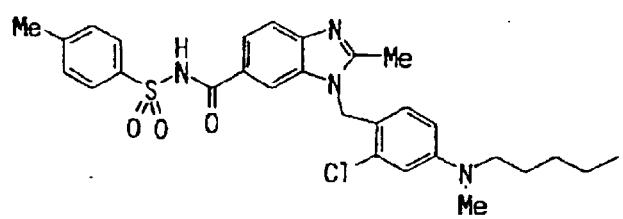
Figure 14:
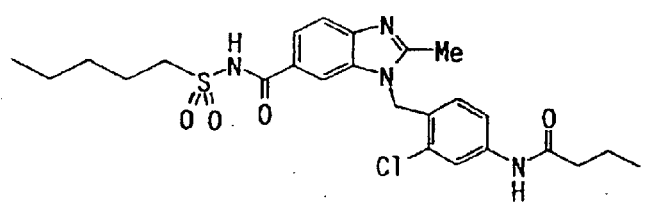
Figure 14:
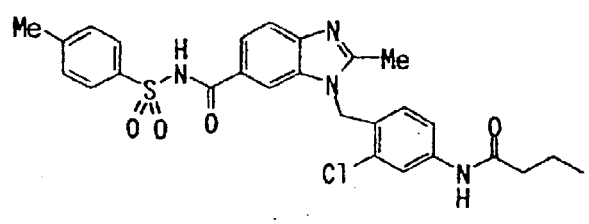
Figure 14:
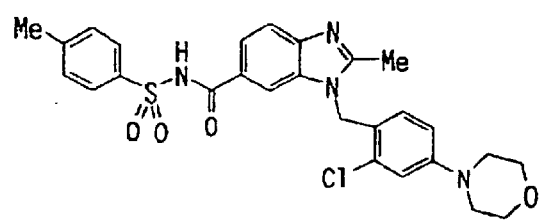
Figure 15:
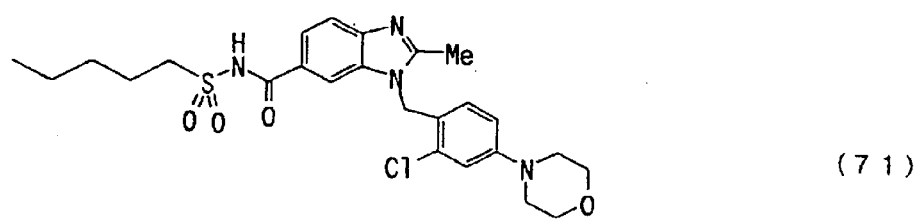
FIG. 15 shows chemical formulae of compound (71) to compound (75).
Figure 15:
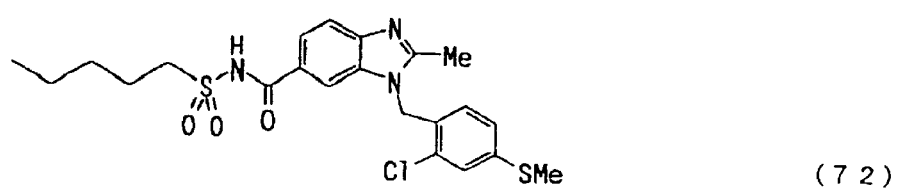
Figure 15:
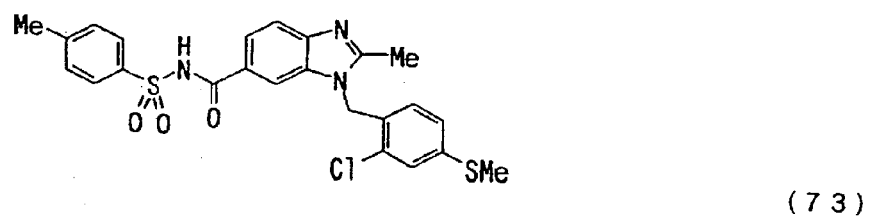
Figure 15:
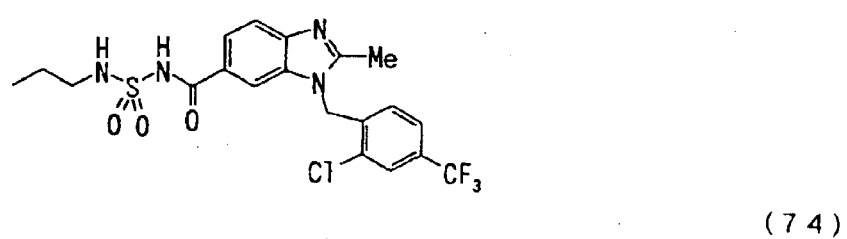
Figure 15:
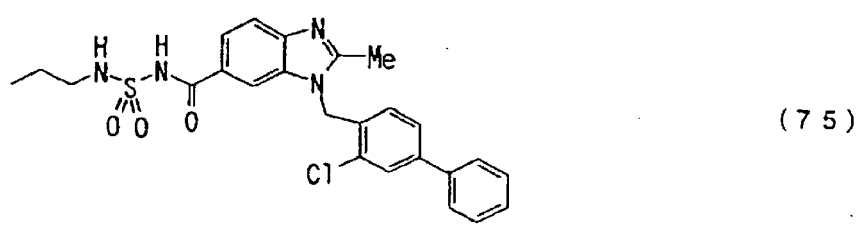
Figure 16:
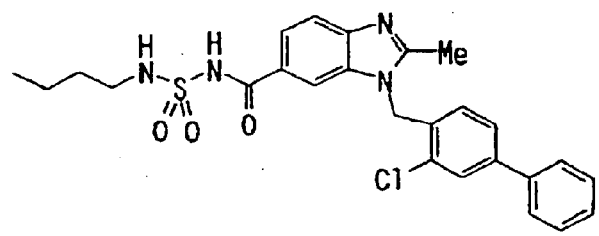
FIG. 16 shows chemical formulae of compound (76) to compound (80).
Figure 16:
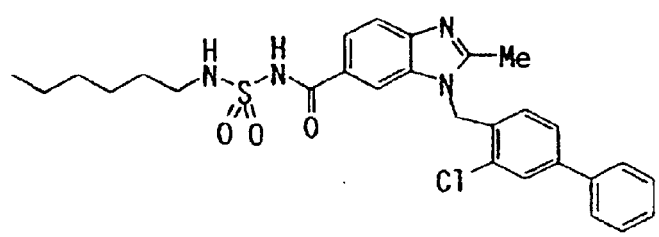
Figure 16:
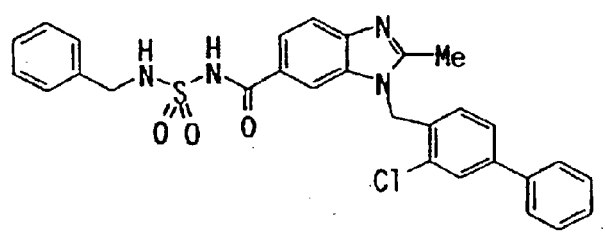
Figure 16:
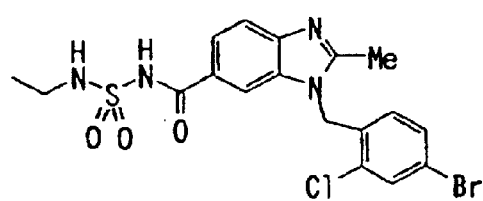
Figure 16:
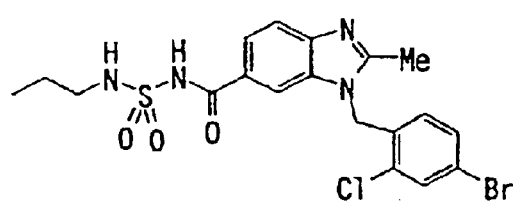
Figure 17:
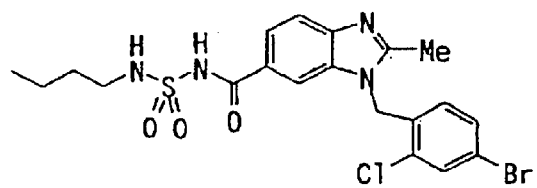
FIG. 17 shows chemical formulae of compound (81) to compound (85).
Figure 17:
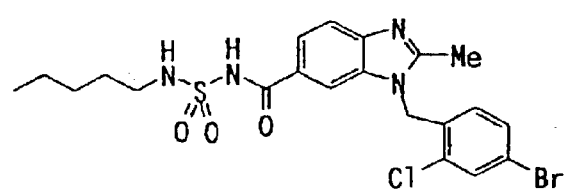
Figure 17:
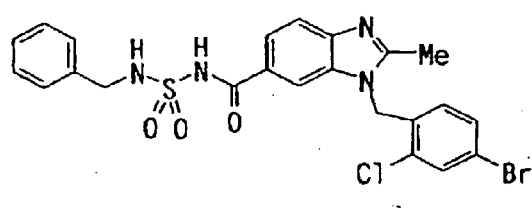
Figure 17:
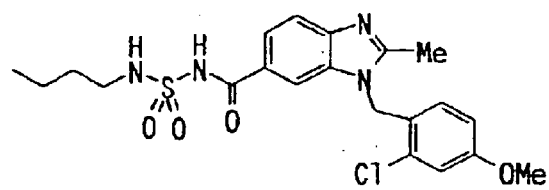
Figure 17:
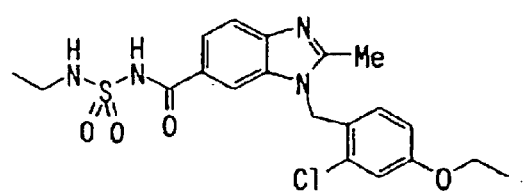
Figure 18:
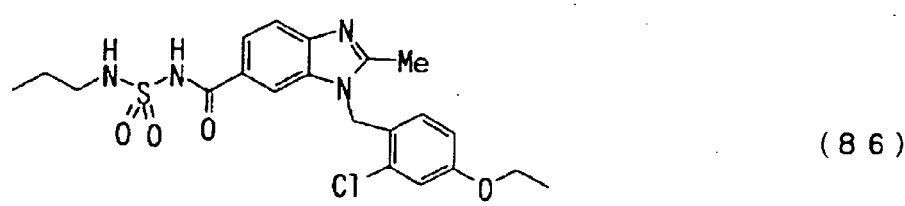
FIG. 18 shows chemical formulae of compound (86) to compound (90).
Figure 18:
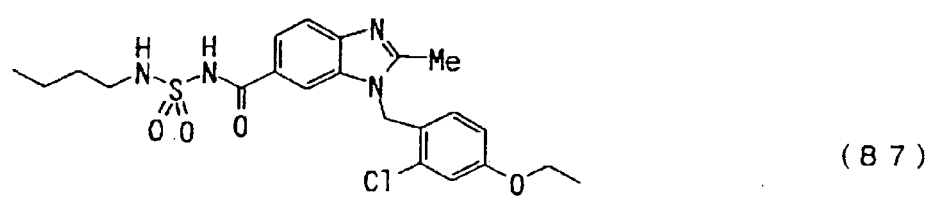
Figure 18:
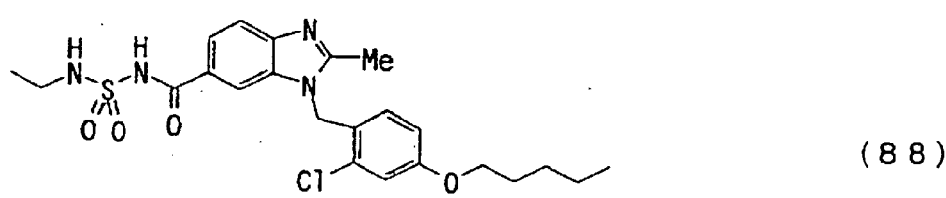
Figure 18:
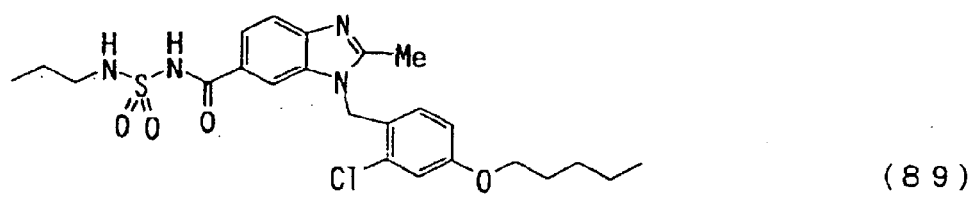
Figure 18:
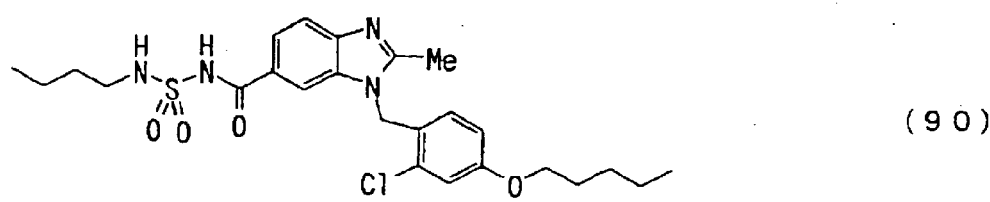
Figure 19:
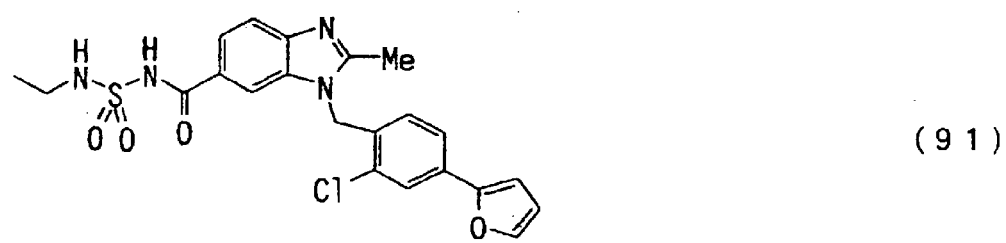
FIG. 19 shows chemical formulae of compound (91) to compound (94).
Figure 19:
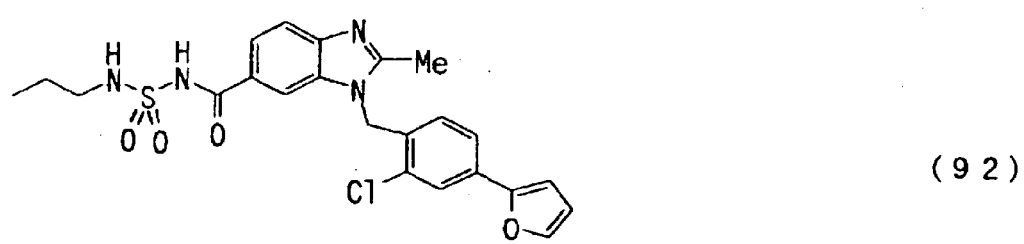
Figure 19:
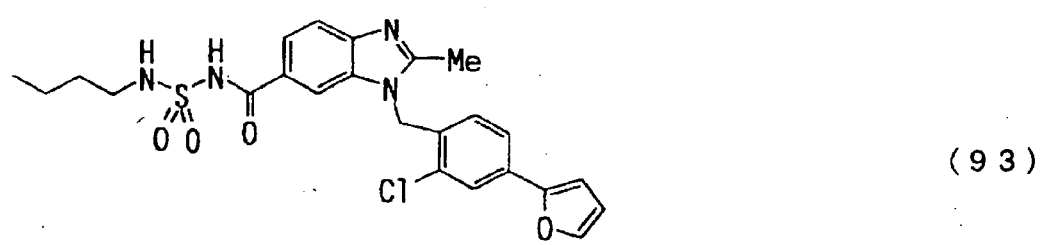
Figure 19:
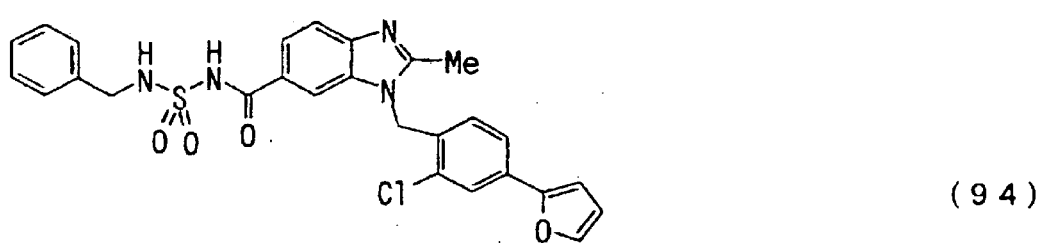
Figure 20:
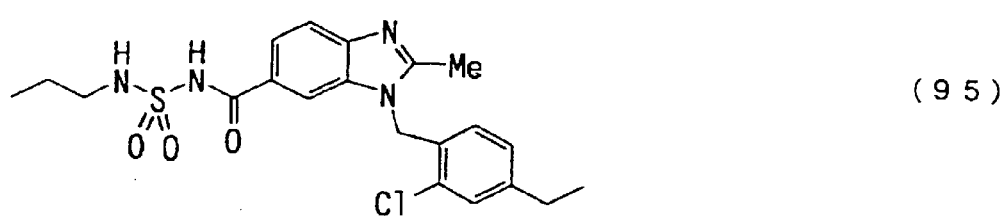
FIG. 20 shows chemical formulae of compound (95) to compound (97).
Figure 20:
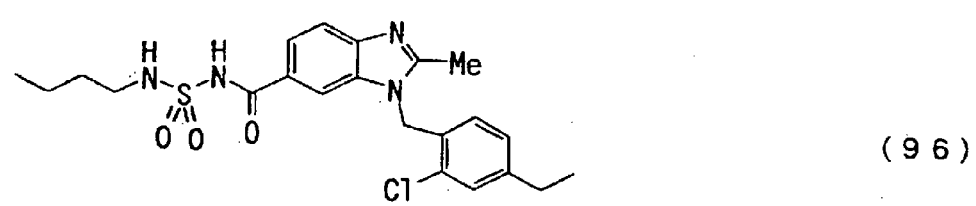
Figure 20:
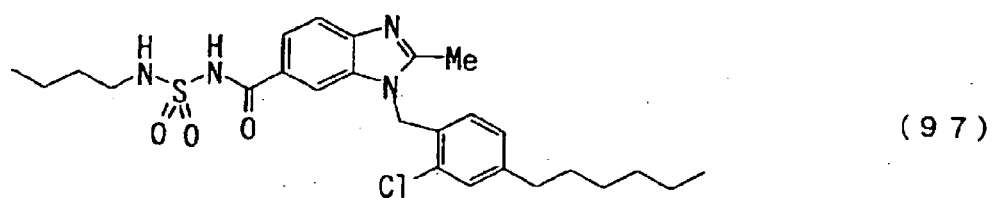

The present invention is illustrated more specifically by referring to the following Examples. However, the present invention is not limited thereto.

Production Example 1

(Step 1)
<Production of ethyl 4-(acetylamino)-3-nitrobenzoate>

Acetyl chloride (62 ml) was added dropwise to a mixture of 142 g of ethyl 4-amino-3-nitrobenzoate, 110 ml of dimethylaniline, and 940 ml of toluene in an ice bath. The reaction mixture was stirred at 50° C. for 3 hours, and was then cooled and quenched with the addition of 142 ml of water. The toluene layer was separated, and the organic layer was washed with dilute hydrochloric acid, and subsequently with water. The organic layer was concentrated to a volume of approximately ⅓ of the original volume, and 284 ml of hexane was added thereto for crystallization. The crystals were separated through filtration, and were washed with hexane to give 157.7 g of the title compound.

[Properties of the compound]
$^1$H-NMR(CDCl$_3$, δ ppm): 1.42(3H, t, J=7.1 Hz), 2.33(3H, s), 4.42(2H, q, J=7.1 Hz), 8.28(1H, dd, J=2.1 and 8.9 Hz), 8.89(1H, d, J=2.1 Hz), 8.91(1H, d, J=8.9 Hz), 10.55(1H, bts).

(Step 2)
<Production of ethyl 4-(acetylamino)-3-aminobenzoate>

A mixture of 45.3 g of a wet crystal of ethyl 4-(acetylamino)-3-nitrobenzoate (purity: 66.2%), 191.6 g of ethanol, 31.9 g of water, and 3.0 g of 5% palladium on carbon (water, content: 50%) was stirred in a hydrogen atmosphere at 40° C. for 19 hours. The catalyst was removed using a filtration aid, and washed with 30.0 g of a mixed solvent of water and ethanol at a ratio of 1:9. The filtrate was concentrated, 33.0 g of t-butylmethyl ether was added dropwise thereto at 50° C., and the mixture was cooled to 10° C. for crystallization. The crystals were collected, washed with 30.0 g of t-butylmethyl ether, and dried under reduced pressure at 60° C. to give 18.2 g of the title compound.

[Properties of the compound]
$^1$H-NMR(DMSO-d$_6$, δ ppm): 1:27(3H, t), 2.05(3H, s), 4.23(2H, q), 5.19(2H, s), 7.13(1H, d, J=8.2 Hz), 7.35(1H, s), 7.47(1H, d, J=8.2 Hz), 9.19(1H, s).

(Step 3)
<Production of ethyl 4-(acetylamino)-3-((2,4-dichlorobenzyl)amino)benzoate>

A mixture of 250 g of ethyl 4-(acetylamino)-3-aminobenzoate, 264 g of 2,4-dichlorobenzyl chloride, 187 g of potassium carbonate, 50.6 g of sodium iodide, 500 g of water, and 1100 g of ethyl acetate was stirred at 70 to 73° C. for 16 hours. The ethyl acetate layer was separated while hot, and 1500 g of t-butylmethyl ether was added thereto. The mixture was cooled to 10° C., the crystals precipitated were separated through filtration, and then they were washed with 600 g of a mixed solvent of ethyl acetate and t-butylmethyl ether at a ratio of 1:2. The crystals were dried to give 296.6 g of the title compound.

[Properties of the compound]
$^1$H-NMR(CDCl$_3$ δ ppm): 1.37(3H, t, J=7.1 Hz), 2.23(3H, s), 4.30(2H, q, J=7.1 Hz), 4.38(1H, d, J=5.3 Hz), 4.41(2H, d, J=5.7 Hz), 7.18(1H, d, J=8.3 Hz), 7.31(1H, d, J=8.3 Hz), 7.39(1H, d, J=7.3 Hz), 7.42(1H, d, J=2.0 Hz), 7.46(1H, d, J=8.2 Hz), 7.51(1H, d, J=8.2 Hz).

(Steps 4 and 5)
<Production of 6-carboxy-1-(2,4-dichlorobenzyl)-2-methylbenzimidazole>

A mixture of 250 g of ethyl 4-(acetylamino)-3-((2,4-dichlorobenzyl)amino)benzoate, 68.4 g of concentrated hydrochloric acid, and 1197 g of ethanol was refluxed for 2 hours, to give 1-(2,4-dichlorobenzyl)-6-(ethoxycarbonyl)-2-methylbenzimidazole. To this reaction solution, a solution consisting of 105 g of sodium hydroxide and 1000 g of water was added, and the reaction solution was refluxed for 2 hours. The reaction solution was cooled, and was neutralized with the slow addition of 193.3 g of concentrated hydrochloric acid. The crystals precipitated were separated through filtration, were washed with 900 ml of a mixed solution of ethanol and water at a ratio of 2:1, and were dried to give 214 g of the title compound.

[Properties of the compound]
$^1$H-NMR(DMSO-d$_6$, δ ppm): 2.52(3H, s), 5.62(2H, s), 6.53(1H, d, J=8.5 Hz), 7.33(1H, dd, J=8.5 and 2.1 Hz), 7.64(1H, d, J=8.4 Hz), 7.74(1H, d, J=2.2 Hz), 7.81(1H, dd, J=8.4 and 1.4 Hz), 7.98(1H, s), 12.74(1H, brs).

Production Example 2

(Step 1)
<Ethyl 4-(acetylamino)-3-(((1-bromonaphthalen-2-yl)methyl)amino)benzoate>

According to the procedure of Step 3 in Production Example 1, the title compound was produced from 0.50 g of ethyl 4-(acetylamino)-3-aminobenzoate, 0.81 g of 1-bromo-2-(bromomethyl)naphthalene, 0.38 g of sodium carbonate, and 0.10 g of sodium iodide. This compound was used immediately in the subsequent step.

(Steps 2 and 3)
<1-((1-Bromonaphthalen-2-yl)methyl)-6-carboxy-2-methylbenzimidazole>

According to the procedures of Steps 4 and 5 in Production Example 1, 0.514 g of the title compound was produced from ethyl 4-(acetylamino)-3-(((1-bromonaphthalen-2-yl)methyl)amino)benzoate obtained in the step above.

[Properties of the compound]
$^1$H-NMR(DMSO-d$_6$, δ ppm): 2.56(3H, s), 5.84(2H, s), 6.61(1H, d, J=8.6 Hz), 7.63(1H, t, J=7.8 Hz), 7.66(1H, d, J=8.5 Hz), 7.75(1H, t, J=7.8 Hz), 7.81(1H, d, J=8.6 Hz), 7.86(1H, d, J=8.6 Hz), 7.95(1H, d, J=8.2 Hz), 7.99(1H, s), 8.30(1H, d, J=8.6 Hz), 12.69(1H, s).

Production Example 3

(Step 1)
<Production of ethyl 4-(acetylamino)-3-((4-bromo-2-chlorobenzyl)amino)benzoate>

According to the procedure of Step 3 in Production Example 1, 3.00 g of the title compound was produced from 2.22 g of ethyl 4-(acetylamino)-3-aminobenzoate, 2.60 g of 4-bromo-2-chlorobenzyl bromide, and 1.66 g of potassium carbonate.

[Properties of the compound]
$^1$H-NMR(DMSO-d$_6$, δ ppm): 1.23(3H, d, J=7.1 Hz), 2.10(3H, s), 4.18(2H, q, J=7.1 Hz), 4.39(2H, d, J=5.8 Hz), 6.05(1H, t, J=5.8 Hz), 6.89(1H, dm J=1.7 Hz), 7.19(1H, dd, J=1.7 and 8.2 Hz), 7.35(1H, d, J=8.3 Hz), 7.40(1H, d, J=8.2 Hz), 7.50(1H, dd, J=1.8 and 8.3 Hz), 7.75(1H, d, J=1.7 Hz), 9.38(1H, s).

(Steps 2 and 3)
<Production of 1-(4-bromo-2-chlorobenzyl)-6-carboxy-2-methylbenzimidazole>

According to the procedures of Steps 4 and 5 in Production Example 1, 2.03 g of the title compound was produced from 3.00 g of ethyl 4-(acetylamino)-3-((4-bromo-2-chlorobenzyl)amino)benzoate via 1-(4-bromo-2-chlorobenzyl)-6-(ethoxycarbonyl)-2-methylbenzimidazole.

[Properties of the compound]
$^1$H-NMR(DMSO-d$_6$, δ ppm): 2.50(3H, s), 5.58(2H, s), 6.45(1H, d, J=8.4 Hz), 7.45(1H, dd, J=2.0 and 8.4 Hz), 7.63(1H, d, J=8.4 Hz), 7.80(1H, dd, J=1.4 and 8.4 Hz), 7.84(1H, d, J=2.0 Hz), 7.97(1H, d, J=1.4 Hz), 12.7(1H, brs).

Production Example 4

(Step 1)
<Production of ethyl 4-(acetylamino)-3-((2-chloro-4-phenylbenzyl)amino)benzoate>

According to the procedure of Step 3 in Production Example 1, 3.10 g of the title compound was produced from 2.22 g of ethyl 4-(acetylamino)-3-aminobenzoate, 3.37 g of 2-chloro-4-phenylbenzyl bromide, and 1.66 g of potassium carbonate.

[Properties of the compound]
¹H-NMR(CDCl₃, δ ppm): 1.36(3H, t, J=7.1 Hz), 1.92(1H, brs), 2.23(3H, s), 4.2–4.6(5H, m), 7.37(1H, t, J=7.3 Hz), 7.41–7.58(9H, m), 7.64(1H, s).

(Steps 2 and 3)
<Production of 6-carboxy-1-(2-chloro-4-phenylbenzyl)-2-methylbenzimidazole>

According to the procedures of Steps 3 and 4 in Production Example 1, 2.50 g of the title compound was produced from 3.00 g of ethyl 4-(acetylamino)-3-((2-chloro-4-phenylbenzyl)amino)benzoate via 1-(2-chloro-4-phenylbenzyl)-6-(ethoxycarbonyl)-2-methylbenzimidazole.

[Properties of the compound]
¹H-NMR(DMSO-d₆, δ ppm): 2.68(3H, s), 7.76(2H, s), 6.79(1H, d, J=8.1 Hz), 7.38(1H, t, J=7.2 Hz), 7.45(2H, t), 7.56(1H, dd, J=1.7 and 8.1 Hz), 7.67(2H, d, J=7.4 Hz), 7.76(1H, d, J=8.5 Hz), 7.86(1H, d, J=1.7 Hz), 7.93(1H, d, J=8.5 Hz), 13.0(1H, brs).

Production Example 5

(Step 1)
<Production of ethyl 4-(acetylamino)-3-((2-chloro-4-(phenyl-oxymethyl)benzyl)amino)benzoate>

According to the procedure of Step 3 in Production Example 1, 1.63 g of the title compound was produced from 0.80 g of ethyl 4-(acetylamino)-3-aminobenzoate, 0.96 g of 2-chloro-4-(phenyloxymethyl)benzyl chloride, 0.47 g of sodium carbonate, and 0.30 g of sodium iodide. This compound was used immediately in the subsequent step.

(Steps 2 and 3)
<Production of 6-carboxy-1-(2-chloro-4-(phenyloxymethyl)benzyl)-2-methylbenzimidazole>

According to the procedures of Steps 4 and 5 in Production Example 1, 0.78 g of the title compound was produced from 1.63 g of ethyl 4-(acetylamino)-3-((2-chloro-4-(phenyloxymethyl)benzyl)amino)benzoate via 1-(2-chloro-4-(phenyloxymethyl)benzyl)-6-(ethoxycarbonyl)-2-methylbenzimidazole.

[Properties of the compound]
¹H-NMR(DMSO-d₆, δ ppm): 2.52(3H, s), 5.07(2H, s), 5.61(2H, s), 6.56(1H, d, J=7.8 Hz), 6.92(1H, t, J=7.1 Hz), 6.97(2H, d, J=7.5 Hz), 7.27(3H, m), 7.62(2H, s), 7.79(1H, d, J=8.0 Hz), 7.95(1H, s).

Production Example 6

(Steps 1 and 2)
<Production of 1-(2-chloro-4-hydroxybenzyl)-6-(ethoxycarbonyl)-2-methylbenzimidazole>

A mixture of 6.34 g of ethyl 4-(acetylamino)-3-aminobenzoate, 14.0 g of 4-acetoxy-2-chlorobenzyl bromide, 5.12 g of potassium carbonate, 1.28 g of sodium iodide, 35 ml of ethyl acetate, and 13 ml of water was stirred at 70° C. for 15 hours. After the reaction was completed, the solution was separated. After washed with water, the organic layer was concentrated under reduced pressure. To the oily residue, 30 ml of ethanol and 3.2 g of 35% hydrochloric acid was added and the solution was stirred at 70° C. for 3 hours. The reaction solution was extracted with ethyl acetate and water. The organic layer was concentrated, and, for crystallization, ethanol was added to the residue obtained. The crystals obtained through filtration were dried to give 1.53 g of 1-(2-chloro-4-hydroxybenzyl)-6-(ethoxycarbonyl)-2-methylbenzimidazole. The filtrate was concentrated, and, for crystallization, ethanol was added to the residue obtained. The crystals obtained through filtration were dried to give 4.72 g of 1-(2-chloro-4-hydroxybenzyl)-6-(ethoxycarbonyl)-2-methylbenzimidazole.

[Properties of the compound]
¹H-NMR(CDCl₃, δ ppm): 1.39(3H, t, J=7.1 Hz), 2.50(3H, s), 4.37(2H, q, J=7.1 Hz), 5.37(2H, s), 6.14(1H, d, J=8.4 Hz), 6.47(1H, dd, J=8.5 and 2.2 Hz), 7.01(1H, d, J=2.2 Hz), 7.67(1H, d, J=8.4 Hz), 7.96(1H, d, J=8.8 Hz), 7.99(1H, s).

(Step 3)
<Production of 1-(4-n-butyloxy-2-chlorobenzyl)-6-(ethoxycarbonyl)-2-methylbenzimidazole>

N,N-dimethylformamide (5 ml) was added to 0.20 g of an oily substance of 60% sodium hydride, to which 0.80 g of the crystals of 1-(2-chloro-4-hydroxybenzyl)-6-(ethoxycarbonyl)-2-methylbenzimidazole was added portionwise at room temperature. After the solution was stirred at room temperature for 1 hour, 0.28 g of n-butyl bromide (4.14 mmol) was added, and the solution was stirred at room temperature for another 15 hours. The reaction solution was diluted and extracted with water and ethyl acetate. The organic layer was washed twice with water, and then concentrated to give 0.62 g of the title compound as an oil.

[Properties of the compound]
¹H-NMR(CDCl₃, δ ppm): 0.95(3H, t, J=7.5 Hz), 1.39(3H, t, J=7.3 Hz), 1.42–1.50(2H, m), 1.70–1.78(2H, m), 2.57(3H, s), 3.90(2H, t, J=6.4 Hz), 4.37(2H, q, J=6.9 Hz), 5.38(2H, s), 6.37(1H, d, J=8.6 Hz), 6.62(1H, dd, J=8.6 and 2.5 Hz), 7.00(1H, d, J=2.5 Hz), 7.73(1H, d, J=8.5 Hz), 7.96(1H, s), 7.98(1H, d, J=8.6 Hz).

(Step 4)
<Production of 1-(4-n-butyloxy-2-chlorobenzyl)-6-carboxy-2-methylbenzimidazole>

Sodium hydroxide (0.17 g), 8 ml of ethanol, and 4 ml of water were added to 0.62 g of 1-(4-n-butyloxy-2-chlorobenzyl)-6-(ethoxycarbonyl)-2-methylbenzimidazole, and the mixture was stirred at 80° C. for 4 hours. The solution was adjusted to a pH of about 5 with 35% hydrochloric acid. The precipitated crystals were filtered and dried to give 0.42 g of the title compound as crystals.

[Properties of the compound]
¹H-NMR(DMSO-d₆, δ ppm): 0.89(3H, t, J=7.5 Hz), 1.35–1.42(2H, m), 1.60–1.68(2H, m), 2.52(3H,s), 3.94(2H, t, J=6.4 Hz), 5.51(2H, s), 6.56(1H, d, J=8.7 Hz), 6.81(1H, dd, J=8.7 and 2.5 Hz), 7.10(1H, d, J=2.5 Hz), 7.61(1H, d, J=8.4 Hz), 7.88(1H, dd, J=8.4 and 1.3 Hz), 7.94(1H, s), 12.68(1H, brs).

Production Example 7

(Step 1)
<Production of 1-(2-chloro-4-(n-octyloxy)benzyl)-6-(ethoxycarbonyl)-2-methylbenzimidazole>

According to the procedure of Step 3 in Production Example 6, 1.03 g of the title compound was produced from 0.124 g of an oily substance of 60% sodium hydride, 4 ml of N,N-dimethylformamide, 0.80 g of 1-(2-chloro-4-hydroxybenzyl)-6-(ethoxycarbonyl)-2-methylbenzimidazole, and 0.994 g of n-octyl iodide.

[Properties of the compound]
¹H-NMR(CDCl₃, δ ppm): 0.85–0.95(3H, m), 1.25–1.46 (10, m), 1.42(3H, t, J=6.1 Hz), 1.73–1.81(2H, m), 2.56(3H, s), 3.89(2H, t, J=6.6 Hz), 4.37(2H, q, J=7.0 Hz), 5.38(2H, s), 6.37(1H, d, J=8.7 Hz), 6.62(1H, dd, J=8.7 and 2.5 Hz), 6.99(1H, d, J=2.5 Hz), 7.73(1H, d, J=8.4 Hz), 7.95–8.04(2H, m).

(Step 2)
<Production of 6-carboxyl-(2-chloro-4-(n-octyloxy) benzyl)-2-methylbenzimidazole>

According to the procedure of Step 4 in Production Example 6, 0.607 g of the title compound was produced from 1.03 g of 1-(2-chloro-4-(n-octyloxy)benzyl)-6-(ethoxycarbonyl)-2-methylbenzimidazole.

[Properties of the compound]
¹H-NMR(DMSO-$d_6$, δ ppm): 0.83(3H, t, J=7.0 Hz), 1.19–1.39(10H, m), 1.65(2H, m), 3.93(2H, t, J=6.5 Hz), 5.51(2H, s), 6.55(1H, d, J=8.8 Hz), 6.81(1H, dd, J=8.7 and 2.5 Hz), 7.10(1H, d, J=2.5 Hz), 7.61(1H, d, J=8.5 Hz), 7.78(1H, dd, J=8.4 and 1.5 Hz), 7.94(1H, d, J=1.1 Hz), 12.68(1H, brs).

Production Example 8

(Step 1)
<Production of 1-(2-chloro-4-(n-hexyloxy)benzyl)-6-(ethoxycarbonyl)-2-methylbenzimidazole>

According to the procedure of Step 3 in Production Example 6, 0.94 g of the title compound was produced from 0.093 g of an oily substance of 60% sodium hydride, 5 ml of N,N-dimethylformamide, 0.600 g of 1-(2-chloro-4-hydroxybenzyl)-6-(ethoxycarbonyl)-2-methylbenzimidazole, and 0.657 g of n-hexyl iodide. The compound obtained was used in the subsequent step, without further treatments.

(Step 2)
<Production of 6-carboxy-1-(2-chloro-4-(n-hexyloxy)benzyl)-2-methylbenzimidazole>

According to the procedure of Step 4 in Production Example 6, 0.35 g of the title compound was produced from 0.94 g of 1-(2-chloro-4-(n-hexyloxy)benzyl)-6-(ethoxycarbonyl)-2-methylbenzimidazole.

[Properties of the compound]
¹H-NMR(DMSO-$d_6$, δ ppm): 0.84(3H, t, J=7.0 Hz), 1.23–1.30(4H, m), 1.32–1.38(2H, m), 1.62–1.68(2H, m), 2.52(3H, s), 3.92(2H, t, J=6.5 Hz), 5.51(2H, s), 6.55(1H, d, J=8.2 Hz), 6.81(1H, dd, J=8.6 and 2.6 Hz), 7.10(1H, d, J=2.6Hz), 7.60(1H, d, J=8.4 Hz), 7.87(1H, d, J=8.4 and 1.5 Hz), 7.93(1H, d, J=1.3 Hz).

Production Example 9

(Step 1)
<Production of 1-(2-chloro-4-(n-pentyloxy)benzyl)-6-(ethoxycarbonyl)-2-methylbenzimidazole>

According to the procedure of Step 3 in Production Example 6, the title compound was produced from 0.174 g of an oily substance of 60% sodium hydride, 5 ml of N,N-dimethylformamide, 1.00 g of 1-(2-chloro-4-hydroxybenzyl)-6-(ethoxycarbonyl)-2-methylbenzimidazole, and 1.149 g of n-pentyl iodide. This compound was used immediately in the subsequent reaction.

(Step 2)
<Production of 6-carboxy-1-(2-chloro-4-(n-pentyloxy)benzyl)-2-methylbenzimidazole>

According to the procedure of Step 4 in Production Example 6, 0.915 g of the title compound was produced from 1-(2-chloro-4-(n-pentyloxy)benzyl)-6-(ethoxycarbonyl)-2-methylbenzimidazole which was obtained by the above-mentioned procedure.

[Properties of the compound]
¹H-NMR(DMSO-$d_6$, δ ppm): 0.85(3H, t, J=7.0 Hz), 1.26–1.37(4H, m), 1.62–1.69(2H, m), 2.49(3H, s), 3.93(2H, t, J=6.6 Hz), 5.51(2H, s), 6.55(1H, d, J=8.6 Hz), 6.81(1H, dd, J=8.6 and 2.5 Hz), 7.10(1H, d, J=2.5 Hz), 7.60(1H, d, J=8.4 Hz), 7.77(1H, d, J=8.3 Hz), 7.93(1H, s).

Production Example 10

(Step 1)
<Production of 1-(2-chloro-4-(n-propyloxy)benzyl)-6-(ethoxycarbonyl)-2-methylbenzimidazole>

According to the procedure of Step 3 in Production Example 6, the title compound was produced from 0.174 g of an oily substance of 60% sodium hydride, 5 ml of N,N-dimethylformamide, 1.00 g of 1-(2-chloro-4-hydroxybenzyl)-6-(ethoxycarbonyl)-2-methylbenzimidazole, and 0.986 g of n-propyl iodide. This compound was used immediately in the subsequent reaction.

(Step 2)
<Production of 6-carboxy-1-(2-chloro-4-(n-propyloxy)benzyl)-2-methylbenzimidazole>

According to the procedure of Step 4 in Production Example 6, 0.835 g of the title compound was produced from 1-(2-chloro-4-(n-propyloxy)benzyl)-6-(ethoxycarbonyl)-2-methylbenzimidazole which was obtained by the above-mentioned procedure.

[Properties of the compound]
¹H-NMR(DMSO-$d_6$, δ ppm): 0.92(3H, t, J=7.4 Hz), 1.64–1.71(2H, m), 2.49(3H, s), 3.90(2H, t, J=6.6 Hz), 5.51(2H, s), 6.55(1H, d, J=8.7 Hz), 6.81(1H, dd, J=8.5 and 2.5 Hz), 7.10(1H, d, J=2.4 Hz), 7.60(1H, d, J=8.4 Hz), 7.78(1H, d, J=8.4 Hz), 7.94(1H, s).

Production Example 11

(Step 1)
<Production of ethyl 4-(acetylamino)-3-((2-chloro-4-(ethyloxy)benzyl)amino)benzoate>

According to the-procedure of Step 1 in Production Example 1, 1.34 g of the title compound was produced from 1.12 g of ethyl 4-(acetylamino)-3-aminobenzoate, 0.96 g of 2-chloro-4-(ethyloxy)benzyl chloride, 0.80 g of sodium carbonate, and 0.38 g of sodium iodide. This compound was used immediately in the subsequent step.

(Steps 2 and 3)
<Production of 6-carboxy-1-(2-chloro-4-(ethyloxy)benzyl)-2-methylbenzimidazole>

According to the procedures of Steps 2 and 3 in Production Example 1, 0.91 g of the title compound was produced from 1.34 g of ethyl 4-(acetylamino)-3-((2-chloro-4-(ethyloxy)benzyl)amino)benzoate via 1-(2-chloro-4-(ethyloxy)benzyl)-6-ethoxycarbonyl)-22-methylbenzimidazole.

[Properties of the compound]
¹H-NMR(DMSO-$d_6$, δ ppm): 1.27(3H, t, J=6.9 Hz), 2.49 (3H, s), 3.99(2H, q, J=6.9 Hz), 5.52(2H, s), 6.56(1H, d, J=6.4 Hz), 6.81(1H, d, J=6.8 Hz), 7.09(1H, d, J=2.0 Hz), 7.66(1H, brs), 7.78(1H, brs), 7.99(1H, brs), 12.69(1H, brs).

Production Example 12

(Step 1)
<Production of 1-(2-chloro-4-(methyloxy)benzyl)-6-(ethoxycarbonyl)-2-methylbenzimidazole>

According to the procedure of Step 3 in Production Example 6, 0.67 g of the title compound was produced from 0.288 g of an oily substance of 601 sodium hydride, 5 ml of N,N-dimethylformamide, 2.07 g of 1-(2-chloro-4-hydroxybenzyl)-6-(ethoxycarbonyl)-2-methylbenzimidazole, and 1.19 g of methyl iodide.

[Properties of the compound]
¹H-NMR(DMSO-$d_6$, δ ppm): 1.29(3H, t, J=7.1 Hz), 2.52 (3H, s), 3.73(3H, s), 4.27(2H, q, J=7.1 Hz), 5.53(2H, s), 6.63(1H, d, J=8.6 Hz), 6.84(1H, dd, J=8.6 and 2.4 Hz), 7.12(1H, d, J=2.4 Hz), 7.63(1H, d, J=8.4 Hz), 7.79(1H, d, J=8.4 Hz), 7.96(1H, s).

(Step 2)
<Production of 6-carboxy-1-(2-chloro-4-(methyloxy)benzyl)-2-methylbenzimidazole>

According to the procedure of Step 4 in Production Example 6, 0.54 g of the title compound was produced from 0.67 g of 1-(2-chloro-4-(methyloxy)benzyl)-6-(ethoxycarbonyl)-2-methylbenzimidazole.

[Properties of the compound]
$^1$H-NMR(DMSO-d$_6$, δ ppm): 2.52(3H, s), 3.73(3H, s), 5.52(2H, s), 6.59(1H, d, J=8.6 Hz), 6.83(1H, dd, J=2.5 and 8.6 Hz), 7.12(1H, d, J=2.5 Hz), 7.61(1H, d, J=8.4 Hz), 7.78(1H, d, J=8.4 Hz), 7.94(1H, s), 12.75(1H, brs).

Production Example 13

(Step 1)
<Production of 1-(2-chloro-4-((2-methyloxyethyl)oxy)benzyl)-6-(ethoxycarbonyl)-2-methylbenzimidazole>

According to the procedure of Step 3 in Production Example 6, the title compound was produced from 0.093 g of an oily substance of 60% sodium hydride, 5 ml of N,N-dimethylformamide, 0.600 g of 1-(2-chloro-4-hydroxybenzyl)-6-(ethoxycarbonyl)-2-methylbenzimidazole, and 0.431 g of 2-methyloxyethyl bromide.

[Properties of the compound]
$^1$H-NMR(CDCl$_3$, δ ppm): 1.39(3H, t, J=7.1 Hz), 2.56(3H, s), 3.43(3H, s), 3.72(2H, t, J=4.6 Hz), 4.07(2H, t, J=4.6 Hz), 4.38(2H, q, J=7.2 Hz), 5.39(2H, s), 6.37(1H, d, J=8.6 Hz), 6.67(1H, dd, J=8.7 and 2.2 Hz), 7.04(1H, d, J=2.4 Hz), 7.73(1H, d, J=8.4 Hz), 7.93–8.02(2H, m).

(Step 2)
<Production of 6-carboxy-1-(2-chloro-4-((2-methyloxyethyl)oxy)benzyl)-2-methylbenzimidazole>

According to the procedure of Step 4 in Production Example 6, the title compound (0.332 g) was produced from 1-(2-chloro-4-(((2-methyloxyethyl)oxy)benzyl)-6-(ethoxycarbonyl)-2-methylbenzimidazole which was obtained by the above-mentioned procedure.

[Properties of the compound]
$^1$H-NMR(DMSO-d$_6$, δ ppm): 2.49(3H, s), 3.26(3H, s), 3.60(2H, t, J=4.5 Hz), 4.07(2H, t, J=4.5 Hz), 5.52(2H, s), 6.56(1H, d, J=8.8 Hz), 6.44(1H, dd, J=8.6 and 2.6 Hz), 7.13(1H, d, J=2.6 Hz), 7.61(1H, d, J=8.4 Hz), 7.78(1H, dd, J=8.4 and 1.5 Hz), 7.96(1H, d, J=1.3 Hz), 12.67(1H, brs).

Production Example 14

(Step 1)
<Production of 1-(2-chloro-4-(cyclopentylmethyloxy)benzyl)-6-(ethoxycarbonyl)-2-methylbenzimidazole>

According to the procedure of Step 3 in Production Example 6, 0.640 g of the title compound was produced from 0.155 g of an oily substance of 60% sodium hydride, 5 ml of N,N-dimethylformamide, 1.00 g of 1-(2-chloro-4-hydroxybenzyl)-6-(ethoxycarbonyl)-2-methylbenzimidazole, and 0.78 g of ((methanesulfonyloxy)methyl)cyclopentane.

[Properties of the compound]
$^1$H-NMR(CDCl$_3$, δ ppm): 1.29–1.37(2H, m), 1.39(3H, t, J=7.3 Hz), 1.52–1.67(2H, m), 1.78–1.84(2H, m), 2.27–2.37(2H, m), 2.57(3H, s), 3.77(2H, d, J=6.9 Hz), 4.37(2H, q, J=7.2 Hz), 5.38(2H, s), 6.36(1H, d, J=8.8 Hz), 6.62(1H, dd, J=8.5 and 2.4 Hz), 7.00(1H, d, J=2.5 Hz), 7.73(1H, d, J=8.3 Hz), 7.96(1H, d, J=1.1 Hz), 7.98(1H, d, J=8.4 and 1.4 Hz).

(Step 2)
<Production of 6-carboxy-1-(2-chloro-4-(cyclopentylmethyloxy)benzyl)-2-methylbenzimidazole>

According to the procedure of Step 4 in Production Example 6, 0.538 g of the title compound was produced from 0.640 g of 1-(2-chloro-4-(cyclopentylmethyloxy)benzyl)-6-(ethoxycarbonyl)-2-methylbenzimidazole.

[Properties of the compound]
$^1$H-NMR(DMSO-d$_6$, δ ppm): 1.24–1.32(2H, m), 1.47–1.61(4H, m), 1.69–1.77(2H, m), 2.21–2.28(1H, m), 2.52(3H, s), 3.81(2H, d, J=7.0 Hz), 5.51(2H, s), 6.56(1H, d, J=8.7 Hz), 6.82(1H, dd, J=8.6 and 2.4 Hz), 7.10(1H, d, J=2.5 Hz), 7.61(1H, d, J=8.4 Hz), 7.78(1H, d, J=8.4 Hz); 7.94(1H, s), 12.70(1H, brs).

Production Example 15

(Step 1)
<Production of 1-(4-benzyloxy-2-chlorobenzyl)-6-(ethoxycarbonyl)-2-methylbenzimidazole>

According to the procedure of Step 3 in Production Example 6, 1.28 g of the title compound was produced from 0.384 g of an oily substance of 60% sodium hydride, 20 ml of N,N-dimethylformamide, 2.76 g of 1-(2-chloro-4-hydroxybenzyl)-6-(ethoxycarbonyl)-2-methylbenzimidazole, and 1.78 g of benzyl bromide.

[Properties of the compound]
$^1$H-NMR(DMSO-d$_6$, δ ppm): 1.29(3H, t, J=7.1 Hz), 2.52(3H, s), 4.27(2H, q, J=7.1 Hz), 5.08(2H, s), 5.52(2H, s), 6.61(1H, d, J=8.7 Hz), 6.91(1H, d, J=8.7 Hz), 7.21(1H, d, J=2.2 Hz), 7.31(1H, m), 7.37(2H, m), 7.40(2H, m), 7.64(1H, d, J=8.4 Hz), 7.79(1H, dd, J=1.3 and 8.4 Hz), 7.97(1H, s).

(Step 2)
<Production of 1-(4-benzyloxy-2-chlorobenzyl)-6-carboxy-2-methylbenzimidazole>

According to the procedure of Step 4 in Production Example 6, 1.12 g of the title compound was produced from 1.28 g of 1-(4-benzyloxy-2-chlorobenzyl)-6-(ethoxycarbonyl)-2-methylbenzimidazole.

[Properties of the compound]
$^1$H-NMR(DMSO-d$_6$, δ ppm): 2.52(3H, s), 5.08(2H, s), 5.52(2H, s), 6.58(1H, d, J=8.7 Hz), 6.91(1H, dd, J=2.5 and 8.7 Hz), 7.22(1H, d, J=2.5 Hz), 7.31(1H, m), 7.34–7.42(4H, m), 7.61(1H, d, J=8.4 Hz), 7.78(1H, dd, J=1.4 and 8.4 Hz), 7.95(1H, s), 12.69(1H, brs).

Production Example 16

(Steps 1 and 2)
<Production of 1-(2-chloro-4-iodobenzyl)-6-(ethoxycarbonyl)-2-methylbenzimidazole>

According to the procedures of Steps 1 and 2 in Production Example 1, 2.75 g of the title compound was produced from 2.44 g of ethyl 4-(acetylamino)-3-aminobenzoate, 4.53 g of 2-chloro-4-iodobenzyl bromide, and 3.73 g of potassium carbonate via ethyl 4-(acetylamino)-3-((2-chloro-4-iodobenzyl)amino)benzoate.

[Properties of the compound]
$^1$H-NMR(CDCl$_3$, δ ppm): 1.39(3H, t, J=7.2 Hz), 2.56(3H, s), 4.38(2H, q, J=7.2 Hz), 5.38(2H, s), 6.11(1H, d, J=8.2 Hz), 7.42(1H, dd, J=8.2 and 1.5 Hz), 7.75(1H, d, J=8.5 Hz), 7.75(1H, d, J=8.5 Hz), 7.82(1H, d, J=1.6 Hz), 7.96(1H, dd, J=8.4 and 1.4 Hz).

(Step 3)
<Production of 1-(2-chloro-4-(thiophen-2-yl)benzyl)-6-(ethoxycarbonyl)-2-methylbenzimidazole>

1-(2-chloro-4-iodobenzyl)-6-(ethoxycarbonyl)-2-methylbenzimidazole (1.00 g), 0.34 g of thiophen-2-boric acid, 0.06 g of tetrakistriphenylphosphinepalladium (IV), 2.2 ml of 2 M sodium carbonate aqueous solution, 3 ml of toluene, and 1 ml of ethanol were mixed, and the mixture was heat-refluxed for 2.5 hours. The reaction solution was cooled to room temperature, and was diluted with 50 ml of toluene and 50 ml of water. The reaction solution was filtered through Celite, and the filtrate was separated. The organic layer was dried with anhydrous sodium sulfate, and concentrated under reduced pressure. The resulting oil was recrystallized from ethanol/water (15 ml/15 ml) to give 0.60 g of the title compound.

[Properties of the compound]
$^1$H-NMR(DMSO-d$_6$, δ ppm): 1.28(3H, t, J=37.0 Hz), 2.54(3H, s), 4.26(2H, q, J=7.0 Hz), 5.63(2H, s), 6.61(1H, d, J=8.0 Hz), 7.13(1H, d, J=4.0 Hz), 7.49(1H, d, J=8.0 Hz), 7.57(1H, d, J=4.2 Hz), 7.66(1H, d, J=8.4 Hz), 7.81(1H, d, J=8.4 Hz), 7.84(1H, s), 8.01(1H, s).

(Step 4)

<Production of 6-carboxy-1-(2-chloro-4-(thiophen-2-yl)benzyl)-2-methylbenzimidazole>

1-(2-Chloro-4-(thiophen-2-yl)benzyl)-6-(ethoxycarbonyl)-2-methylbenzimidazole (0.60 g), 2 ml of 10% sodium hydroxide aqueous solution, and 5 ml of ethanol were mixed and heat-refluxed for 15 minutes. After cooled to room temperature, insoluble materials were removed by Celite filtration, and the reaction solution was adjusted to a pH of 6 with approximately 4 ml of 1 N hydrochloric acid. The precipitated crystals were filtered, washed with 50% aqueous ethanol, and then dried under reduced pressure to give 0.208 g of the title compound.

[Properties of the compound]

$^1$H-NMR(DMSO-d$_6$, δ ppm): 2.53(3H, s), 5.61(2H, s), 6.56(1H, d, J=8.1 Hz), 7.13(1H, m), 7.50(1H, dd, J=1.8 and 8.1 Hz),7.58(2H, m), 7.61(1H, d, J=8.4 Hz), 7.80(1H, dd, J=1.4 and 8.4 Hz), 7.84(1H, d, J=1.8 Hz), 7.97(1H, s).

Production Example 17

(Step 1)

<Production of 1-(2-chloro-4-(2-furyl)benzyl)-6-(ethoxycarbonyl)-2-methylbenzimidazole>

1-(2-chloro-4-iodobenzyl)-6-(ethoxycarbonyl)-2-methylbenzimidazole (1.00 g), 0.30 g of furan-2-boric acid, 0.06 g of tetrakistriphenylphosphinepalladium (IV), 2.2 ml of 2 M sodium carbonate aqueous solution, 3 ml of toluene, and 1 ml of ethanol were mixed, and the mixture was heat-refluxed for 2.5 hours. The reaction solution was cooled to room temperature, and was diluted and extracted with 50 ml of toluene and 50 ml of water. The organic layer was dried with anhydrous sodium sulfate, and concentrated under reduced pressure. The resulting oil was recrystallized from ethanol/water (20 ml/20 ml) to give 0.73 g of the title compound.

[Properties of the compound]

$^1$H-NMR(DMSO-d$_6$, δ ppm): 1.27(3H, t, J=7.1 Hz), 2.53 (3H, s), 4.26(2H, q, J=7.1 Hz), 5.63(2H, s), 6.59(1H, dd, J=3.3 and 1.8 Hz), 6.65(1H, d, J=8.1 Hz), 7.05(1H, d, J=3.2 Hz), 7.50(1H, d, J=8.1 Hz), 7.65(1H, d, J=8.4 Hz), 7.75(1H,s ), 7.80(1H, d, J=8.4 Hz), 7.86(1H, s), 8.00(1H, s).

(Step 2)

<Production of 6-carboxy-1-(2-chloro-4-(2-furyl)benzyl)-2-methylbenzimidazole>

1-(2-chloro-4-(thiophen-2-yl)benzyl)-6-(ethoxycarbonyl)-2-methylbenzimidazole (0.73 g, 1.85 mmol), 2 ml of 10% sodium hydroxide aqueous solution, and 15 ml of ethanol were mixed and heat-refluxed for 1.5 hours. After cooled to room temperature, the reaction solution was adjusted to a pH of 6 with approximately 6 ml of 1 N hydrochloric acid, and 10 ml of water was added thereto. The precipitated crystals were filtered, washed with 50% aqueous ethanol, and then dried under reduced pressure to give 0.305 g of the title compound.

[Properties of the compound]

$^1$H-NMR(DMSO-d$_6$, δ ppm): 2.53(3H, s), 5.62(2H, s), 6.59(1H, m), 6.62(1H, d, 8.1 Hz), 7.05(1H, d, J=3.3 Hz), 7.54(1H, d, J=8.0 Hz), 7.64(1H, d, J=8.4 Hz), 7.75(1H, s), 7.80(1H, d, J=8.4 Hz), 7.86(1H, s), 7.99(1H, s), 12.70(1H, brs).

Production Example 18

(Step 1)

<Production of 1-(2-chloro-4-(1-pentyn-1-yl)benzyl)-6-(ethoxycarbonyl)-2-methylbenzimidazole>

A solution of 1.75 g of 1-(2-chloro-4-iodobenzyl)-6-(ethoxycarbonyl)-2-methylbenzimidazole, 1.31 g of 1-pentyne, 173 mg of palladium (II) acetate, 404 mg of triphenylphosphine, 220 mg of copper iodide, and 2.14 g of tributylamine in 17.5 ml of N,N-dimethylformamide was heated at 60° C. in a nitrogen atmosphere. After 2 hours, the reaction solution was cooled in, an ice bath, and water was added. The solution was extracted twice with ethyl acetate. The combined organic layer was washed three times with water, and dried with anhydrous magnesium sulfate. After filtration in reduced pressure, the filtrate was concentrated. The residue was purified through flash silica-gel column chromatography (eluent: a mixture of hexane and ethyl acetate at a ratio of 5:1) to give 1.10 g of the title compound as a pale yellow solid.

[Properties of the compound]

$^1$H-NMR (CDCl$_3$, δ ppm): 1.02(3H, t, J=7 Hz), 1.39(3H, t, J=7 Hz), 1.54–1.68(2H, m), 2.36(2H, t, J=7 Hz), 2.56(3H, s), 4.37(2H, q, J=7 Hz), 5.42(2H, s), 6.31(1H, d, J=8 Hz), 7.09(1H, dd, J=8, 1 Hz), 7.49(1H, d, J=1 Hz), 7.75(1H, d, J=8 Hz), 7.92(1H, brs), 7.99(1H, dd, J=8, 1 Hz).

MASS(ESI): m/z 395 (M+1).

(Step 2)

<6-Carboxy-1-(2-chloro-4-(1-pentyn-1-yl)benzyl)-2-methylbenzimidazole>

According to the procedure of Step 4 in Production Example 6, 448 mg of the title compound was produced as a colorless solid from 510 mg of 1-(2-chloro-4-(1-pentyn-1-yl)benzyl)-6-(ethoxycarbonyl)-2-methylbenzimidazole.

[Properties of the compound]

$^1$H-NMR (DMSO-d$_6$, δ ppm): 0.97(3H, t, J=7 Hz), 1.46–1.61(2H, m), 2.39(2H, t, J=7 Hz), 2.51(3H, s), 5.62 (2H, s), 6.47(1H, d, J=8 Hz), 7.25(1H, dd, J=8, 1 Hz), 7.57(1H, d, J=1 Hz), 7.64(1H, d, J=8 Hz), 7.81(1H, dd, J=8, 1 Hz), 7.97(1H, brs).

MASS(ESI): m/z 367 (M+1).

Production Example 19

(Step 1)

<Production of 1-(2-chloro-4-(1-hexyn-1-yl)benzyl)-6-(ethoxycarbonyl)-2-methylbenzimidazole>

According to the procedure of Step 1 in Production Example 19, 3.71 g of the title compound was produced as a pale yellow solid from 5.0 g of 1-(2-chloro-4-iodobenzyl)-6-(ethoxycarbonyl)-2-methylbenzimidazole and 3.75 g of 1-hexyne.

[Properties of the compound]

$^1$H-NMR (CDCl$_3$, δ ppm): 0.93(3H, t, J=7Hz), 1.35–1.64 (7H, m), 2.38(2H, t, J=7Hz), 2.38(2H, t, J=7Hz), 2.55(3H, s), 4.38(2H, q, J=7Hz), 5.42(2H, s), 6.31(1H, d, J=8Hz), 7.09(1H, brd, J=8Hz), 7.49(1H, d, J=1 Hz), 7.75(1H, d, J=8Hz), 7.92(1H, brs), 7.99(1H, dd, J=8, 1 Hz).

MASS(ESI): m/z 409 (M+1).

(Step 2)

<Production of 6-carboxy-1-(2-chloro-4-(1-hexyn-1-yl)benzyl)-2-methylbenzimidazole>

According to the procedure of Step 4 in Production Example 6, 1.53 g of the title compound was produced as colorless crystals from 1.75 g of 1-(2-chloro-4-(1-hexyn-1-yl)benzyl)-6-(ethoxycarbonyl)-2-methylbenzimidazole.

[Properties of the compound]

$^1$H-NMR (DMSO-d$_6$, δ ppm): 0.89(3H, t, J=7 Hz), 1.32–1.57(4H, m), 2.41(2H, t, J=7 Hz), 2.50(3H, s), 5.62 (2H, s), 6.47(1H, d, J=8 Hz), 7.24(1H, dd, J=8, 1 Hz), 7.56(1H, d, J=1 Hz), 7.64(1H, d, J=8 Hz), 7.81(1H, dd, J=8, 1 Hz), 7.97(1H, brs).

MASS(ESI): m/z 381 (M+1).

Production Example 20

(Step 1)

<Production of 1-(2-chloro-4-(1-heptyn-1-yl)benzyl)-6-(ethoxycarbonyl)-2-methylbenzimidazole>

According to the procedure of Step 1 in Production Example 19, 1.46 g of the title compound was produced as a pale yellow solid from 1.75 g of 1-(2-chloro-4-iodobenzyl)-6-(ethoxycarbonyl)-2-methylbenzimidazole and 1.85 g of 1-heptyne.

[Properties of the compound]

$^1$H-NMR (CDCl$_3$, δ ppm): 0.91(3H, t, J=7 Hz), 1.28–1.47 (7H, m), 1.54–1.65(2H, m), 2.37(2H, t, J=7 Hz), 2.58(3H, s), 4.37(2H, q, J=7 Hz), 5.43(2H, s), 6.32(1H, d, J=8 Hz), 7.10(1H, brd, J=8 Hz), 7.50(1H, d, J=1 Hz), 7.78(1H, d, J=8 Hz),7.93(1H, brs), 8.00(1H, dd, J=8, 1 Hz).

MASS(ESI): m/z 423 (M+1)

(Step 2)

<Production of 6-carboxy-1-(2-chloro-4-(1-heptyn-1-yl)benzyl)-2-methylbenzimidazole>

According to the procedure of Step 4 in Production Example 6, 545, mg of the title compound was produced as a colorless solid from 650 mg, of 1-(2-chloro-4-(1-heptyn-1-yl)benzyl)-6-(ethoxycarbonyl)-2-methylbenzimidazole.

[Properties of the compound]

$^1$H-NMR (DMSO-d$_6$, δ ppm): 0.87(3H, t, J=7 Hz), 1.23–1.59(6H, m), 2.40(2H, t, J=7 Hz), 2.50(3H, s), 5.63 (2H, s), 6.47(1H, d, J=8 Hz), 7.24(1H, brd, J=8 Hz), 7.56 (1H, brs), 7.64(1H, d, J=8 Hz), 7.81(1H, brd, J=8 Hz), 7.98(1H, brs).

MASS(ESI): m/z 395 (M+1).

Production Example 21

(Step 1)

<Production of 1-(2-chloro-4-vinylbenzyl)-6-(ethoxycarbonyl)-2-methylbenzimidazole>

1-(4-Bromo-2-chlorobenzyl)-6-(ethoxycarbonyl)-2-methylbenzimidazole (1.43 g), 1.11 g of tributyl(vinyl)tin, and 81.1 mg of tetrakis(triphenylphosphine)palladium (0) was added to a suspension of 357 mg of lithium chloride in 7.9 ml of anhydrous 1,4-dioxane in a nitrogen atmosphere, and the reaction solution was heat-refluxed. The reaction solution was allowed to cool followed by filtration, water was added to the filtrate, and the filtrate was extracted with chloroform. The organic layer was washed with saturated aqueous solution of sodium bicarbonate and saturated brine, and then dried with anhydrous magnesium sulfate. The filtrate was concentrated. The residue was subjected to flash silica-gel column chromatography, and was eluted with a mixture of chloroform and methanol at a ratio of 20:1. Fractions containing the desired compound were concentrated. The resultant crystals were washed with diisopropyl ether and dried to give 720 mg of the title compound as colorless crystals.

[Properties of the compound]

$^1$H-NMR (CDCl$_3$, δ ppm): 1.39 (3H, t, J=7 Hz), 2.57 (3H, s), 4.37 (2H, q, J=7 Hz), 5.32 (1H, d, J=10 Hz), 5.44 (2H, s), 5.75 (1H, d, J=15 Hz), 6.37 (1H, d, J=8 Hz), 6.61 (1H, dd, J=10, 15 Hz), 7.11 (1H, d, J=8 Hz), 7.50 (1H, s), 7.75 (1H, d, J=8 Hz), 7.95 (1H, s), 8.00 (1H, dd, J=1, 8 Hz).

MASS(ESI): m/z 355 (M+1).

(Step 2)

<Production of 1-(2-chloro-4-ethylbenzyl)-6-(ethoxycarbonyl)-2-methylbenzimidazole>

In a hydrogen atmosphere, a mixture of 710 mg of 1-(2-chloro-4-vinylbenzyl)-6-(ethoxycarbonyl)-2-methylbenzimidazole, platinum (IV) oxide, and 24 ml of dioxane was stirred at room temperature for 2 hours. The reaction solution was filtered through Celite to remove solid materials, and the filtrate was concentrated. Isopropyl ether was added to the residue, and the insoluble materials were removed by Celite filtration. The filtrate was concentrated to give 612 mg of the title compound as light yellow crystals.

[Properties of the compound]

$^1$H-NMR (CDCl$_3$, δ ppm): 1.20 (3H, t, J=7 Hz), 1.39 (3H, t, J=7 Hz), 2.57 (3H, s), 2.60 (2H, q, J=7 Hz), 4.37 (2H, q, J=7 Hz), 5.42 (2H, s), 6.32 (1H, d, J=8 Hz), 6.92 (1H, dd, J=1, 8 Hz), 7.30 (1H, brs), 7.74 (1H, d, J=8 Hz), 7.95 (1H, s), 7.99 (1H, dd, J=1, 8 Hz).

MASS(ESI): m/z 357 (M+1).

(Step 3)

<Production of 6-carboxy-1-(2-chloro-4-ethylbenzyl)-2-methylbenzimidazole>

According to the procedure of Step 4 in Production Example 6, 480 mg of the title compound was produced as colorless crystals from 612 mg of 1-(2-chloro-4-ethylbenzyl)-6-(ethoxycarbonyl)-2-methylbenzimidazole.

[Properties of the compound]

$^1$H-NMR (CDCl$_3$, δ ppm): 1.20 (3H, t, J=7 Hz), 2.58–2.65 (5H, m), 5.44 (2H, s), 6.34 (1H, d, J=8 Hz), 6.93 (1H, d, J=8 Hz), 7.31 (1H, s), 7.81 (1H, d, J=8 Hz), 8.02 (1H, s), 8.05 (1H, d, J=8 Hz).

MASS(ESI): m/z 327 (M−1).

Production Example 22

(Step 1)

<Production of 4-n-butyl-1-((t-butyldimethylsilyloxy)methyl)-2-chlorobenzene>

Thirty milliliters of 1.6 N n-butyllithium solution was added to a solution of 14.6 g of 4-bromo-1-((t-butyldimethylsilyloxy)methyl)-2-chlorobenzene in 30 ml of tetrahydrofuran at −60° C., and the reaction solution was stirred at this temperature for 1 hour and then at room temperature for 20 minutes. After the reaction solution was cooled to −60° C., 5.43 g of N-formylpiperidine was added thereto, and the solution was stirred at 0° C. for 30 minutes. Water and diethyl ether were added to the solution, and the separated organic layer was washed with water. The organic layer was concentrated, and purified through silica-gel column chromatography (eluent: a mixture of hexane and ethyl acetate at a ratio of 4:1) to give 7.1 g of the title compound. This compound was used immediately in the subsequent reaction.

(Step 2)

<Production of 4-n-butyl-2-chloro-1-(hydroxymethyl)benzene>

A solution of 7.1 g of 4-n-butyl-1-((t-butyldimethylsilyloxy)methyl)-2-chlorobenzene and 7.8 g of tetrabutylammonium fluoride in 30 ml of tetrahydrofuran was stirred at room temperature for 8 hours. Water and diethyl ether were added to the solution, and separated. The organic layer was washed with water, concentrated, and then purified through silica-gel column chromatography (eluent: a mixture of hexane and ethyl acetate at a ratio of 4:1) to give 3.6 g of the title compound.

[Properties of the compound]

$^1$H-NMR (CDCl$_3$, δ ppm): 0.92(3H, t, J=7.3 Hz), 1.31–1.39(2H, m), 1.55–1.61(2H, m), 1.94(1H, t, J=6.4 Hz), 2.58(2H, t, J=7.7 Hz), 4.74(2H, d, J=6.4 Hz), 7.08(1H, dd, J=7.8 and 1.5 Hz), 7.19(1H, d, J=1.5 Hz), 7.35(1H, d, J=7.8 Hz).

(Step 3)
<Production of 4-n-butyl-2-chloro-1-(chloromethyl) benzene>

Thionyl chloride (3.2 g) was added to 3.6 g of 4-n-butyl-2-chloro-1-(hydroxymethyl)benzene, and the reaction mixture was stirred at room temperature for 1 hour, and then at 50° C. for 20 minutes. Water and chloroform were added to the mixture, and separated. The organic layer was washed with water, and concentrated to give 4.3 g of the title compound.

[Properties of the compound]
$^1$H-NMR (CDCl$_3$, δ ppm): 0.93(3H, t, J=7.4 Hz), 1.31–1.39(2H, m), 1.54–1.61(2H, m), 2.59(2H, t, J=7.7 Hz), 4.68(2H, s), 7.08(1H, dd, J=7.8 and 1.6 Hz), 7.22(1H, d, J=1.4 Hz), 7.35(1H, d, J=7.8 Hz).

(Step 4)
<Production of ethyl 4-(acetylamino)-3-((4-n-butyl-2-chlorobenzyl)amino)benzoate>

According to the procedure of Step 3 in Production Example 1, the title compound was produced from 3.12 g of ethyl 4-(acetylamino)-3-aminobenzoate, 4.25 g of 4-n-butyl-2-chloro-1-(chloromethyl)benzene, 2.70 g of potassium carbonate, and 0.63 g of sodium iodide. This compound was used immediately in the subsequent reaction.

(Step 5)
<Production of 1-(4-n-butyl-2-chlorobenzyl)-6-carboxy-2-methylbenzimidazole>

According to the procedures of Steps 4 and 5 in Production Example 1, 3.00 g of the title compound was produced from 3.70 g of ethyl 4-(acetylamino)-3-((4-n-butyl-2-chlorobenzyl)amino)benzoate obtained in the step above.

[Properties of the compound]
$^1$H-NMR (DMSO-d$_6$, δ ppm): 0.84(3H, t, J=7.4 Hz), 1.21–1.29(2H, m), 1.46–1.53(2H, m), 2.51(3H, s), 2.53(2H, t, J=7.7 Hz), 5.56(2H, s), 6.46(1H, d, J=7.9 Hz), 7.05(1H, d, J=7.9 Hz), 7.37(1H, d, J=1.6 Hz), 7.62(1H, d, J=8.4 Hz), 7.78(1H, dd, J=8.4 and 1.5 Hz), 7.94(1H, d, J=1.2 Hz).

Production Example 23

(Step 1)
<Production of 1-(2-chloro-4-(n-pentyl)benzyl)-6-(ethoxycarbonyl)-2-methylbenzimidazole>

According to the procedure of Step 2 in Production Example 21, 527 mg of the title compound as a colorless solid was produced from 560 mg of 1-(2-chloro-4-(1-pentyn-1-yl)benzyl)-6-(ethoxycarbonyl)-2-methylbenzimidazole.

[Properties of the compound]
$^1$H-NMR (CDCl$_3$, δ ppm): 0.88(3H, t, J=7 Hz), 1.22–1.44 (7H, m), 1.50–1.67(2H, m), 2.50–2.59(5H, m), 4.37(2H, q, J=7 Hz), 5.42(2H, s), 6.31(1H, d, J=8 Hz), 6.89(1H, dd, J=8, 1 Hz), 7.28(1H, d, J=1 Hz), 7.75(1H, d, J=8 Hz), 7.96(1H, brs), 7.99(1H, dd, J=B, 1 Hz).

MASS(ESI): m/z 399 (M+1)

(Step 2)
<Production of 6-carboxy-1-(2-chloro-4-(n-pentyl)benzyl)-2-methylbenzimidazole>

According to the procedure of Step 4 in Production Example 6, 448 mg of the title compound was produced as a colorless solid from 523 mg of 1-(2-chloro-4-(n-pentyl) benzyl)-6-(ethoxycarbonyl)-2-methylbenzimidazole.

[Properties of the compound]
$^1$H-NMR (DMSO-$_6$, δ ppm): 0.84(3H, t, J=7 Hz), 1.16–1.47(4H, m), 1.46–1.60(2H, m), 2.44–2.60(5H, m), 5.58(2H, s), 6.47(1H, d, J=8 Hz), 7.06(1H, brd, J=8 Hz), 7.39(1H, s), 7.63(1H, d, J=8 Hz), 7.80(1H, dd, J=8, 1 Hz), 7.95(1H, s).

MASS(ESI): m/z 371 (M+1).

Production Example 24

(Step 1)
<Production of 1-(2-chloro-4-(n-hexyl)benzyl)-6-(ethoxycarbonyl)-2-methylbenzimidazole>

According to the procedure of Step 2 in Production Example 21, 1.81 g of the title compound as a light brown solid was produced from 1.86 g of 1-(2-chloro-4-(1-hexyn-1-yl)benzyl)-6-(ethoxycarbonyl)-2-methylbenzimidazole.

[Properties of the compound]
$^1$H-NMR (CDCl$_3$, δ ppm): 0.87(3H, brt, J=7 Hz), 1.21–1.35(6H, m), 1.39(3H, t, J=7 Hz), 1.50–1.63(2H, m), 2.50–2.60(5H, m), 4.37(2H, q, J=7 Hz),5.42(2H, s), 6.31 (1H, d, J=8 Hz), 6.88(1H, brd, J=8 Hz), 7.28(1H, brs), 7.74(1H, d, 0J=8 Hz), 7.96(1H, brs), 7.99(1H, dd, J=8, 1 Hz).

MASS(ESI): m/z 413 (M+1).

(Step 2)
<Production of 6-carboxy-1-(2-chloro-4-(n-hexyl)benzyl)-2-methylbenzimidazole>

According to the procedure of Step 4 in Production Example 6, 1.48 g of the title compound was produced as a colorless solid from 1.79 g of 1-(2-chloro-4-(n-hexyl) benzyl)-6-(ethoxycarbonyl)-2-methylbenzimidazole.

[Properties of the compound]
$^1$H-NMR (DMSO-d$_6$, δ ppm): 0.87(3H, brt, J=7 Hz), 1.15–1.32(6H, m), 1.43–1.59(2H, m), 2.45–2.59(5H, m), 5.58(2H, s), 6.46(1H, d, J=8 Hz), 7.06(1H, brd, J=8 Hz), 7.39(1H, brs), 7.63(1H, d, J=8 Hz), 7.80(1H, dd, J=8, 1 Hz), 7.96(1H, brs).

MASS(ESI): m/z 385 (M+1).

Production Example 25

(Step 1)
<Production of 1-(2-chloro-4-(n-heptyl)benzyl)-6-(ethoxycarbonyl)-2-methylbenzimidazole>

According to the procedure of Step 2 in Production Example 21, 700 mg of the title compound as a pale yellow solid was produced from 744 mg of 1-(2-chloro-4-(1-heptyn-1-yl)benzyl)-6-(ethoxycarbonyl)-2-methylbenzimidazole.

[Properties of the compound]
$^1$H-NMR (CDCl$_3$, δ ppm): 0.85(3H, brt, J=7 Hz), 1.17–1.35(8H, m), 1.39(3H, t, J=7 Hz), 1.49–1.63(2H, m), 2.50–2.61(5H, m), 4.37(2H, q, J=7 Hz), 5.42(2H, s), 6.31 (1H, d, J=8 Hz), 6.88(1H, brd, J=8 Hz), 7.28(1H, brs), 7.74(1H, d, J=8 Hz), 7.96(1H, brs), 7.99(1H, dd, J=8, 1 Hz).

MASS(ESI): m/z 427 (M+1).

(Step 2)
<Production of 6-carboxy-1-(2-chloro-4-(n-heptyl)benzyl)-2-methylbenzimidazole>

According to the procedure of Step 4 in Production Example 6, 573 mg of the title compound was produced as colorless crystals from 653 mg of 1-(2-chloro-4-(n-heptyl) benzyl)-6-(ethoxycarbonyl)-2-methylbenzimidazole.

[Properties of the compound]
$^1$H-NMR (CDCl$_3$, δ ppm): 0.87 (3H, t, J=7 Hz), 1.18–1.37 (8H, m), 1.48–1.63 (2H, m), 2.55 (2H, t, J=7 Hz), 2.61 (3H, s), 5.43 (2H, s), 6.33 (1H, d, J=8 Hz), 6.90 (1H, d, J=8 Hz), 7.29 (1H, s), 7.82 (1H, d, J=8 Hz), 8.01–8.10 (2H, m).

MASS(ESI): m/z 397 (M−1).

Production Example 26

(Step 1)
<Production of 2-chloro-4-(trifluoromethyl)toluene>

2-Chloro-4-iodotoluene (22.0 g) was dissolved in 110 ml of N,N-dimethylformamide. Copper (I) iodide (49.8 g), 37.8 g of ethyl chlorodifluoroacetate, and 15.2 g of potassium fluoride were added thereto, and the reaction solution was stirred at 116° C. for 70 hours. After Celite filtration of the reaction solution, 11 ml of water and 110 ml of diethyl ether were added to the filtrate while being cooled with ice, and the solution was stirred. The solution was filtered through Celite. The product was extracted from the filtrate with 110 ml of diethyl ether. The organic layer was washed with 110 ml of saturated brine, dried with anhydrous magnesium sulfate, and then concentrated under reduced pressure to give 23.0 g of the title compound as a brown oily substance.

[Properties of the compound]
$^1$H-NMR(CDCl$_3$, δ ppm): 2.43(3H, s), 7.34(1H, d, J=8 Hz), 7.42(1H, d, J=8 Hz), 7.60(1H, s).

(Step 2)
<Production of 1-(bromomethyl)-2-chloro-4-(trifluoromethyl)benzene>

2-Chloro-4-(trifluoromethyl)toluene (10.0 g) was dissolved in 50 ml of carbon tetrachloride, and 18.3 g of N-bromosuccinimide and 2.38 g of 2,2'-azobis(4-methoxy-2,4-dimethylvaleronitrile were added thereto. The reaction solution was stirred at 75° C. for 5 hours, 50 ml of hexane was added thereto, and the solution was stirred for 1 hour while being ice cooled. The reaction solution was filtered, and the filtrate was concentrated under reduced pressure. Then, the residue was dissolved in 50 ml of ethyl acetate, and washed with 50 ml of saturated aqueous solution of sodium bicarbonate and subsequenetly 50 ml of saturated brine. The organic layer was dried with anhydrous magnesium sulfate and concentrated under reduced pressure. The residue was subjected to silica-gel column chromatography and eluted with hexane. Fractions containing the desired compound were collected and concentrated under reduced pressure to give 6.20 g of the title compound as a pale yellow oily substance.

[Properties of the compound]
$^1$H-NMR(CDCl$_3$, δ ppm): 4.59(2H, s), 7.52(1H, d, J=8 Hz), 7.57(1H, d, J=8 Hz), 7.67(1H, s).

(Step 3)
<Production of ethyl 4-(acetylamino)-3-((2-chloro-4-(trifluoromethyl)benzyl)amino)benzoate>

Ethyl 4-(acetylamino)-3-aminobenzoate (500 mg) was dissolved in 5 ml of N,N-dimethylformamide. Potassium carbonate (497 mg) and subsequently 101 mg of sodium iodide were added thereto while being cooled with ice. Then, 1.05 g of 1-(bromomethyl)-2-chloro-4-(trifluoromethyl) benzene was added dropwise thereto over a period of 10 minutes while being cooled with ice. After the reaction solution was stirred at 80° C. for 6 hours, 30 ml of water was added thereto under ice-cooled conditions, and the precipitated crystals were collected through filtration. The crystals were suspended in 10 ml of diisopropyl ether and heated. The solution was allowed to cool. The precipitated crystals were collected through filtration, and were dried under reduced pressure while being heated to give 706 mg of the title compound as colorless crystals.

[Properties of the compound]
$^1$H-NMR(CDCl$_3$, δ ppm): 1.34(3H, t, J=7 Hz), 2.45(3H, s), 4.31(2H, q, J=7 Hz), 4.52–4.60(3H, m), 7.33(1H, s), 7.37–7.40(2H, m), 7.45–7.55(3H, m), 7.67(1H, s).

(Steps 4 and 5)
<Production of 6-carboxy-1-(2-chloro-4-(trifluoromethyl) benzyl)-2-methylbenzimidazole>

According to the procedure of Step 5 in Production Example 29 followed by the procedure of Step 5 in Production Example 1, 777 mg of the title compound was produced as colorless crystals from 910 mg of ethyl 4-(acetylamino)-3-((2-chloro-4-(trifluoromethyl)benzyl)aminobenzoate.

[Properties of the compound]
$^1$H-NMR(DMSO-d$_6$, δ ppm): 2.51(3H, s), 5.71(2H, s), 6.63(1H, d, J=8 Hz), 7.63(2H, t, J=8 Hz), 7.82(1H, d, J=8 Hz), 8.01(2H, s).

Production Example 27
(Steps 1 and 2)
<Production of 1-(2-chloro-4-nitrobenzyl)-6-(ethoxycarbonyl)-2-methylbenzimidazole>

According to the procedures of Steps 3 and 4 in Production Example 1, 0.50 g of the title compound was produced from 1.11 g of ethyl 4-(acetylamino)-3-aminobenzoate, 1.29 g of 2-chloro-4-nitrobenzyl chloride, 1.38 g of potassium carbonate, and sodium iodide. This compound was used immediately in the subsequent reaction.

(Step 3)
<Production of 1-(4-amino-2-chlorobenzyl)-6-(ethoxycarbonyl)-2-methylbenzimidazole>

1-(2-Chloro-4-nitrobenzyl)-6-(ethoxycarbonyl)-2-methylbenzimidazole (1.40 g) was suspended in 14.0 ml of ethanol. Acetic acid (4.05 g) and 1.26 g of reduced iron were added thereto, and the reaction solution was heat-refluxed for 3 hours. After the reaction solution was allowed to cool, 20 ml of chloroform was added thereto, and the solution was filtered through Celite. After the filtrate was concentrated under reduced pressure, and diluted with ethyl acetate, a saturated aqueous solution of sodium bicarbonate was added to the solution until the aqueous layer changed to alkaline. The insoluble materials were removed by Celite filtration, and the filtrate was separated. The organic layer was washed with saturated aqueous solution of sodium bicarbonate and subsequently with saturated brine, dried with anhydrous magnesium sulfate, and then concentrated under reduced pressure. Ten milliliters of methanol were added to the residue, the solution was heated and allowed to cool, and the crystals precipitated were collected through filtration to give 630 mg of the title compound as colorless crystals.

[Properties of the compound]
$^1$H-NMR(CDCl$_3$, δ ppm): 1.40(3H, t, J=7 Hz), 2.57(3H, s), 3.56(2H, s), 4.38(2H, q, J=7 Hz), 5.34(2H, s), 6.27(1H, d, J=8 Hz), 6.38(1H, dd, J=8, 2 Hz), 6.76(1H, d, J=2 Hz), 7.72(1H, d, J=8 Hz), 7.95–7.98(2H, m).

(Step 4)
<Production of 1-(2-chloro-4-(N-1-pentylamino)benzyl)-6-(ethoxycarbonyl)-2-methylbenzimidazole>

1-(4-Amino-2-chlorobenzyl)-6-(ethoxycarbonyl)-2-methylbenzimidazole (600 mg) was suspended in 6 ml of methanol. Valeraldehyde (180 mg), 132 mg of sodium cyanoborohydride, and 126 mg of acetic acid were added thereto, and the reaction solution was stirred at room temperature for 12 hours. The reaction solution was concentrated under reduced pressure, and the residue was dissolved in a mixture of chloroform and methanol at a ratio of 4:1. This solution was washed with saturated aqueous solution of sodium bicarbonate and subsequently with saturated brine, dried with anhydrous magnesium sulfate, and then concentrated under reduced pressure. The residue was subjected to silica-gel column chromatography, eluted with a mixture of chloroform and ethyl acetate at a ratio of 5:1. Fractions containing the desired compound were concentrated under reduced pressure to give 692 mg of the title compound as colorless crystals.

[Properties of the compound]
$^1$H-NMR(CDCl$_3$, δ ppm): 0.91(3H, t, J=7 Hz), 1.25–1.44 (7H, m), 1.55–1.65(2H, m), 2.58(3H, s), 3.04(2H, q, J=7 Hz), 3.73(1H, br), 4.37(2H, q, J=7 Hz), 5.35(2H, s), 6.30 (2H, s), 6.64(1H, s), 7.72(1H, d, J=8 Hz), 7.96–7.99(2H, m).

(Step 5)
<Production of 1-(2-chloro-4-(N-methyl-N-(1-pentyl)amino)benzyl)-6-(ethoxycarbonyl)-2-methylbenzimidazole>

In the same manner as in the previous step, 420 mg of the title compound was produced as a colorless oily substance from 674 mg of 1-(2-chloro-4-(N-1-pentylamino)benzyl)-6-(ethoxycarbonyl)-2-methylbenzimidazole and 661 mg of 37% aqueous solution of formaldehyde.

[Properties of the compound]
$^1$H-NMR(CDCl$_3$, δ ppm): 0.89(3H, t, J=7 Hz), 1.23–1.35 (4H, m), 1.40(3H, t, J=7 Hz), 1.45–1.58(2H, m), 2.58(3H, s), 2.89(3H, s), 3.24(2H, t, J=7 Hz), 4.38(2H, q, J=7 Hz), 5.36(2H, s), 6.36(2H, s), 6.69(1H, d, J=2 Hz), 7.72(1H, d, J=8 Hz), 7.96–8.01(2H, m).

(Step 6)
<Production of 6-carboxy-1-(2-chloro-4-(N-methyl-N-(1-pentyl)amino)benzyl)-2-methylbenzimidazole>

According to the procedure of Step 4 in Production Example 6, 309 mg of the title compound was produced as colorless crystals from 400 mg of 1-(2-chloro-4-(N-methyl-N-(1-pentyl)amino)benzyl)-6-(ethoxycarbonyl)-2-methylbenzimidazole.

[Properties of the compound]
$^1$H-NMR (CDCl$_3$, δ ppm): 0.88 (3H, t, J=7 Hz), 1.19–1.38 (4H, m), 1.45–1.60 (2H, m), 2.62 (3H, s), 2.88 (3H, s), 3.24 (2H, t, J=7 Hz), 5.38 (2H, s), 6.37 (2H, s), 6.69 (1H, s), 7.79 (1H, d, J=8 Hz), 8.00–8.10 (2H, m).
MASS(ESI): m/z 398 (M−1).

Production Example 28

(Step 1)
<Production of 1-(4-(N-1-butyrylamino)-2-chlorobenzyl)-6-(ethoxycarbonyl)-2-methylbenzimidazole>

1-(4-Amino-2-chlorobenzyl)-6-(ethoxycarbonyl)-2-methylbenzimidazole (600 mg) and 265 mg of triethylamine were dissolved in 6 ml of dichloromethane. n-Butyryl chloride (231 mg) was added thereto while being cooled with ice, and the reaction solution was stirred at room temperature for 2 hours. Thirty milliliters of hexane was added to the reaction solution, and the crystals precipitated were collected through filtration to give 594 mg of the title compound as colorless crystals.

[Properties of the compound]
$^1$H-NMR(CDCl$_3$, δ ppm): 0.99(3H, t, J=7 Hz), 1.40(3H, t, J=7 Hz), 1.68–1.80(2H, m), 2.35(2H, t, J=7 Hz), 2.56(3H, s), 4.37(2H, q, J=7 Hz), 5.41(2H, s), 6.34(1H, d, J=8 Hz), 7.10(1H, dd, J=8, 2 Hz), 7.74(2H, d, J=8 Hz), 7.94(1H, s), 7.96–8.01(2H, m).

(Step 2)
<Production of 6-carboxy-1-(4-(N-1-butyrylamino)-2-chlorobenzyl)-2-methylbenzimidazole>

According to the procedure of Step 4 in Production Example 6, 402 mg of the title compound was produced as colorless crystals from 730 mg of 1-(4-(N-1-butyrylamino)-2-chlorobenzyl)-6-(ethoxycarbonyl)-2-methylbenzimidazole.

[Properties of the compound]
$^1$H-NMR(DMSO-d$_6$, δ ppm): 0.89(3H, t, J=7 Hz), 1.52–1.65(2H, m), 2.27(2H, t, J=7 Hz), 2.55(3H, s), 5.57 (2H, s), 6.63(1H, d, J=8 Hz), 7.30(1H, dd, J=8, 2 Hz), 7.65(1H, d, J=8 Hz), 7.82(1H, d, J=8 Hz), 7.98(2H, s), 10.11(1H, s).

Production Example 29

(Step 1)
<Production of methyl 2-chloro-4-(methylthio)benzoate>
Sodium thiomethoxide (459 mg) was added to a solution of 1.25 g of methyl 4-bromo-2-chlorobenzoate in 10 ml of N,N-dimethylformamide while being cooled with ice, and the reaction solution was stirred for 2 hours. Hydrochloric acid (1 N) was added to the reaction solution, and the product was extracted with ether three times. The combined organic layer was washed with water and subsequently with saturated brine, and dried with anhydrous magnesium sulfate. The solvent was distilled off, and the residue was purified through silica-gel column chromatography (eluent: a mixture of hexane and ethyl acetate at a ratio of 10:1) to give 835 mg of the title compound as a colorless oily substance.

[Properties of the compound]
$^1$H-NMR(CDCl$_3$, δ ppm): 2.49(3H, s), 3.90(3H, s), 7.11 (1H, d, J=8 Hz), 7.23(1H, s), 7.78(1H, d, J=8 Hz).

(Step 2)
<Production of 2-chloro-4-(methylthio)benzyl alcohol>
While being cooled with ice, 806 mg of methyl 2-chloro-4-(methylthio)benzoate was added dropwise to a suspension of 139 mg of lithium aluminum hydride in 8 ml of tetrahydrofuran, and stirred for 1 hour. After the reaction solution was diluted with ether, 10 ml of 1 N hydrochloric acid was added dropwise thereto, and the product was extracted 3 times with ether. The combined organic layer was washed with saturated solution of sodium bicarbonate and subsequently with saturated brine, and dried with anhydrous magnesium sulfate. The solvent was distilled off to give 725 mg of the title compound as a colorless oily substance.

[Properties of the compound]
$^1$H-NMR(CDCl$_3$, δ ppm: 1.92(1H, brt, J=7 Hz), 2.48(3H, s), 4.73(2H, d, J=7 Hz), 7.15(1H, d, J=8 Hz), 7.23(1H, s), 7.37(1H, d, J=8 Hz).

(Step 3)
<Production of 2-chloro-1-((methanesulfonyloxy)methyl)-4-(methylthio)benzene>

Triethylamine (0.66 ml) was added to a solution of 687 mg of 2-chloro-4-(methylthio)benzyl alcohol in 7 ml of dichloromethane. After 0.31 ml of methanesulfonyl chloride was added dropwise thereto while being cooled with ice, the reaction mixture was stirred for 1.5 hours. The reaction mixture was diluted with chloroform, washed with water, saturated solution of sodium bicarbonate, and saturated brine in this order, and dried with magnesium sulfate. The solvent was distilled off to give 1.02 g of the title compound as a colorless oily substance.

[Properties of the compound]
$^1$H-NMR (CDCl$_3$, δ ppm): 2.48(3H, s), 3.00(3H, s), 5.30(2H, s), 7.15(1H, dd, J=8 and 2 Hz), 7.26(1H, d, J=2 Hz), 7.38(1H, d, J=8 Hz).

(Step 4)
<Production of ethyl 4-(acetylamino)-3-((2-chloro-4-(methylthio)benzyl)amino)benzoate>

Potassium carbonate (579 mg), a solution of 895 mg of 2-chloro-1-((methanesulfonyloxy)methyl)-4-(methylthio) benzene in 3 ml of N,N-dimethylformamide, and 157 mg of sodium iodide were added to a solution of 776 mg of ethyl 4-(acetylamino)-3-aminobenzoate in 6 ml of anhydrous N,N-dimethylformamide while being cooled with ice. After stirred at room temperature for 5 minutes, the reaction solution was heated to 80° C. and stirred for 8 hours. The reaction solution was cooled with ice, 30 ml of water was added thereto, and the crystals precipitated were collected through filtration. These crystals were suspended in hexane and the suspension was heated and stirred at room temperature for 1 hour. The crystals precipitated were subjected to flash silica-gel column chromatography (30 g silica-gel), and eluted with chloroform to give, 1.05 g of the title compound as a yellow amorphous material.

[Properties of the compound]
$^1$H-NMR (CDCl$_3$, δ ppm): 1.37 (3H, t, J=7 Hz), 2.21 (3H, s), 2.48 (3H, s), 4.33 (2H, q, J=7 Hz), 4.39 (2H, s), 7.09 (1H, dd, J=1, 8 Hz), 7.27–7.30 (2H, m), 7.42 (1H, s), 7.50 (2H, s).

MASS(ESI): m/z 393 (M+1).

(Step 5)

<Production of 1-(2-chloro-4-(methylthio)benzyl)-6-(ethoxycarbonyl)-2-methylbenzimidazole>

Concentrated hydrochloric acid (1.5 equivalents) was added to a suspension of 1.00 g of ethyl 4-(acetylamino)-3-((2-chloro-4-(methylthio)benzyl)amino)benzoate in 8.1 ml of ethanol, and the reaction solution was heat-refluxed. The reaction solution was neutralized with a solution of sodium hydroxide, and the crystals precipitated were collected through filtration to give 1.12 g of the title compound as colorless crystals.

[Properties of the compound]
$^1$H-NMR (CDCl$_3$, δ ppm): 1.40 (3H, t, J=7 Hz), 2.45 (3H, s), 2.57 (3H, s), 4.38 (2H, q, J=7 Hz), 5.41 (2H, s), 6.32 (1H, d, J=8 Hz), 6.94 (1H, dd, J=1, 8 Hz), 7.31 (1H, d, J=1 Hz), 7.74 (1H, d, J=8 Hz), 7.94 (1H, s), 7.99 (1H, d, J=8 Hz).

MASS(ESI): m/z 375 (M+1).

(Step 6)

<6-Carboxy-1-(2-chloro-4-(methylthio)benzyl)-2-methylbenzimidazole>

According to the procedure of Step 4 in Production Example 6, 706 mg of the title compound was produced as colorless crystals from 1.1 g of 1-(2-chloro-4-(methylthio)benzyl)-6-(ethoxycarbonyl)-2-methylbenzimidazole.

[Properties of the compound]
$^1$H-NMR (DMSO-d$_6$, δ ppm): 2.47 (3H, s), 2.53 (3H, s), 5.57 (2H, s), 6.49 (1H, d, J=8Hz), 7.13 (1H, dd, J=1, 8Hz), 7.41 (1H, d, 1 Hz), 7.63 (1H, d, J=8 Hz), 7.80 (1H, dd, J=1, 8 Hz), 7.96 (1H, s).

MASS(ESI): m/z 345 (M−1).

Production Example 30

(Step 1)

<Production of ethyl 3-((methyloxyacetyl)amino)-4-nitrobenzoate>

A solution of 15.0 g of ethyl 3-amino-4-nitrobenzoate and 15.0 g of methyloxyacetyl chloride in 150 ml of N,N-dimethylaniline was stirred at 50° C. for 3 hours. After water and ethyl acetate were added thereto and the solution was separated, the organic layer was washed with water. After concentration of the organic layer, diethyl ether and hexane were added thereto to give 18.7 g of the title compound.

[Properties of the compound]
$^1$H-NMR (CDCl$_3$, δ ppm): 1.42 (3H, t, J=7.3 Hz), 3.58 (3H, s), 4.43(2H, q, J=7.2 Hz), 7.85(1H, dd, J=8.7 and 1.6 Hz), 8.27(1H, d, 8.7 Hz), 9.44(1H, d, J=1.7 Hz), 11.15(1H, brs).

(Steps 2 and 3)

<Production of 1-(2-chloro-4-phenylbenzyl)-6-(ethoxycarbonyl)-2-(methyloxymethyl)benzimidazole>

An oily substance of 60% sodium hydride (0.850 g) was added to a solution of 4.00 g of ethyl 3-((methyloxyacetyl)amino)-4-nitrobenzoate in 30 ml of N,N-dimethylformamide, and the reaction solution was stirred at room temperature for 30 minutes. A solution of 5.989 g of 2-chloro-4-phenylbenzyl chloride in 20 ml of N,N-dimethylformamide was added thereto at room temperature, and the solution was stirred over night. Hydrochloric acid (10%) and ethyl acetate were added thereto, and the reaction solution was stirred. The organic layer was separated, washed with water, dried, and concentrated. The residue was purified through silica-gel column chromatography (eluent: a mixture of hexane and ethyl acetate at a ratio of 3:1) to give 4.05 g of a crude product of ethyl 3-(N-2-chloro-4-phenylbenzyl)-(methyloxyacetyl)amino)-4-nitrobenzoate. Further, this product was dissolved in 45 ml of ethanol and 24 ml of acetic acid, 4.68 g of reduced iron was added thereto, and the mixture was stirred at 100° C. for 1.5 hours. The reaction solution was allowed to cool, and filtered through Celite. The filtrate was concentrated, and stirred with ethyl acetate and diluted hydrochloric acid. The organic layer was separated, and washed with saturated aqueous solution of sodium bicarbonate and subsequently with water. The organic layer was concentrated to give 3.50 g of the title compound. This compound was used immediately in the subsequent reaction.

(Step 4)

<Production of 6-carboxy-1-(2-chloro-4-phenylbenzyl)-2-(methyloxymethyl)benzimidazole>

According to the procedure of Step 4 in Production Example 6, 2.84 g of the title compound was produced from 3.50 g of 1-(2-chloro-4-phenylbenzyl)-6-(ethoxycarbonyl)-2-(methyloxymethyl)benzimidazole.

[Properties of the compound]
$^1$H-NMR (DMSO-d$_6$, δ ppm): 3.27(3H, s), 4.72(2H, s), 5.73(2H, s), 6.60(1H, d, J=8.2 Hz), 7.35–7.39(1H, m), 7.41–7.76(2H, m), 7.52(1H, dd, J=8.1 and 1.8 Hz), 7.65–7.67(2H, m), 7.76(1H, d, J=8.4 Hz), 7.83–7.87(2H, m), 8.02(1H, d, J=1.3 Hz), 12.87(1H, brs).

Production Example 31

<Production of N-(4-methylbenzene)sulfamide>

Formic acid (5.87 g) was added dropwise to a solution of 18.0 g of chlorosulfonyl isocyanate in 100 ml of benzene in an ice bath, and the reaction solution was stirred at room temperature for 66 hours, and at 40° C. for 9 hours. The reaction solution was cooled, and while being cooled with ice, 23.3 g of 4-methylaniline and subsequently 128 ml of 1 N sodium hydroxide aqueous solution were added. The solution was stirred for 2 hours. The crystals precipitated were collected through filtration, and recrystallized from 300 ml of water. The crystals precipitated were collected through filtration, washed with water, and dried to give 12.4 g of the title compound.

[Properties of the compound]
$^1$H-NMR (CDCl$_3$, δ ppm): 2.33(3H, s), 4.66(2H, brs), 6.38(1H, brs), 7.14(2H, d, J=7 Hz), 7.17(2H, d, J=7 Hz).

Production Example 32

<Production of N-1-butylsulfamide>

A mixture of 1.92 g of sulfamide, 1.74 g of n-butylamine, and 20 ml of water was refluxed for 5 hours. The reaction solution was cooled to room temperature, and acidified with 3 N hydrochloric acid. This solution was allowed to stand at 0 to 5° C. The crystals precipitated were collected through filtration, washed with water, and dried to give 1.50 g of the title compound.

[Properties of the compound]
$^1$H-NMR (CDCl$_3$, δ ppm): 0.94(3H, t, J=7.4 Hz), 1.35–1.42(2H, m), 1.53–1.60(2H, m), 3.12(2H, t, J=7.1 Hz), 4.53(1H, brs), 4.74(2H, brs).

Production Example 32–2 to Production Example 32–6

In the same manner as in Production Example 31, the following sulfamides were produced. When the product could not be obtained as crystals, the compound was extracted with chloroform and the extract was concentrated to give the desired sulfamide.

<Production of N-ethylsulfamide>
[Properties of the compound]
$^1$H-NMR (CDCl$_3$, δ ppm): 1.23(3H, t, J=7 Hz), 3.18(2H, q, J=7 Hz), 4.54(1H, brs), 4.77(2H, brs).

<Production of N-1-propylsulfamide>
[Properties of the compound]
$^1$H-NMR (CDCl$_3$-CD$_3$OD, δ ppm): 0.96(3H, t, J=7 Hz), 1.60(2H, m), 3.03(2H, t, J=7 Hz).

<Production of N-1-pentylsulfamide>
[Properties of the compound]
$^1$H-NMR (CDCl$_3$, δ ppm): 0.91(3H, t, J=7 Hz), 1.34(4H, m), 1.58(2H, m), 3.13(2H, t, J=7 Hz), 4.36(1H, brs), 4.57 (2H, brs).

<Production of N-1-hexylsulfamide>
[Properties of the compound]
$^1$H-NMR (CDCl$_3$, δ ppm): 0.89(3H, t, J=6.9 Hz), 1.28–1.40(6H, m), 1.59–1.61(2H, m), 3.12(2H, t, J=7.2 Hz), 4.45(3H, brs).

<Production of N-benzylsulfamide>
[Properties of the compound]
$^1$H-NMR (DMSO-d$_6$, δ ppm): 4.06(2H, d, J=6.5 Hz), 6.60(2H, s), 7.02(1H, t, J=6.6 Hz), 7.23(1H, t, J=6.5 Hz), 7.29–7.35(4H, m).

EXAMPLE 1

<Synthesis of 1-(2,4-dichlorobenzyl)-2-methyl-6-((3-methylbenzene)sulfonylcarbamoyl)benzimidazole (1)>

N,N'-Carbonyldiimidazole (0.13 g) was added to a solution of 0.20 g of 6-carboxy-1-(2,4-dichlorobenzyl)-2-methylbenzimidazole in 5 ml of N,N-dimethylformamide, and the reaction solution was stirred at room temperature for 1 hour. 3-Methylbenzenesulfonamide (0.13 g) and 0.12 g of 1,8-diazabicyclo[5.4.0]undec-7-ene were added thereto, and the solution was stirred at 100° C. over night. After the solvent was distilled off under reduced pressure, the residue was diluted with a mixture of methanol and water at a ratio of 2:1, and the solution was adjusted to a pH of 5 with 10% hydrochloric acid. The crystals precipitated were collected through filtration and dried to give 0.23 g of the title compound as white crystals.

[Properties of Compound (1)]
$^1$H-NMR(DMSO-d$_6$, δ ppm): 2.38(3H, s), 2.47(3H, s), 5.57(2H, s), 6.40(1H, d, J=8.3 Hz), 7.30(1H, dd, J=2.2 and 8.4 Hz), 7.48–7.51(2H, m), 7.63(1H, d, J=8.5 Hz), 7.71–7.78(4H, m), 8.05(1H, s), 12.34(1H, brs).
mp: 235.5–239.5° C.

EXAMPLE 2

<Synthesis of 1-((1-bromonaphthalen-2-yl)methyl)-2-methyl-6-((4-methylbenzene)sulfonylcarbamoyl) benzimidazole (2)>

In the same manner as in Example 1, 0.20 g of the title compound were formed as white crystals from 0.20 g of 1-((1-bromonaphthalen-2-yl)methyl)-6-carboxy-2-methylbenzimidazole and 0.11 g of 4-methylbenzenesulfonamide.

[Properties of Compound (2)]
$^1$H-NMR(DMSO-d$_6$, δ ppm): 2.35(3H, s), 5.79(2H, s), 6.46(1H, d, J=8.5 Hz), 7.37(2H, d, J=8.3 Hz), 7.61–7.67(2H, m), 7.70–7.76(2H, m), 7.81–7.86(3H, m), 7.94(1H, d, J=8.0 Hz), 8.09(1H, s), 8.30(1H, d, J=8.7 Hz), 12.29(1H, brs).
IR(Nujol): 1689 cm$^{-1}$.
mp: 268.5–272.5° C.

EXAMPLE 3

<Synthesis of 6-(1-butanesulfonylcarbamoyl)-1-(4-bromo-2-chlorobenzyl)-2-methylbenzimidazole (3)>

In the same manner as in Example 1, 0.19 g of the title compound were formed from 0.20 g of 1-(4-bromo-2-chlorobenzyl)-6-carboxy-2-methylbenzimidazole and 0.09 g of 1-butanesulfonamide.

[Properties of Compound (3)]
$^1$H-NMR(DMSO-d$_6$, δ ppm): 0.85(3H, t, J=7.4 Hz), 1.35–1.43(2H, m), 1.62–1.69(2H, m), 2.48(3H, s), 3.50(2H, t, J=7.8 Hz), 5.56(2H, s), 6.36(1H, d, J=8.4 Hz), 7.44(1H, dd, J=8.3 and 1.5 Hz), 7.67(1H, d, J=8.4 Hz), 7.80(1H, d, J=8.4 Hz), 7.86(1H, d, J=1.5 Hz), 8.09(1H, s), 11.86(1H, brs).
IR(Nujol): 1672 cm$^{-1}$.
mp: 218.7–220.3° C.

EXAMPLE 4

<Synthesis of 1-(4-bromo-2-chlorobenzyl)-2-methyl-6-((3-methylbenzene)sulfonylcarbamoyl)benzimidazole (4)>

In the same manner as in Example 1, 0.17 g of the title compound were formed from 0.20 g of 1-(4-bromo-2-chlorobenzyl)-6-carboxy-2-methylbenzimidazole and 0.12 g of (3-methylbenzene)sulfonamide.

[Properties of Compound (4)]
$^1$H-NMR(DMSO-d$_6$, δ ppm): 2.38(3H, s), 2.46(3H, s), 5.55(2H, s), 6.32(1H, d, J=8.4 Hz), 7.42(1H, dd, J=8.1 and 1.8 Hz), 7.49–7.51(2H, m), 7.63(1H, d, J=8.5 Hz), 7.71–7.73(1H, m), 7.75–7.78(2H, m), 7.84(1H, d, J=2.0 Hz), 8.05(1H, d, J=1.4 Hz), 12.34(1H, brs).
mp: 250.0–253.0° C.

EXAMPLE 5

<Synthesis of 6-(1-butanesulfonylcarbamoyl)-1-(2-chloro-4-phenylbenzyl)-2-methylbenzimidazole (5)>

In the same manner as in Example 1, 0.250 g of the title compound were formed from 0.250 g of 6-carboxy-1-(2-chloro-4-phenylbenzyl)-2-methylbenzimidazole and 0.118 g of 1-butanesulfonamide.

[Properties of Compound (5)]
$^1$H-NMR(DMSO-d$_6$, δ ppm): 0.83(3H, t, J=7.3 Hz), 1.34–1.41(2H, m), 1.61–1.69(2H, m), 2.53(3H, s), 3.49(2H, t, J=7.7 Hz), 5.64(2H, s), 6.49(1H, d, J=8.2 Hz), 7.38(1H, t, J=7.3 Hz), 7.45(2H, t, J=7.3 Hz), 7.53(1H, dd, J=8.2 and 1.8 Hz), 7.65(2H, d, J=7.3 Hz), 7.69(1H, d, J=8.6 Hz), 7.81(1H, dd, J=8.4 and 1.5 Hz), 7.85(1H, d, J=1.9 Hz), 8.15(1H, d, J=1.5 Hz), 11.88(1H, brs).
IR(Nujol): 1683 cm$^{-1}$.
mp: 249.3–250.1° C.

EXAMPLE 6

<Synthesis of 1-(2-chloro-4-(2-phenylethyl)benzyl)-2-methyl-6-((4-methylbenzene)sulfonylcarbamoyl) benzimidazole (6)>

In the same manner as in Example 1,1-(2-chloro-4-((E)-2-phenylethenyl)benzyl)-2-methyl-6-((4-methylbenzene) sulfonylcarbamoyl)benzimidazole was formed from 0.300 g of 6-carboxy-1-(2-chloro-4-((E)-(2-phenylethenyl)benzyl)-2-methylbenzimidazole and 0.166 g of (4-methylbenzene) sulfonamide. This compound was dissolved in 10 ml of acetic acid, and 10 mg of platinum (IV) oxide was added in a nitrogen atmosphere. The mixture was stirred in a hydrogen atmosphere for 2 hours. The solid was removed through filtration, and the filtrate was concentrated. The residue was recrystallized from a mixture of water and acetone to give 0.065 g of the title compound.

[Properties of Compound(6)]
$^1$H-NMR(DMSO-d$_6$, δ ppm): 2.37(3H, s), 2.48(3H, s), 2.83(4H, s), 5.54(2H, s), 6.37(1H; d, J=8.1 Hz), 7.07(1H, d, J=7.9 Hz), 7.13–7.25(5H, m), 7.37–7.43(3H, m), 7.64(1H, d, J=8.5 Hz), 7.72(1H, d, J=9.6 Hz), 7.86(2H, d, J=8.3 Hz), 8.05(1H, s), 12.32(1H, brs).
IR(Nujol): 1689 cm$^{-1}$.
mp: 205.7–208.9° C.

EXAMPLE 7

<Synthesis of 1-(2-chloro-4-(phenyloxymethyl)benzyl)-2-methyl-6-((E)-(1-pent-1-ene)sulfonylcarbamoyl)benzimidazole (7)>

In the same manner as in Example 1, 0.11 g of the title compound were formed from 0.15 g of 6-carboxy-1-(2-chloro-4-(phenyloxymethyl)benzyl)-2-methylbenzimidazole and 0.07 g of (E)-1-pent-1-enesulfonamide.

[Properties of Compound (7)]
$^{1}$H-NMR(DMSO-d$_{6}$, δ ppm): 0.85(3H, dt, J=7.3 and 2.8 Hz), 1.38–1.48(2H, m), 2.18–2.26(2H, m), 2.49(3H, s), 5.08(2H, s), 5.59(2H, s), 6.45(1H, d, J=7.9 Hz), 6.76(1H, dd, J=16.4 and 1.4 Hz), 6.82–6.90(1H, m), 6.91–6.95(1H, m), 6.97(2H, d, J=8.5 Hz), 7.25–7.31(3H, m), 7.65–7.67(2H, m), 7.77(1H, d, J=8.5 Hz), 8.08(1H, s), 11.96(1H, brs).
IR(Nujol): 1672 cm$^{-1}$.
mp: 177.0–184.0° C.

EXAMPLE 8

<Synthesis of 1-(2-chloro-4-(phenyloxymethyl)benzyl)-2-methyl-6-((E)-(2-phenylethene)sulfonylcarbamoyl)benzimidazole (8)>

In the same manner as in Example 1, 0.16 g of the title compound were formed from 0.15 g of 6-carboxy-1-(2-chloro-4-(phenyloxymethyl)benzyl)-2-methylbenzimidazole and 0.09 g of (E)-(2-phenylethene)sulfonamide.

[Properties of Compound (8)]
$^{1}$H-NMR(DMSO-d$_{6}$, δ ppm): 2.49(3H, s), 5.07(2H, s), 5.59(2H, s), 6.44(1H, d, J=7.5 Hz), 6.91–6.98(3H, m), 7.24–7.30(3H, m), 7.42–7.51(4H, m), 7.61–7.65(2H, m), 7.66(1H, d, J=8.5 Hz), 7.75(2H, d, J=7.3 Hz), 7.79(1H, d, J=8.5 Hz), 8.11(1H, s), 12.15(1H, brs).
IR(Nujol): 1672 cm$^{-1}$.
mp: 220.2–223.5° C.

EXAMPLE 9

<Synthesis of 6-(1-butanesulfonylcarbamoyl)-1-(2-chloro-4-(phenyloxymethyl)benzyl)-2-methylbenzimidazole (9)>

In the same manner as in Example 1, 0.15 g of the title compound were formed from 0.15 g of 6-carboxy-1-(2-chloro-4-(phenyloxymethyl)benzyl)-2-methylbenzimidazole and 0.07 g of 1-butanesulfonamide.

[Properties of Compound (9)]
$^{1}$H-NMR(DMSO-d$_{6}$, δ ppm): 0.84(3H, dt, J=7.3 and 2.5 Hz), 1.34–1.42(2H, m), 1.61–1.69(2H, m), 2.49(3H, s), 3.49(2H, t, J=8.6 Hz), 5.07(2H, s), 5.60(2H, s), 6.46(1H, d, J=7.9 Hz), 6.92(1H, t, J=7.1 Hz), 6.97(2H, d, J=8,6 Hz), 7.25–7.31(3H, m), 7.64(1H, s), 7.67(1H, d, J=8.5 Hz), 7.80(1H, d, J=8.4 Hz), 8.10(1H, s), 11.86(1H, brs).
IR(Nujol): 1689 cm$^{-1}$.
mp: 198.0–205.0° C.

EXAMPLE 10

<Synthesis of 1-(2-chloro-4-(phenyloxymethyl)benzyl)-2-methyl-6-((3-methylbenzene)sulfonylcarbamoyl)benzimidazole (10)>

In the same manner as in Example 1, 0.14 g of the title compound were formed from 0.15 g of 6-carboxy-1-(2-chloro-4-(phenyloxymethyl)benzyl)-2-methylbenzimidazole and 0.08 g of (3-methylbenzene)sulfonamide.

[Properties of Compound (10)]
$^{1}$H-NMR(DMSO-d$_{6}$, δ ppm): 2.39(3H, m), 2.48(3H, s), 5.07(2H, s), 5.59(2H, s), 6.43(1H, d, J=7.8 Hz), 6.93(1H, t, J=7.1 Hz), 6.97(2H, d, J=8.4 Hz), 7.25–7.30(3H, m), 7.49 (2H, d, J=4.2 Hz), 7.62–7.66(2H, m), 7.72(1H, d, J=7.5 Hz), 7.77(2H, s), 8.06(1H, s), 12.35(1H, brs).
mp: 160.1–170.1° C.

EXAMPLE 11

<Synthesis of 1-(2-chloro-4-(n-octyloxy)benzyl)-2-methyl-6-(1-pentanesulfonylcarbamoyl)benzimidazole (11)>

In the same manner as in Example 1, 0.25 g of the title compound were formed from 0.25 g of 6-carboxy-1-(2-chloro-4-(n-octyloxy)benzyl)-2-methylbenzimidazole and 0.11 g of 1-pentanesulfonamide.

[Properties of Compound (11)]
$^{1}$H-NMR(DMSO-d$_{6}$, δ ppm): 0.75–0.90(6H, m), 1.15–1.47(14H, m), 1.62–1.73(4H, m), 3.49(2H, t, J=7.5 Hz), 3.93(2H, t, J=6.4 Hz), 5.50(2H, s), 6.45(1H, d, J=8.7 Hz), 6.80(1H, dd, J=8.7 and 2.5 Hz), 7.11(1H, d, J=2.3 Hz), 7.65(1H, d, J=8.5 Hz), 7.78(1H, d, J=8.4 Hz), 8.09(1H, s), 11.86(1H, brs).
IR(Nujol): 1667 cm$^{-1}$.
mp: 170.1–173.4° C.

EXAMPLE 12

<Synthesis of 1-(2-chloro-4-(n-octyloxy)benzyl)-2-methyl-6-((4-methylbenzene)sulfonylcarbamoyl)benzimidazole (12)>

In the same manner as in Example 1, 0.21 g of the title compound were formed from 0.20 g of 6-carboxy-1-(2-chloro-4-(n-octyloxy)benzyl)-2-methylbenzimidazole and 0.10 g of (4-methylbenzene)sulfonamide.

[Properties of Compound (12)]
$^{1}$H-NMR(DMSO-d$_{6}$, δ ppm): 0.86(3H, t, J=7.1 Hz), 1.21–1.45(10H, m), 1.63–1.71(2H, m), 2.39(3H, s), 3.95 (2H, t, J=6.3 Hz), 5.51(2H, s), 6.44(1H, d, J=8.6 Hz), 6.81(1H, dd, J=8.4 and 2.5 Hz), 7.13(1H, d, J=2.5 Hz), 7.42(2H, d, J=8.0 Hz), 7.63(1H, d, J=8.5 Hz), 7.73 (1H, d, J=8.4 Hz), 7.88(2H, d, J=8.1 Hz), 8.06(1H, s), 12.37(1H, brs).
MASS(FD): m/z 582 (M+1).
mp: 205.3–214.0° C.

EXAMPLE 13

<Synthesis of 1-(2-chloro-4-(n-hexyloxy)benzyl)-2-methyl-6-(1-pentanesulfonylcarbamoyl)benzimidazole (13)>

In the same manner as in Example 1, 0.075 g of the title compound were formed from 0.200 g of 6-carboxy-1-(2-chloro-4-(n-hexyloxy)benzyl)-2-methylbenzimidazole and 0.089 g of 1-pentanesulfonamide.

[Properties of Compound (13)]
$^{1}$H-NMR(DMSO-d$_{6}$, δ ppm): 0.81(3H, t, J=7.3 Hz), 0.85 (3H, t, J=7.0 Hz), 1.22–1.30(6H, m), 1.30–1.39(4H, m), 1.62–1.71(4H, m), 2.49(3H, s), 3.49(2H, t, J=7.7 Hz), 3.93 (2H, t, J=6.5 Hz), 5.50(2H, s), 6.45(1H, d, J=8.7 Hz), 6.81(1H, dd, J=8.6 and 2.5 Hz), 7.12(1H, d, J=2.5 Hz), 7.65(1H, d, J=8.5 Hz), 7.78(1H, dd, J=8.5 and 1.6 Hz), 8.09(1H, d, J=1.3 Hz), 11.91(1H, brs).
IR(Nujol): 1672 cm$^{-1}$.
mp: 171.6–173.5° C.

EXAMPLE 14

<Synthesis of 1-(2-chloro-4-(n-pentyloxy)benzyl)-2-methyl-6-(1-pentanesulfonylcarbamoyl)benzimidazole (14)>

In the same manner as in Example 1, 0.17 g of the title compound were formed from 0.20 g of 6-carboxy-1-(2- chloro-4-(n-pentyloxy)benzyl)-2-methylbenzimidazole and 0.10 g of 1-pentanesulfonamide.

[Properties of Compound (14)]

$^1$H-NMR(DMSO-d$_6$, δ ppm): 0.81(3H, t, J=7.2 Hz), 0.86 (3H, t, J=7.0 Hz), 1.20–1.40(8H, m), 1.62–1.74(4H, m), 3.48(2H, t, J=8.3 Hz), 3.93(2H, t, J=6.3 Hz), 5.50(2H, s), 6.45(1H, d, J=8.9 Hz), 6.81(1H, dd, J=8.4 and 2.5 Hz), 7.12(1H, d, J=2.6 Hz), 7.65(1H, d, J=8.5 Hz), 7.78(1H, d, J=8.9 Hz), 8.09(1H,d, J=1.5 Hz), 11.86(1H, brs).

IR(Nujol): 1672 cm$^{-1}$.

mp: 178–181° C.

EXAMPLE 15

<Synthesis of 1-(2-chloro-4-(n-pentyloxy)benzyl)-2-methyl-6-((4-methylbenzene)sulfonylcarbamoyl)benzimidazole (15)>

In the same manner as in Example 1, 0.17 g of the title compound were formed from 0.20 g of 6-carboxy-1-(2-chloro-4-(n-pentyloxy)benzyl)-2-methylbenzimidazole and 0.12 g of (4-methylbenzene)sulfonamide.

[Properties of Compound (15)]

$^1$H-NMR(DMSO-d$_6$, δ ppm): 0.88(3H, t, J=7.0 Hz), 1.28–1.42(4H, m), 1.62–1.68(2H, m), 2.39(3H, s), 2.51(3H, s), 3.95(2H, t, J=6.5 Hz), 5.51(2H, s), 6.44(1H, d, J=8.6 Hz), 6.81(1H, dd, J=8.4 and 2.3 Hz), 7.13(1H, d, J=2.6 Hz), 7.42(2H, J=8.1 Hz), 7.63(1H, d, J=8.5 Hz), 7.72(1H, d, J=8.4 Hz), 7.88(2H, d, J=8.3 Hz), 8.06(1H, s), 12.34(1H, brs).

IR(Nujol): 1688 cm$^{-1}$.

mp: 214–217° C.

EXAMPLE 16

<Synthesis of 1-(4-n-butyloxy-2-chlorobenzyl)-2-methyl-6-((4-methylbenzene)sulfonylcarbamoyl)benzimidazole (16)>

In the same manner as in Example 1, 0.18 g of the title compound were formed from 0.20 g of 6-carboxy-1-(4-n-butyloxy-2-chlorobenzyl)-2-methylbenzimidazole and 0.12 g of (4-methylbenzene)sulfonamide.

[Properties of Compound (16)]

$^1$H-NMR(DMSO-d$_6$, δ ppm): 0.89(3H, t, J=7.4 Hz), 1.34–1.42(2H, m), 1.62–1.67(2H, m), 2.37(3H, s), 2.47(3H, s), 3.93(2H, t, J=6.5 Hz), 5.48(2H, s), 6.41(1H, d, J=8.7 Hz), 6.79(1H, dd, J=8.6 and 2.5 Hz), 7.11(1H, d, J=2.5 Hz), 7.40(2H, d, J=8.2 Hz), 7.61(1H, d, J=8.4 Hz), 7.70(1H, dd, J=8.4 and 1.7 Hz), 7.85(2H, d, J=8.3 Hz), 8.03(1H, s), 12.36(1H, brs).

MASS(FD): m/z 525 (M).

mp: 214.8–219.1° C.

EXAMPLE 17

<Synthesis of 1-(2-chloro-4-(n-propyloxy)benzyl)-2-methyl-6-(1-pentanesulfonylcarbamoyl)benzimidazole (17)>

In the same manner as in Example 1, 0.15 g of the title compound were formed from 0.20 g of 6-carboxy-1-(2-chloro-4-(n-propyloxy)benzyl)-2-methylbenzimidazole and 0.11 g of 1-pentanesulfonamide.

[Properties of Compound (17)]

$^1$H-NMR(DMSO-d$_6$, δ ppm): 0.81(3H, t, J=7.2 Hz), 0.93 (3H, t, J=7.4 Hz), 1.21–1.29(2H, m), 1.33–1.38(2H, m), 1.65–1.72(4H, m), 2.49(3H, s), 3.49(2H, t, J=7.4 Hz), 3.90 (2H, t, J=6.5 Hz), 5.50(2H, s), 6.45(1H, d, J=9.0 Hz), 6.81(1H, dd, J=8.8 and 2.5 Hz), 7.12(1H, d, J=2.5 Hz), 7.65(1H, d, J=8.6 Hz), 7.78(1H, dd, J=8.4 and 1.7 Hz), 8.09(1H, s), 11.89(1H, brs).

IR(Nujol): 1672 cm$^{-1}$.

mp: 178.0–183.5° C.

EXAMPLE 18

<Synthesis of 1-(2-chloro-4-(n-propyloxy)benzyl)-2-methyl-6-((4-methylbenzene)sulfonylcarbamoyl)benzimidazole (18)>

In the same manner as in Example 1, 0.20 g of the title compound were formed from 0.20 g of 6-carboxy-1-(2-chloro-4-(n-propyloxy)benzyl)-2-methylbenzimidazole and 0.12 g of (4-methylbenzene)sulfonamide.

[Properties of Compound (18)]

$^1$H-NMR(DMSO-d$_6$, δ ppm): 0.93(3H, dt, J=7.3 and 1.9 Hz), 1.65–1.73(2H, m), 2.38(3H, s), 2.47(3H, s), 3.90(2H, dt, J=6.5 and 1.9 Hz), 5.49(2H, s), 6.42(1H, d, J=8.8 Hz), 6.80(1H, dd, J=8.9 and 2.5 Hz), 7.11(1H, d, J=2.4 Hz), 7.40(2H, d, J=7.5 Hz), 7.61(1H, d, J=8.5 Hz), 7.70(1H, d, J=8.5 Hz), 7.86(2H, dd, J=8.4 and 2.0 Hz), 8.04(1H, s), 12.29(1H, brs).

mp: 213.5–235.5° C.

EXAMPLE 19

<Synthesis of 1-(2-chloro-4-(methyloxy)benzyl)-2-methyl-6-(1-pentanesulfonylcarbamoyl)benzimidazole (19)>

In the same manner as in Example 1, 0.15 g of the title compound were formed from 0.180 g of 6-carboxy-1-(2-chloro-4-(methyloxy)benzyl)-2-methylbenzimidazole and 0.126 g of 1-pentanesulfonamide.

[Properties of Compound (19)]

$^1$H-NMR(DMSO-d$_6$, δ ppm): 0.81(3H, t, J=7.3 Hz), 1.25 (2H, m), 1.35(2H, m), 1.68(2H, m), 4.29(3H, s), 3.49(2H, t, J=7.8 Hz), 3.73(3H, s), 5.51(2H, s), 6.48(1H, d, J=8.7 Hz), 6.82(1H, dd, J=8.7 and 2.6 Hz), 7.14(1H, d, J=2.5 Hz), 7.66(1H, d, J=8.5 Hz), 7.78(1H, dd, J=8.4 and 1.5 Hz), 8.09(1H, s), 11.87(1H, brs).

IR(Nujol): 1689 cm$^{-1}$.

mp: 211–213° C.

EXAMPLE 20

<Synthesis of 1-(2-chloro-4-(methyloxy)benzyl)-2-methyl-6-((4-methylbenzene)sulfonylcarbamoyl)benzimidazole (20)>

In the same manner as in Example 1, 0.14 g of the title compound were formed from 0.180 g of 6-carboxy-1-(2-chloro-4-(methyloxy)benzyl)-2-methylbenzimidazole and 0.142 g of (4-methylbenzene)sulfonamide.

[Properties of Compound (20)]

$^1$H-NMR(DMSO-d$_6$, δ ppm): 2.37(3H, s), 2.47(3H, s), 3.73(3H, s), 5.49(2H, s), 6.45(1H, d, J=8.7 Hz), 6.81(1H, dd, J=8.7 and 2.5 Hz), 7.13(1H, d, J=2.5 Hz), 7.41(2H, d, J=8.2 Hz), 7.62(1H, d, J=8.5 Hz), 7.70(1H, d, J=8.5 Hz), 7.86(2H, d, J=8.2 Hz), 8.03(1H, s), 12.30(1H, brs).

IR(Nujol): 1694 cm$^{-1}$.

mp: 213–216° C.

EXAMPLE 21

<Synthesis of 1-(2-chloro-4-((2-methyloxyethyl)oxy)benzyl)-2-methyl-6-(1-pentanesulfonylcarbamoyl)benzimidazole (21)>

In the same manner as in Example 1, 0.05 g of the title compound were formed from 0.16 g of 6-carboxy-1-(2-chloro-4-((2-methyloxyethyl)oxy)benzyl)-2-methylbenzimidazole and 0.08 g of 1-pentanesulfonamide.

[Properties of Compound (21)]

$^1$H-NMR(DMSO-d$_6$, δ ppm): 0.81(3H, t, J=7.1 Hz), 1.22–1.28(2H, m), 1.32–1.38(2H, m), 1.64–1.72(2H, m), 2.49(3H, s), 3.26(3H, s), 3.46–3.51(2H, m), 3.60(2H, t, J=4.4 Hz), 4.07(2H, t, J=4.5 Hz), 5.51(2H, s), 6.45(1H, d, J=8.8 Hz), 6.83(1H, dd, J=8.1 and 2.5 Hz), 7.15(1H, d, J=2.5 Hz), 7.65(1H, d, J=8.5 Hz), 7.78(1H, d, J=8.4 Hz), 8.10(1H, d, J=1.3 Hz), 11.89(1H, bts).

IR(Nujol): 1672 cm$^{-1}$.

mp: 165–168° C.

EXAMPLE 22

<Synthesis of 1-(2-chloro-4-((2-methyloxyethyl)oxy)benzyl)-2-methyl-6-((4-methylbenzene)sulfonylcarbamoyl)benzimidazole (22)>

In the same manner as in Example 1, 0.12 g of the title compound were formed from 0.16 g of 6-carboxy-1-(2-chloro-4-((2-methyloxyethyl)oxy)benzyl)-2-methylbenzimidazole and 0.11 g of (4-methylbenzene)sulfonamide.

[Properties of Compound (22)]

$^1$H-NMR(DMSO-d$_6$, δ ppm): 2.37(3H, s), 2.47(3H, s), 3.27(3H, s), 3.59–3.62(2H, m), 4.06–4.08(2H, m), 5.49(2H, s), 6.42(1H, d, J=8.6 Hz), 6.81(1H, dd, J=8.6 and 2.5 Hz), 7.14(1H, d, J=2.5 Hz), 7.40(2H, d, J=8.2 Hz), 7.61(1H, d, J=8.5 Hz), 7.70(1H, d, J=8.7 Hz), 7.85(2H, d, J=8.2 Hz), 8.03(1H, s), 12.36(1H, brs).

IR(Nujol): 1689 cm$^{-1}$.

mp: 198.5–203.0° C.

EXAMPLE 23

<Synthesis of 1-(2-chloro-4-(cyclopentylmethyloxy)benzyl)-2-methyl-6-(1-pentanesulfonylcarbamoyl)benzimidazole (23)>

In the same manner as in Example 1, 0.178 g of the title compound were formed from 0.150 g of 6-carboxy-1-(2-chloro-4-(cyclopentylmethyloxy)benzyl)-2-methylbenzimidazole and 0.065 g of 1-pentanesulfonamide.

[Properties of Compound (23)]

$^1$H-NMR(DMSO-d$_6$, δ ppm): 0.81(3H, t, J=7.1 Hz), 1.21–1.42(6H, m), 1.48–1.78(8H, m), 2.21–2.28(1H, m), 3.49(2H, t, J=7.6 Hz), 3.81(2H, d, J=7.0 Hz), 5.50(2H, s), 6.45(1H, d, J=8.7 Hz), 6.81(1H, d, J=8.5 Hz), 7.12(1H, d, J=2.1 Hz), 7.65(1H, d, J=8.3 Hz), 7.78(1H, d, J=7.6 Hz), 8.09(1H, s), 11.86(1H, brs).

IR(Nujol): 1667 cm$^{-1}$.

mp: 184.0–185.5° C.

EXAMPLE 24

<Synthesis of 1-(2-chloro-4-(cyclopentylmethyloxy)benzyl)-2-methyl-6-((4-methylbenzene)sulfonylcarbamoyl)benzimidazole (24)>

In the same manner as in Example 1, 0.161 g of the title compound were formed from 0.150 g of 6-carboxy-1-(2-chloro-4-(cyclopentylmethyloxy)benzyl)-2-methylbenzimidazole and 0.073 g of (4-methylbenzene)sulfonamide.

[Properties of Compound (24)]

$^1$H-NMR(DMSO-d$_6$, δ ppm): 1.23–1.31(2H, m), 1.47–1.60(4H, m), 1.68–1.76(2H, m), 2.21–2.27(1H, m), 2.38(3H, s), 2.47(3H, m), 3.81(2H, d, J=7.0 Hz), 5.49(2H, s), 6.42(1H, d, J=8.6 Hz), 6.79(1H, dd, J=8.7 and 2.4 Hz), 7.12(1H, d, J=2.5 Hz), 7.40(2H, d, J=8.2 Hz), 7.61(1H, d, J=8.5 Hz), 7.70(1H, d, J=8.5 Hz), 7.86(2H, d, J=8.3 Hz), 8.03(1H, s), 12.30(1H, brs).

IR(Nujol): 1694 cm$^{-1}$.

mp: 221.5–222.5° C.

EXAMPLE 25

<Synthesis of 1-(2-chloro-4-(cyclopentylmethyloxy)benzyl)-2-methyl-6-((E)-1-pent-1-enesulfonylcarbamoyl)benzimidazole (25)>

In the same manner as in Example 1, 0.107 g of the title compound were formed from 0.150 g of 6-carboxy-1-(2-chloro-4-(cyclopentylmethyloxy)benzyl)-2-methylbenzimidazole and 0.064 g of (E)-1-pent-1-enesulfonamide.

[Properties of Compound (25)]

$^1$H-NMR(DMSO-d$_6$, δ ppm): 0.86(3H, t, J=7.3 Hz), 1.23–1.32(2H, m), 1.40–1.61(6H, m), 1.68–1.76(2H, m), 2.20–2.28(3H, m), 2.50(3H, s), 3.81(2H, d, J=7.0 Hz), 5.49(2H, s), 6.43(1H, d, J=8.7 Hz), 6.73–6.89(3H, m), 7.12(1H, d, J=2.5 Hz), 7.64(1H, d, J=12.5 Hz), 7.76(1H, dd, J=8.5 and 1.6 Hz), 8.06(1H, s), 11.96(1H, brs).

IR(Nujol): 1672 cm$^{-1}$.

mp: 193.5–194.5° C.

EXAMPLE 26

<Synthesis of 6-(benzenesulfonylcarbamoyl)-1-(4-benzyloxy-2-chlorobenzyl)-2-methylbenzimidazole (26)>

In the same manner as in Example 1, 0.132 g of the title compound were formed from 0.183 g of 1-(4-benzyloxy-2-chlorobenzyl)-6-carboxy-2-methylbenzimidazole and 0.099 g of benzenesulfonamide.

[Properties of Compound (26)]

$^1$H-NMR(DMSO-d$_6$, δ ppm): 2.47(3H, s), 5.08(2H, s), 5.50(2H, s), 6.44(1H, d, J=8.6 Hz), 6.89(1H, d, J=8.7 Hz), 7.23(1H, s), 7.32(1H, m), 7.39(4H, m), 7.61(3H, m), 7.70(2H, m), 7.98(2H, d, J=7.9 Hz), 8.05(1H, s), 12.40(1H, brs).

IR(Nujol): 1689 cm$^{-1}$.

mp: 217–219° C.

EXAMPLE 27

<Synthesis of 1-(4-benzyloxy-2-chlorobenzyl)-2-methyl-6-((3-methylbenzene)sulfonylcarbamoyl)benzimidazole (27)>

In the same manner as in Example 1, 0.188 g of the title compound were formed from 0.183 g of 1-(4-benzyloxy-2-chlorobenzyl)-6-carboxy-2-methylbenzimidazole and 0.108 g of (3-methylbenzene)sulfonamide.

[Properties of Compound (27)]

$^1$H-NMR(DMSO-d$_6$, δ ppm): 2.39(3H, s), 2.53(3H, s), 5.08(2H, s), 5.50(2H, s), 6.44(1H, d, J=8.7 Hz), 6.89(1H, d, J=8.7 Hz), 7.23(1H, s), 7.32(1H, t, J=6.6 Hz), 7.39(4H, m), 7.50(2H, m), 7.63(1H, d, J=8.5 Hz), 7.72(1H, d, J=8.5 Hz), 7.78(2H, m), 8.05(1H, s), 12.40(1H, brs).

IR(Nujol): 1606 cm$^{-1}$.

mp: 202.0–203.7° C.

EXAMPLE 28

<Synthesis of 1-(4-benzyloxy-2-chlorobenzyl)-2-methyl-6-((E)-(2-phenylethene)sulfonylcarbamoyl)benzimidazole (28)>

In the same manner as in Example 1, 0.207 g of the title compound were formed from 0.183 g of 1-(4-benzyloxy-2-chlorobenzyl)-6-carboxy-2-methylbenzimidazole and 0.115 g of (E)-(2-phenylethene)sulfonamide.

[Properties of Compound (28)]

$^1$H-NMR(DMSO-d$_6$, δ ppm): 2.49(3H, s), 5.08(2H, s), 5.50(2H, s), 6.44(1H, d, J=8.7 Hz), 6.89(1H, dd, J=8.6 and 2.4 Hz), 7.23(1H, d, J=2.4 Hz), 7.31(1H, t, J=6.8 Hz), 7.34–7.51(8H, m), 7.64(2H, m), 7.77(3H, m), 8.11(1H, s), 12.20(1H, brs).

IR(Nujol): 1672 cm$^{-1}$.

mp: 229.7–231.6° C.

EXAMPLE 29

<Synthesis of 1-(4-benzyloxy-2-chlorobenzyl)-2-methyl-6-((5-chloro-2-thiophene)sulfonylcarbamoyl)benzimidazole (29)>

In the same manner as in Example 1, 0.175 g of the title compound were formed from 0.183 g of 1-(4-benzyloxy-2-chlorobenzyl)-6-carboxy-2-methylbenzimidazole and 0.152 g of (5-chloro-2-thiophene)sulfonamide.

[Properties of Compound (29)]

$^1$H-NMR(DMSO-d$_6$, δ ppm): 2.60(3H, s), 5.10(2H, s), 5.59(2H, s), 6.65(1H, m), 6.91(1H, s, J=8.9 Hz), 7.17(1H, d, J=32.2 Hz), 7.24(1H, s), 7.30–7.42(5H, m), 7.56(1H, s), 7.68(1H, d, J=8.5 Hz), 7.90(1H, d, J=8.3 Hz), 8.09(1H, s).
IR(Nujol): 1606 cm$^{-1}$.
mp: 272–274° C.

EXAMPLE 30

<Synthesis of 1-(4-benzyloxy-2-chlorobenzyl)-6-(1-butanesulfonylcarbamoyl)-2-methylbenzimidazole (30)>

In the same manner as in Example 1, 0.175 g of the title compound were formed from 0.183 g of 1-(4-benzyloxy-2-chlorobenzyl)-6-carboxy-2-methylbenzimidazole and 0.106 g of 1-butanesulfonamide.

[Properties of Compound (30)]
$^1$H-NMR(DMSO-d$_6$, δ ppm): 0.85(3H, t, J=7.3 Hz), 1.39 (2H, m), 1.66(2H, m), 2.49(3H, s), 3.50(2H, t, J=7.6 Hz), 5.09(2H, s), 5.51(2H, s), 6.46(1H, d, J=8.7 Hz), 6.90(1H, dd, J=8.7 and 2.4 Hz), 7.25(1H, d, J=2.5 Hz), 7.31(1H, t, J=7.0 Hz), 7.35–7.52(4H, m), 7.66(1H, d, J=8.5 Hz), 7.79(1H, d, J=8.5 Hz) 8.10(1H, s), 11.88(1H, brs).
IR(Nujol): 1672 cm$^{-1}$.
mp: 186–188° C.

EXAMPLE 31

<Synthesis of 1-(4-benzyloxy-2-chlorobenzyl)-2-methyl-6-((E)-1-pent-1-enesulfonylcarbamoyl)benzimidazole (31)>

In the same manner as in Example 1, 0.152 g of the title compound were formed from 0.183 g of 1-(4-benzyloxy-2-chlorobenzyl)-6-carboxy-2-methylbenzimidazole and 0.115 g of (E)-1-pent-1-enesulfonamide.

[Properties of Compound (31)]
$^1$H-NMR(DMSO-d$_6$, δ ppm): 0.86(3H, t, J=7.4 Hz), 1.44 (2H, m), 2.23(2H, m), 2.49(3H, s), 5.09(2H, s), 5.50(2H, s), 6.45(1H, d, J=8.7 Hz), 6.77(1H, d, J=15.1 Hz), 6.84–6.91 (2H, m), 7.24(1H, d, J=2.5 Hz), 7.32(1H, t, J=7.0 Hz), 7.35–7.42(4H, m), 7.65(1H, d, J=8.5 Hz), 7.77(1H, dd, J=8.5 and 1.5 Hz), 8.08(1H, s), 12.05(1H, brs).
IR(Nujol): 1672 cm$^{-1}$.
mp: 206–209° C.

EXAMPLE 32

<Synthesis of 6-(1-butanesulfonylcarbamoyl)-1-(2-chloro-4-(2-thienyl)benzyl)-2-methylbenzimidazole (32)>

In the same manner as in Example 1, 0.145 g of the title compound were formed from 0.218 g of 6-carboxy-1-(2-chloro-4-(2-thienyl)benzyl)-2-methylbenzimidazole and 0.110 g of 1-butanesulfonamide.

[Properties of Compound (32)]
$^1$H-NMR(DMSO-d$_6$, δ ppm): 0.88(3H, t, J=7.3 Hz), 1.43 (2H, m), 1.70(2H, m), 2.57(3H, s), 3.54(2H, t, J=7.7 Hz), 5.66(2H, s), 6.54(1H, d, J=8.2 Hz), 7.18(1H, t, J=4.3 Hz), 7.55(1H, d, J=8.2 Hz), 7.63(2H, m), 7.74(1H, d, J=8.5 Hz), 7.86(1H, dd, J=8.5 and 1.4 Hz), 7.91(1H, d, J=1.7 Hz), 8.18(1H, s), 11.95(1H, brs).
IR(Nujol): 1683 cm$^{-1}$.
mp: 258–261° C.

EXAMPLE 33

<Synthesis of 1-(2-chloro-4-(2-thienyl)benzyl)-2-methyl-6-((E)-1-pent-1-enesulfonylcarbamoyl)benzimidazole (33)>

In the same manner as in Example 1, 0.155 g of the title compound were formed from 0.218 g of 6-carboxy-1-(2-chloro-4-(2-thienyl)benzyl)-2-methylbenzimidazole and 0.119 g of (E)-1-pent-1-enesulfonamide.

[Properties of Compound (33)]
$^1$H-NMR(DMSO-d$_6$, δ ppm): 0.84(3H, t, J=7.4 Hz), 1.42 (2H, m), 2.20(2H, m), 2.51(3H, s), 5.60(2H, s), 6.47(1H, d, J=8.1 Hz), 6.75(1H, d, J=15.0 Hz), 6.85(1H, dt, J=15.0 and 6.8 Hz), 7.13(1H, t, J=4.4 Hz), 7.49(1H, d, J=8.0 Hz), 7.58(2H, m), 7.67(1H, d, J=8.5 Hz), 7.78(1H, d, J=8.4 Hz), 7.86(1H, d, J=1.4 Hz), 8.11(1H, s), 11.97(1H, brs).
IR(Nujol): 1672 cm$^{-1}$.
mp: 238–240° C.

EXAMPLE 34

<Synthesis of 6-(benzenesulfonylcarbamoyl)-1-(2-chloro-4-(2-furyl)benzyl)-2-methylbenzimidazole (34)>

In the same manner as in Example 1, 0.128 g of the title compound were formed from 0.150 g of 6-carboxy-1-(2-chloro-4-(2-furyl)benzyl)-2-methylbenzimidazole and 0.090 g of benzenesulfonamide.

[Properties of Compound (34)]
$^1$H-NMR(DMSO-$_6$, δ ppm): 2.49(3H, s), 5.59(2H, s), 6.50(1H, d, J=8.1 Hz), 6.60(1H, s), 7.04(1H, s), 7.53(1H, d, J=8.0 Hz), 7.60(2H, m), 7.66(2H, m), 7.73(1H, d, J=8.4 Hz), 7.76(1H, s), 7.87(1H, s), 7.97(2H, d, J=7.6 Hz), 8.08(1H, s).
IR(Nujol): 1678 cm$^{-1}$.
mp: 245–248° C.

EXAMPLE 35

<Synthesis of 1-(2-chloro-4-(2-furyl)benzyl)-2-methyl-6-((3-methylbenzene)sulfonylcarbamoyl)benzimidazole (35)>

In the same manner as in Example 1, 0.174 g of the title compound were formed from 0.150 g of 6-carboxy-1-(2-chloro-4-(2-furyl)benzyl)-2-methylbenzimidazole and 0.098 g of (3-methylbenzene)sulfonamide.

[Properties of Compound (35)]
$^1$H-NMR(DMSO-d$_6$, δ ppm): 2.37(3H, s), 2.50(3H, s), 5.61(2H, s), 6.52(1H, d, J=8.2 Hz), 6.60(1H, m), 7.05(1H, d, J=3.1 Hz), 7.49(2H, m), 7.53(1H, d, J=8.2 Hz), 7.67(1H, t, J=8.3 Hz), 7.76(4H, m), 7.87(1H, s), 8.11(1H, s), 12.45(1H, brs).
IR(Nujol): 1617 cm$^{-1}$.
mp: 228.6–231.0° C.

EXAMPLE 36

<Synthesis of 1-(2-chloro-4-(2-furyl)benzyl)-2-methyl-6-((E)-(2-phenylethene)sulfonylcarbamoyl)benzimidazole (36)>

In the same manner as in Example 1, 0.170 g of the title compound were formed from 0.150 g of 6-carboxy-1-(2-chloro-4-(2-furyl)benzyl)-2-methylbenzimidazole and 0.104 g of (E)-(2-phenylethene)sulfonamide.

[Properties of Compound (36)]
$^1$H-NMR(DMSO-d$_6$, δ ppm): 2.52(3H, s), 5.61(2H, s), 6.54(1H, d, J=8.1 Hz), 6.59(1H, m), 7.05(1H, d, J=3.4Hz), 7.44(3H, m), 7.49(1H, d, J=15.4 Hz), 7.53(1H, dd, J=8.2 and 1.4 Hz), 7.63(1H, d, J=15.5 Hz), 7.69(1H, d, J=8.5 Hz), 7.75(3H, m), 7.82(1H, dd, J=8.5 and 1.4 Hz), 7.87(1H, d, J=1.5 Hz), 8.17(1H, s), 12.15(1H, brs).
IR(Nujol): 1689 cm$^{-1}$.
mp: 236.2–236.2° C.

EXAMPLE 37

<Synthesis of 1-(2-chloro-4-(2-furyl)benzyl)-6-((5-chloro-2-thiophene)sulfonylcarbamoyl)-2-methylbenzimidazole (37)>

In the same manner as in Example 1, 0.132 g of the title compound were formed from 0.150 g of 6-carboxy-1-(2-chloro-4-(2-furyl)benzyl)-2-methylbenzimidazole and 0.113 g of (5-chloro-2-thiophene)sulfonamide.

[Properties of Compound (37)]
$^1$H-NMR(DMSO-d$_6$, δ ppm): 2.60(3H, s), 5.67(2H, s), 6.59(1H, s), 6.68(1H, d, J=8.1 Hz), 7.05(1H, d, J=1.5 Hz), 7.16(1H, d, J=3.1 Hz), 7.55(2H, m), 7.70(1H, d, J=8.4 Hz), 7.76(1H, s), 7.88(2H, m), 8.12(1H, s).
IR(Nujol): 1622 cm$^{-1}$.
mp: 279–282° C.

EXAMPLE 38
<Synthesis of 6-(1-butanesulfonylcarbamoyl)-1-(2-chloro-4-(2-furyl)benzyl)-2-methylbenzimidazole (38)>

In the same manner as in Example 1, 0.138 g of the title compound were formed from 0.150 g of 6-carboxy-1-(2-chloro-4-(2-furyl)benzyl)-2-methylbenzimidazole and 0.078 g of 1-butanesulfonamide.

[Properties of Compound (38)]
$^1$H-NMR(DMSO-d$_6$, δ ppm): 0.83(3H, t, J=7.5 Hz), 1.37 (2H, m), 1.64(2H, m), 2.51(3H, s), 3.49(2H, t, J=7.7 Hz), 5.60(2H, s), 6.53(1H, d, J=8.2 Hz), 6.59(1H, m), 7.05(1H, d, J=3.3 Hz), 7.54(1H, d, J=8.1 Hz), 7.68(1H, d, J=8.5 Hz), 7.75(1H, s), 7.80(1H, dd, J=1.4 and 8.5 Hz), 7.87(1H, d, J=1.4 Hz), 8.13(1H, s), 11.91(1H, brs).
IR(Nujol): 1683 cm$^{-1}$.
mp: 238.6–241.2° C.

EXAMPLE 39
<Synthesis of 1-(2-chloro-4-(2-furyl)benzyl)-2-methyl-6-((E)-1-pent-1-enesulfonylcarbamoyl)benzimidazole (39)>

In the same manner as in Example 1, 0.135 g of the title compound were formed from 0.150 g of 6-carboxy-1-(2-chloro-4-(2-furyl)benzyl)-2-methylbenzimidazole and 0.085 g of (E)-pent-1-enesulfonamide.

[Properties of Compound (39)]
$^1$H-NMR(DMSO-d$_6$, δ ppm): 0.84(3H, t, J=7.4 Hz), 1.42 (2H, m), 2.21(2H, m), 2.50(3H, s), 5.60(2H, s), 6.51(1H, d, J=8.2 Hz), 6.60(1H, m), 6.75(1H, d, J=15.1, Hz), 6.86(1H, m), 7.05(1H, d, J=3.3 Hz), 7.54(1H, d, J=8.1 Hz), 7.67(1H, d, J=8.5 Hz), 7.76(2H, m), 7.88(1H, s), 8.11(1H, s), 12.02 (1H, brs).
IR(Nujol): 1672 cm$^{-1}$.
mp: 222–228° C.

EXAMPLE 40
<Synthesis of 1-(2-chloro-4-phenylbenzyl)-2-(methyloxymethyl)-6-(1-pentanesulfonylcarbamoyl)benzimidazole (40)>

In the same manner as in Example 1, 0.22 g of the title compound were formed from 0.20 g of 6-carboxy-1-(2-chloro-4-phenylbenzyl)-2-(methyloxymethyl)benzimidazole and 0.10 g of 1-pentanesulfonamide.

[Properties of Compound (40)]
$^1$H-NMR(DMSO-d$_6$, δ ppm): 0.78(3H, dt, J=7.3 and 1.2 Hz), 1.19–1.27(2H, m), 1.30–1.36(2H, m), 1.62–1.70(2H, m), 3.31(3H, s), 3.49(2H, t, J=7.7 Hz), 4.70(2H, s), 5.70(2H, s), 6.51(1H, d, J=8.2 Hz), 7.35–7.39(1H, m), 7.42–7.46(2H, m), 7.51(1H, dd, J=8.1 and 1.5 Hz), 7.64–7.66(2H, m), 7.80(1H, d, J=8.7 Hz), 7.84–7.87(2H, m), 8.17(1H, s), 11.96(1H, brs).
IR(Nujol): 1694 cm$^{-1}$.
mp: 178.0–179.9° C.

EXAMPLE 41
<Synthesis of 1-(2-chloro-4-phenylbenzyl)-6-((4-methylbenzene)sulfonylcarbamoyl)-2-(methyloxymethyl)benzimidazole (41)>

In the same manner as in Example 1, 0.17 g of the title compound were formed from 0.20 g of 6-carboxy-1-(2-chloro-4-phenylbenzyl)-2-(methyloxymethyl)benzimidazole and 0.11 g of (4-methylbenzene)sulfonamide.

[Properties of Compound (41)]
$^1$H-NMR(DMSO-d$_6$, δ ppm): 2.35(3H, s), 3.23(3H, s), 4.67(2H, s), 5.69(2H, s), 6.48(1H, d, J=8.1 Hz), 7.36–7.40 (3H, m), 7.42–7.47(2H, m), 7.50(1H, dd, J=8.1 and 1.8 Hz), 7.64–7.67(2H, m), 7.77(2H, s), 7.83–7.86(3H, m), 8.11(1H, s).
IR(Nujol): 1694 cm$^{-1}$.
mp: 197.9–201.1° C.

EXAMPLE 42
<Synthesis of 1-(2-chloro-4-(1-pentyn-1-yl)benzyl)-2-methyl-6-(1-pentanesulfonylcarbamoyl)benzimidazole (42)>

In the same manner as in Example 1, 167 mg of the title compound were formed as colorless crystals from 222 mg of 6-carboxy-1-(2-chloro-4-(1-pentyn-1-yl)benzyl)-2-methylbenzimidazole and 137 mg of 1-pentanesulfonamide.

[Properties of Compound (42)]
$^1$H-NMR (CDCl$_3$, δ ppm): 0.88 (3H, t, J=7 Hz), 1.02 (3H, t, J=7 Hz), 1.24–1.69 (6H, m), 1.80–1.93 (2H, m), 2.36 (2H, t, J=7 Hz), 2.58 (3H, s), 3.51–3.62 (2H, m), 5.43 (2H, s), 6.28 (1H, d, J=8 Hz), 7.10 (1H, dd, J=1, 8 Hz), 7.50 (1H, d, J=31 Hz), 7.67 (1H, dd, J=1, 8 Hz), 7.75–7.83 (2H, m).
MASS(ESI): m/z 498 (M−1).

EXAMPLE 43
<Synthesis of 1-(2-chloro-4-(1-pentyn-1-yl)benzyl)-2-methyl-6-((4-methylbenzene)sulfonylcarbamoyl)benzimidazole (43)>

In the same manner as in Example 1, 231 mg of the title compound were formed as colorless crystals from 210 mg of 6-carboxy-1-(2-chloro-4-(1-pentyn-1-yl)benzyl)-2-methylbenzimidazole and 147 mg of (4-methylbenzene) sulfonamide.

[Properties of Compound (43)]
$^1$H-NMR (CDCl$_3$, δ ppm): 1.02 (3H, t, J=7 Hz), 1.55–1.66 (2H, m), 2.36 (2H, t, J=7Hz), 2.42 (3H, s), 2.53 (3H, s), 5.36 (2H, s), 6.19 (1H, d, J=8 Hz), 7.03 (1H, d, J=8 Hz), 7.32 (2H, d, J=8 Hz), 7.44 (1H, s), 7.64 (1H, d, J=8 Hz), 7.70 (1H, d, J=8 Hz), 7.77 (1H, s), 8.00 (2H, d, J=8 Hz).
MASS(ESI): m/z 518 (M−1).

EXAMPLE 44
<Synthesis of 1-(2-chloro-4-(1-hexyn-1-yl)benzyl)-2-methyl-6-(1-pentanesulfonylcarbamoyl)benzimidazole (44)>

In the same manner as in Example 1, 228 mg of the title compound were formed as colorless crystals from 250 mg of 6-carboxy-1-(2-chloro-4-(1-hexyn-1-yl)benzyl)-2-methylbenzimidazole and 149 mg of 1-pentanesulfonamide.

[Properties of Compound (44)]
$^1$H-NMR (CDCl$_3$, δ ppm): 0.82–0.99(6H, m), 1.25–1.91 (10H, m), 2.39(2H, t, J=7 Hz), 3.49–3.60(2H, m), 5.42(2H, s), 6.27(1H, d, J=8 Hz), 7.08(1H, brd, J=8 Hz), 7.49(1H, brs), 7.71(1H, d, J=8 Hz), 7.75(1H, d, J=8 Hz), 7.83(1H, brs).
MASS(ESI): m/z 514 (M+1).
mp 190–191° C.

EXAMPLE 45
<Synthesis of 1-(2-chloro-4-(1-hexyn-1-yl)benzyl)-2-methyl-6-((4-methylbenzene)sulfonylcarbamoyl)benzimidazole (45)>

In the same manner as in Example 1, 290 mg of the title compound were formed as colorless crystals from 250 mg of 6-carboxy-1-(2-chloro-4-(1-hexyn-1-yl)benzyl)-2-methylbenzimidazole and 169 mg of (4-methylbenzene) sulfonamide.

[Properties of Compound (45)]
$^1$H-NMR (CDCl$_3$, δ ppm): 0.94(3H, t, J=7 Hz), 1.37–1.65 (4H, m), 2.38(2H, t, J=7 Hz), 2.41(3H, s), 2.53(3H, s), 5.36(2H, s), 6.19(1H, d, J=8 Hz), 7.02(1H, dd, J=8, 1 Hz), 7.32(2H, d, J=8 Hz), 7.44(1H, brs), 7.65(1H, dd, J=8, 1 Hz), 7.71(1H, d, J=8 Hz), 7.78(1H, brs), 8.00(2H, d, J=8 Hz).
MASS(ESI): m/z 534 (M+1).
mp: 213–214° C.

EXAMPLE 46

<Synthesis of 1-(2-chloro-4-(1-heptyn-1-yl)benzyl)-2-methyl-6-(1-pentanesulfonylcarbamoyl)benzimidazole (46)>

In the same manner as in Example 1, 175 mg of the title compound were formed as colorless crystals from 245 mg of 6-carboxy-1-(2-chloro-4-(1-heptyn-1-yl)benzyl)-2-methylbenzimidazole and 141 mg of 1-pentanesulfonamide.

[Properties of Compound (46)]

$^1$H-NMR (CDCl$_3$, δ ppm): 0.88 (3H, t, J=7 Hz), 0.91 (3H, t, J=7 Hz), 1.24–1.66 (10H, m), 1.78–1.94 (2H, m), 2.38 (2H, t, J=7 Hz), 2.58 (3H, s), 3.50–3.61 (2H, m), 5.43 (2H, s), 6.28 (1H, d, J=8 Hz), 7.10 (1H, d, J=8 Hz), 7.50 (1H, d, J=1 Hz), 7.67 (1H, dd, J=1, 8 Hz), 7.75–7.83 (2H, m).

MASS(ESI): m/z 526 (M−1).

EXAMPLE 47

<Synthesis of 1-(2-chloro-4-(1-heptyn-1-yl)benzyl)-2-methyl-6-((4-methylbenzene)sulfonylcarbamoyl)benzimidazole (47)>

In the same manner as in Example 1, 228 mg of the title compound were formed as colorless crystals from 225 mg of 6-carboxy-1-(2-chloro-4-(1-heptyn-1-yl)benzyl)-2-methylbenzimidazole and 146 mg of (4-methylbenzene)sulfonamide.

[Properties of Compound (47)]

$^1$H-NMR (CDCl$_3$, δ ppm: 0.91 (3H, t, J=7 Hz), 1.25–1.47 (4H, m), 1.53–1.65 (2H, m), 2.38 (2H, t, J=7 Hz), 2.42 (3H, s), 2.54 (3H, s), 5.36 (2H, s), 6.20 (1H, d, J=8 Hz), 7.05 (1H, dd, J=1, 8 Hz), 7.33 (2H, d, J=8 Hz), 7.45 (1H, d, J=1 Hz), 7.63 (1H, dd, J=1, 8 Hz), 7.70–7.79 (2H, m), 8.01 (2H, d, J=8 Hz).

MASS(ESI): m/z 546 (M−1).

EXAMPLE 48

<Synthesis of 1-(2-chloro-4-ethylbenzyl)-2-methyl-6-(1-pentanesulfonylcarbamoyl)benzimidazole (48)>

In the same manner as in Example 1, 204 mg of the title compound were formed as colorless crystals from 235 mg of 6-carboxy-1-(2-chloro-4-ethylbenzyl)-2-methylbenzimidazole and 162 mg of 1-pentanesulfonamide.

[Properties of Compound (48)]

$^1$H-NMR (CDCl$_3$, δ ppm): 0.88 (3H, t, J=7 Hz), 1.21 (3H, t, J=7 Hz), 1.25–1.48 (4H, m), 1.81–1.92 (2H, m), 2.57–2.65 (5H, m), 3.55–3.60 (2H, m), 5.42 (2H, s), 6.29 (1H, d, J=8 Hz), 6.93 (1H, dd, J=1, 8 Hz), 7.32 (1H, s), 7.67 (1H, dd, J=1, 8 Hz), 7.77–7.80 (2H, m).

MASS(ESI): m/z 460 (M−1).

EXAMPLE 49

<Synthesis of 1-(2-chloro-4-ethylbenzyl)-2-methyl-6-((4-methylbenzene)sulfonylcarbamoyl)benzimidazole (49)>

In the same manner as in Example 1, 235 mg of the title compound were formed as colorless crystals from 230 mg of 6-carboxy-1-(2-chloro-4-ethylbenzyl)-2-methylbenzimidazole and 180 mg of (4-methylbenzene)sulfonamide.

[Properties of Compound (49)]

$^1$H-NMR(CDCl$_3$, δ ppm): 1.20 (3H, t, J=7 Hz), 2.42 (3H, s), 2.56–2.64 (5H, m), 5.36 (2H, s), 6.22 (1H, d, J=8 Hz), 6.89 (1H, d, J=8 Hz), 7.30–7.35 (3H, m), 7.59 (1H, dd, J=1, 8 Hz), 7.72–7.75 (2H, m), 8.03 (2H, d, J=8 Hz).

MASS(ESI): m/z 480 (M−1).

EXAMPLE 50

<Synthesis of 1-(4-n-butyl-2-chlorobenzyl)-2-methyl-6-(1-pentanesulfonylcarbamoyl)benzimidazole (50)>

In the same manner as in Example 1, 0.340 g of the title compound were formed from 0.400 g of 1-(4-n-butyl-2-chlorobenzyl)-6-carboxy-2-methylbenzimidazole and 0.219 g of 1-pentanesulfonamide.

[Properties of Compound (50)]

$^1$H-NMR(DMSO-d$_6$, δ ppm): 0.80(3H, t, J=7.3 Hz), 0.85 (3H, t, J=7.4 Hz), 1.21–1.30(4H, m), 1.31–1.38(2H, m), 1.46–1.53(2H, m), 1.63–1.71(2H, m), 2.48(3H, s), 2.53(2H, t, J=7.5 Hz), 3.49(2H, t, J=7.7 Hz), 5.55(2H, s), 6.36(1H, d, J=8.0 Hz), 7.04(1H, d, J=8.0 Hz), 7.39(1H, s), 7.67(1H, d, J=8.5 Hz), 7.79(1H, d, J=8.4 Hz), 8.10(1H, s), 11.85(1H, brs).

IR(Nujol): 1667 cm$^{-1}$.

mp: 176.8–177.7° C.

EXAMPLE 51

<Synthesis of 1-(4-n-butyl-2-chlorobenzyl)-2-methyl-6-((4-methylbenzene)sulfonylcarbamoyl)benzimidazole (51)>

In the same manner as in Example 1, 0.525 g of the title compound were formed from 0.400 g of 1-(4-n-butyl-2-chlorobenzyl)-6-carboxy-2-methylbenzimidazole and 0.247 g of (4-methylbenzene)sulfonamide.

[Properties of Compound (51)]

$^1$H-NMR(DMSO-d$_6$, δ ppm): 0.85(3H, t, J=7.3 Hz), 1.21–1.30(2H, m), 1.46–1.53(2H, m), 2.37(3H, s), 2.49(3H, s), 2.53(2H, t, J=7.8 Hz), 5.53(2H, s), 6.33(1H, d, J=7.9 Hz), 7.03(1H, d, J=7.9 Hz), 7.37–7.41(3H, m), 7.62(1H, d, J=8.5 Hz), 7.70(1H, d, J=8.6 Hz), 7.85(2H, d, J=8.3 Hz), 8.04(1H, s), 12.33(1H, brs).

mp: 198.1–198.8° C.

EXAMPLE 52

<Synthesis of 1-(2-chloro-4-(1-pentyl)benzyl)-2-methyl-6-(1-pentanesulfonylcarbamoyl)benzimidazole (52)>

In the same manner as in Example 1, 170 mg of the title compound were formed as colorless crystals from 220 mg of 6-carboxy-1-(2-chloro-4-(1-pentyl)benzyl)-2-methylbenzimidazole and 135 mg of 1-pentanesulfonamide.

[Properties of Compound (52)]

$^1$H-NMR (CDCl$_3$, δ ppm): 0.84–0.95 (6H, m), 1.22–1.67 (10H, m), 1.80–1.94 (2H, m), 2.55 (2H, t, J=7 Hz), 2.60 (3H, s), 3.50–3.63 (2H, m), 5.42 (2H, s), 6.30 (1H, d, J=8 Hz), 6.90 (1H, d, J=8 Hz), 7.30 (1H, s), 7.66 (1H, dd, J=1, 8 Hz), 7.75–7.84 (2H, m).

MASS(ESI): m/z 502 (M−1).

EXAMPLE 53

<Synthesis of 1-(2-chloro-4-(1-pentyl)benzyl)-2-methyl-6-((4-methylbenzene)sulfonylcarbamoyl)benzimidazole (53)>

The title compound (216 mg) was formed as colorless crystals from 211 mg of 6-carboxy-1-(2-chloro-4-(1-pentyl)benzyl)-2-methylbenzimidazole, and 146 mg of (4-methylbenzene)sulfonamide.

[Properties of Compound (53)]

$^1$H-NMR (DMSO-d$_6$, δ ppm): 0.84 (3H, t, J=7 Hz), 1.16–1.35 (4H, m), 1.45–1.60 (2H, m), 2.38 (3H, s), 2.44–2.60 (5H, m), 5.55 (2H, s), 6.33 (1H, d, J=8 Hz), 7.05 (1H, d, J=8 Hz), 7.40 (2H, s), 7.43 (1H, s), 7.64 (1H, d, J=98 Hz), 7.71 (1H, d, J=8 Hz), 7.87 (2H, d, J=8 Hz), 8.05 (1H, s).

MASS(ESI): m/z 522 (M−1).

EXAMPLE 54
<Synthesis of 6-(1-butanesulfonylcarbamoyl)-1-(2-chloro-4-(1-hexyl)benzyl)-2-methylbenzimidazole (54)>

In the same manner as in Example 1, 240 mg of the title compound were formed as colorless crystals from 260 mg of 6-carboxy-1-(2-chloro-4-(1-hexyl)benzyl)methylbenzimidazole and 167 mg of 1-butanesulfonamide.

[Properties of Compound (54)]
$^1$H-NMR (CDCl$_3$, δ ppm): 0.87 (3H, t, J=7 Hz), 0.95 (3H, t, J=7 Hz), 1.28 (6H, brs), 1.40–1.61 (4H, m), 1.80–1.92 (2H, m), 2.55 (2H, t, J=7 Hz), 2.60 (3H, s), 3.55–3.64 (2H, m), 5.42 (2H, s), 6.30 (1H, d, J=8 Hz), 6.90 (1H, d, J=8 Hz), 7.30 (1H, s), 7.66 (1H, d, J=8 Hz), 7.77–7.83 (2H, m).

MASS(ESI): m/z 504 (M+1).

EXAMPLE 55
<Synthesis of 1-(2-chloro-4-(1-hexyl)benzyl)-2-methyl-6-(1-pentanesulfonylcarbamoyl)benzimidazole (55)>

In the same manner as in Example 1, 187 mg of the title compound were formed as colorless crystals from 250 mg of 6-carboxy-1-(2-chloro-4-(1-hexyl)benzyl)-2-methylbenzimidazole and 177 mg of 1-pentanesulfonamide.

[Properties of Compound (55)]
$^1$H-NMR (CDCl$_3$, δ ppm): 0.83–0.95 (6H, m), 1.22–1.64 (12H, m), 1.81–1.94 (2H, m), 2.56 (2H, t, J=7 Hz), 2.60 (3H, s), 3.53–3.63 (2H, m), 5.42 (2H, s), 6.29 (1H, d, J=8 Hz), 6.90 (1H, d, J=8 Hz), 7.30 (1H, s), 7.66 (1H, d, J=8 Hz), 7.77–7.84 (2H, m).

MASS(ESI): m/z 518 (M+1).

EXAMPLE 56
<Synthesis of 1-(2-chloro-4-(1-hexyl)benzyl)-2-methyl-6-((E)-1-pent-1-enesulfonylcarbamoyl)benzimidazole (56)>

In the same manner as in Example 1, 197 mg of the title compound were formed as colorless crystals from 250 mg of 6-carboxy-1-(2-chloro-4-(1-hexyl)benzyl)-2-methylbenzimidazole and 160 mg of (E)-1-pent-1-enesulfonamide.

[Properties of Compound (56)]
$^1$H-NMR (CDCl$_3$, δ ppm): 0.87 (3H, t, J=7 Hz), 0.94 (3H, t, J=7 Hz), 1.28 (6H, brs), 1.45–1.66 (4H, m), 2.28 (2H, q, J=7 Hz), 2.55 (2H, t, J=7 Hz), 2.59 (3H, s), 5.41 (2H, s), 6.26 (1H, d, J=8 Hz), 6.63 (1H, d, J=15 Hz), 6.90 (1H, d, J=8 Hz), 7.05–7.19 (1H, m), 7.30 (1H, s), 7.64 (1H, d, J=8 Hz), 7.75–7.82 (2H, m).

MASS(ESI): m/z 516 (M+1).

EXAMPLE 57
<Synthesis of 1-(2-chloro-4-(1-hexyl)benzyl)-2-methyl-6-((E)-(2-phenylethene)sulfonylcarbamoyl)benzimidazole (57)>

In the same manner as in Example 1, 251 mg of the title compound were formed as colorless crystals from 230 mg of 6-carboxy-1-(2-chloro-4-(1-hexyl)benzyl)-2-methylbenzimidazole and 164 mg of ((E)-2-phenylethene)sulfonamide.

[Properties of Compound (57)]
$^1$H-NMR (DMSO-d$_6$, δ ppm): 0.83 (3H, t, J=7 Hz), 1.23 (6H, brs), 1.41–1.60 (2H, m), 2.42–2.60 (5H, m), 5.55 (2H, s), 6.34 (1H, d, J=8 Hz), 7.05 (1H, d, J=8 Hz), 7.38–7.84 (10H, m), 8.12 (1H, s).

MASS(ESI): m/z 548 (M−1).

EXAMPLE 58
<Synthesis of 1-(2-chloro-4-(1-hexyl)benzyl)-2-methyl-6-((5-chloro-2-thiophene)sulfonylcarbamoyl)benzimidazole (58)>

In the same manner as in Example 1, 199 mg of the title compound were formed as colorless crystals from 230 mg of 6-carboxy-1-(2-chloro-4-(1-hexyl)benzyl)-2-methylbenzimidazole and 177 mg of (5-chloro-2-thiophene)sulfonamide.

[Properties of Compound (58)]
$^1$H-NMR (DMSO-d$_6$, δ ppm): 0.83 (3H, t, J=7 Hz), 1.24 (6H, brs), 1.45–1.61 (2H, m), 2.46–2.66 (5H, m), 5.64 (2H, s), 6.53 (1H, d, J=8 Hz), 7.07 (1H, d, J=8 Hz), 7.18 (1H, d, J=4 Hz), 7.41 (1H, d, J=1 Hz), 7.57 (1H, d, J=4 Hz), 7.70 (1H, d, J=8 Hz), 7.90 (1H, d, J=8 Hz), 8.09 (1H, s).

MASS(ESI): m/z 564 (M+1).

EXAMPLE 59
<Synthesis of 1-(2-chloro-4-(1-heptyl)benzyl)-2-methyl-6-(1-pentanesulfonylcarbamoyl)benzimidazole (59)>

In the same manner as in Example 1, 195 mg of the title compound were formed as colorless crystals from 220 mg of 6-carboxy-1-(2-chloro-4-(1-heptyl)benzyl)-2-methylbenzimidazole and 125 mg of 1-pentanesulfonamide.

[Properties of Compound (59)]
$^1$H-NMR (CDCl$_3$, δ ppm): 0.82–0.94 (6H, m), 1.20–1.50 (14H, m), 1.80–1.94 (2H, m), 2.55 (2H, t, J=7 Hz), 2.60 (3H, s), 3.52–3.62 (2H, m), 5.42 (2H, s), 6.29 (1H, d, J=8 Hz), 6.90 (1H, dd, J=1, 8 Hz), 7.30 (1H, s), 7.67 (1H, dd, J=1, 8 Hz), 7.75–7.83 (2H, m).

MASS(ESI): m/z 530 (M−1).

EXAMPLE 60
<Synthesis of 1-(2-chloro-4-(1-heptyl)benzyl)-2-methyl-6-((4-methylbenzene)sulfonylcarbamoyl)benzimidazole (60)>

In the same manner as in Example 1, 194 mg of the title compound were formed as colorless crystals from 200 mg of 6-carboxy-1-(2-chloro-4-(1-heptyl)benzyl)-2-methylbenzimidazole and 129 mg of (4-methylbenzene)sulfonamide.

[Properties of Compound (60)]
$^1$H-NMR (CDCl$_3$, δ ppm): 0.87 (3H, t, J=7 Hz), 1.17–1.37 (8H, m), 1.49–1.63 (2H, m), 2.42 (3H, s), 2.46–2.60 (5H, m), 5.35 (2H, s), 6.20 (1H, d, J=8 Hz), 6.85 (1H, dd, J=1, 8 Hz), 7.25 (1H, d, J=1 Hz), 7.32 (2H, d, J=8 Hz), 7.62 (1H, dd, J=1, 8 Hz), 7.70 (1H, d, J=8 Hz), 7.77 (1H, s), 8.01 (2H, d, J=8 Hz).

MASS(ESI): m/z 550 (M−1).

EXAMPLE 61
<Synthesis of 6-(1-butanesulfonylcarbamoyl)-1-(2-chloro-4-(trifluoromethyl)benzyl)-2-methylbenzimidazole (61)>

In the same manner as in Example 1, 218 mg of the title compound were formed as colorless crystals from 230 mg of 6-carboxy-1-(2-chloro-4-(trifluoromethyl)benzyl)-2-methylbenzimidazole and 128 mg of 1-butanesulfonamide.

[Properties of Compound (61)]
$^1$H-NMR (CDCl$_3$, δ ppm): 0.93 (3H, t, J=7 Hz), 1.42–1.54 (2H, m), 1.79–1.90 (2H, m), 2.60 (3H, s), 3.55–3.60 (2H, m), 5.50 (2H, s), 6.46 (1H, d, J=8 Hz), 7.38 (1H, d, J=8 Hz), 7.71 (1H, dd, J=1, 8 Hz), 7.78–7.84 (3H, m).

MASS(ESI): m/z 486 (M−1).

EXAMPLE 62
<Synthesis of 6-(benzenesulfonylcarbamoyl)-1-(2-chloro-4-(trifluoromethyl)benzyl)-2-methylbenzimidazole (62)>

In the same manner as in Example 1, 217 mg of the title compound were formed as colorless crystals from, 220 mg of 6-carboxy-1-(2-chloro-4-(trifluoromethyl)benzyl)-2-methylbenzimidazole and 141 mg of benzenesulfonamide.

[Properties of Compound (62)]
$^1$H-NMR (CDCl$_3$, δ ppm): 2.57 (3H, s), 5.44 (2H, s), 6.39 (1H, d, J=8 Hz), 7.32 (1H, d, J=8 Hz), 7.52–7.57 (2H, m), 7.62–7.68 (2H, m), 7.73–7.78 (3H, m), 8.14 (2H, d, J=8 Hz).

MASS(ESI): m/z 506 (M−1).

EXAMPLE 63

<Synthesis of 1-(2-chloro-4-(trifluoromethyl)benzyl)-2-methyl-6-((3-methylbenzene)sulfonylcarbamoyl)benzimidazole (63)>

In the same manner as in Example 1, 223 mg of the title compound were formed as colorless crystals from 220 mg of 6-carboxy-1-(2-chloro-4-trifluoromethylbenzyl)-2-methylbenzimidazole and 358 mg of (3-methylbenzene)sulfonamide.

[Properties of Compound (63)]

$^1$H-NMR(CDCl$_3$-MeOH, δ ppm): 2.43(3H, s), 2.56(3H, s), 5.47(2H, s), 6.43(1H, d, J=8 Hz), 7.35(1H, d, J=8 Hz), 7.40–7.43(2H, m), 7.72–7.82(4H, m), 7.88–7.94(2H, m).

MASS(ESI); m/z 520 (M−H).

mp: 275–277° C.

EXAMPLE 64

<Synthesis of 1-(2-chloro-4-(trifluoromethyl)benzyl)-2-methyl-6-((E)-(2-phenylethene)sulfonylcarbamoyl)benzimidazole (64)>

In the same manner as in Example 1, 226 mg of the title compound were formed as colorless crystals from 220 mg of 6-carboxy-1-(2-chloro-4-(trifluoromethyl)benzyl)-2-methylbenzimidazole and 383 mg of (E)-(2-phenylethene)sulfonamide.

[Properties of Compound (64)]

$^1$H-NMR(CDCl$_3$-MeOH, δ ppm): 2.58(3H, s), 5.49(2H, s), 6.45(1H, d, J=8 Hz), 7.17(1H, d, J=15 Hz), 7.36–7.44 (4H, m), 7.52–7.55(2H, m), 7.71–7.85(5H, m).

MASS(ESI): m/z 532 (M−H).

mp: 285–286° C.

EXAMPLE 65

<Synthesis of 1-(2-chloro-4-(trifluoromethyl)benzyl)-2-methyl-6-((5-chloro-2-thiophene)sulfonylcarbamoyl)benzimidazole (65)>

In the same manner as in Example 1, 210 mg of the title compound were formed as colorless crystals from 220 mg of 6-carboxy-1-(2-chloro-4-(trifluoromethyl)benzyl)-2-methylbenzimidazole and 413 mg of (5-chloro-2-thiophene)sulfonamide.

[Properties of Compound (65)]

$^1$H NMR(CDCl$_3$-MeOH, δ ppm): 2.60 (3H, s), 5.55(2H, s), 6.52(1H, d, J=8 Hz), 6.98(1H, d, J=3 Hz), 7.40(1H, d, J=8 Hz), 7.72–7.80(3H, m), 7.86(1H, d, J=8 Hz), 7.92(1H, s).

MASS(ESI): m/z 546 (M−1).

mp: >300° C.

EXAMPLE 66

<Synthesis of 1-(2-chloro-4-(N-methyl-N-(1-pentyl)amino)benzyl)-2-methyl-6-(1-pentanesulfonylcarbamoyl)benzimidazole (66)>

In the same manner as in Example 1, 130 mg of the title compound were formed as colorless crystals from 170 mg of 6-carboxy-1-(2-chloro-4-(N-methyl-N-(1-pentyl)amino)benzyl)-2-methylbenzimidazole and 96 mg of 1-pentanesulfonamide.

[Properties of Compound (66)]

$^1$H-NMR (CDCl$_3$, δ ppm: 0.89 (3H, t, J=7 Hz), 0.89 (3H, t, J=7 Hz), 1.20–1.70 (10H, m), 1.80–1.94 (2H, m), 2.61 (3H, s), 2.89 (3H, s), 3.24 (2H, t, J=7 Hz), 3.51–3.62 (2H, m), 5.35 (2H, s), 6.30–6.42 (2H, m), 6.70 (1H, d, J=1 Hz), 7.67 (1H, dd, J=1, 8 Hz), 7.74 (1H, d, J=8 Hz), 7.84 (1H, d, J=1 Hz).

MASS(ESI): m/z 531 (M−1).

EXAMPLE 67

<Synthesis of 1-(2-chloro-4-(N-methyl-N-(1-pentyl)amino)benzyl)-2-methyl-6-((4-methylbenzene)sulfonylcarbamoyl)benzimidazole (67)>

In the same manner as in Example 1, 22 mg of the title compound were formed as a colorless powder from 125 mg of 6-carboxy-1-(2-chloro-4-(N-methyl-N-(1-pentyl)amino)benzyl)-2-methylbenzimidazole and 80 mg of (4-methylbenzene)sulfonamide.

[Properties of Compound (67)]

$^1$H-NMR (CDCl$_3$, δ ppm): 0.89 (3H, t, J=7 Hz), 1.19–1.40 (4H, m), 1.45–1.60 (2H, m), 2.42 (3H, s), 2.56 (3H, s), 2.88 (3H, s), 3.23 (2H, t, J=7 Hz), 5.27 (2H, s), 6.25 (1H, d, J=8 Hz), 6.32 (1H, dd, J=1, 8 Hz), 6.66 (1H, d, J=1 Hz), 7.32 (2H, d, J=8 Hz), 7.57–7.69 (2H, m), 7.81 (1H, s), 8.01 (2H, d, J=8 Hz).

MASS(ESI): m/z 553 (M+1).

EXAMPLE 68

<Synthesis of 1-(4-(N-1-butyrylamino)-2-chlorobenzyl)-2-methyl-6-(1-pentanesulfonylcarbamoyl)benzimidazole (68)>

In the same manner as in Example 1, 158 mg of the title compound were formed as colorless crystals from 210 mg of 1-(4-(N-1-butyrylamino)-2-chlorobenzyl)-6-carboxy-2-methylbenzimidazole and 123 mg of 1-pentanesulfonamide.

[Properties of Compound (68)]

$^1$H-NMR (DMSO-d$_6$, δ ppm): 0.81 (3H, t, J=7 Hz), 0.89 (3H, t, J=7 Hz), 1.18–1.44 (4H, m), 1.50–1.76 (4H, m), 2.26 (2H, t, J=7 Hz), 2.50 (3H, overlapped with DMSO-d$_6$), 3.50 (2H, t, J=7 Hz), 5.54 (2H, s), 6.50 (1H, d, J=8 Hz), 7.28 (1H, dd, J=1, 8 Hz), 7.67 (1H, d, J=8 Hz), 7.80 (1H, dd, J=1, 8 Hz), 8.00 (1H, d, J=1 Hz), 8.11 (1H, s).

MASS(ESI): m/z 517 (M−1).

EXAMPLE 69

<Synthesis of 1-(4-(N-1-butyrylamino)-2-chlorobenzyl)-2-methyl-6-((4-methylbenzene)sulfonylcarbamoyl)benzimidazole (69)>

In the same manner as in Example 1, 102 mg of the title compound were formed as colorless crystals from 190 mg of 1-(4-(N-1-butyrylamino)-2-chlorobenzyl)-6-carboxy-2-methylbenzimidazole and 126 mg of (4-methylbenzene)sulfonamide.

[Properties of Compound (69)]

$^1$H-NMR (CDCl$_3$, δ ppm): 0.98 (3H, t, J=7 Hz), 1.74 (2H, tq, J=7, 7 Hz), 2.32 (2H, t, J=7 Hz), 2.41 (3H, s), 2.55 (3H, s), 5.32 (2H, s), 6.21 (1H, d, J=8 Hz), 7.00 (1H, dd, J=1, 8 Hz), 7.30 (2H, d, J=8 Hz), 7.55–7.66 (2H, m), 7.75 (1H, s), 7.85 (1H, d, J=1 Hz), 7.99 (2H, d, J=8 Hz).

MASS(ESI): m/z 537 (M−1).

EXAMPLE 70

<Synthesis of 1-(2-chloro-4-morpholinobenzyl)-2-methyl-6-((4-methylbenzene)sulfonylcarbamoyl)benzimidazole (70)>

1-(4-bromo-2-chlorobenzyl)-2-methyl-6-((4-methylbenzene)sulfonylcarbamoyl)benzimidazole (250 mg) was dissolved in 3 ml of toluene, to which 63 mg of sodium t-butyrate, 49 mg of morpholine, 2.2 mg of (R)-(+)-2,2'-bis (diphenylphosphino)-1,1'-binaphthyl, and 1.1 mg of tris (dibenzylideneacetone) dipalladium (0) were added in this order in a nitrogen atmosphere, and the solution was stirred at 100° C. for 20 hours. The reaction solution was concentrated under reduced pressure, and water was added thereto. Hydrochloric acid (1 N) was added to the solution to adjust to a pH of 7, and the solution was extracted with a mixture of chloroform and methanol at a ratio of 4:1. The organic layer was washed with saturated brine, dried with anhydrous magnesium sulfate, and then concentrated under reduced pressure. The residue was subjected to silica-gel column chromatography and eluted with a mixture of chloroform and methanol at a ratio of 30:1. The desired fractions were concentrated under reduced pressure. The residue was dissolved in 3.0 ml of N,N-dimethylformamide, and 3.2 ml of water was gradually added thereto in an oil bath at 80° C. The solution was allowed to cool. The crystals precipitated were collected through filtration, and dried under reduced pressure while being heated to give 103 mg of the title compound as pale yellow crystals.

[Properties of Compound (70)]
$^1$H-NMR(CDCl$_3$—MeOH, δ ppm): 2.42(3H, s), 2.56(3H, s), 3.12(4H, t, J=6 Hz), 3.83(4H, t, J=6 Hz), 5.33(2H, s), 6.28(1H, d, J=8 Hz), 6.58(1H, dd, J=8, 2 Hz), 6.95(1H, d, J=2 Hz), 7.29–7.34(3H, m), 7.70(1H, s), 7.82(1H, s), 7.00 (2H, d, J=8 Hz).
MASS(ESI): m/z 537 (M−H).
mp: 239–241° C.

EXAMPLE 71

<Synthesis of 1-(2-chloro-4-morpholinobenzyl)-2-methyl-6-(1-pentanesulfonylcarbamoyl)benzimidazole (71)>

In the same manner as in Example 70, 210 mg of the title compound were formed as pale yellow crystals from 373 mg of 1-(4-bromo-2-chlorobenzyl)-2-methyl-6-(1-pentanesulfonylcarbamoyl)benzimidazole and 352 mg of morpholine.

[(Properties of Compound (71)]
$^1$H-NMR(CDCl$_3$, δ ppm): 0.88(3H, t, J=7 Hz), 1.26–1.47 (4H, m), 1.80–1.90(2H, m), 2.59(3H, s), 3.13(4H, t, J=6 Hz), 3.56(2H, t, J=7 Hz), 3.82(4H, t, J=6 Hz), 3.36(2H, s), 6.35(1H, d, J=8 Hz), 6.60(1H, dd, J=8, 2 Hz), 6.94(1H, d, J=2 Hz), 7.67–7.73(2H, m), 7.84(1H, s).
MASS(ESI): m/z 517 (M−H).
mp: 205–207° C.

EXAMPLE 72

<Synthesis of 1-(2-chloro-4-(methylthio)benzyl)-2-methyl-6-(1-pentanesulfonylcarbamoyl)benzimidazole (72)>

In the same manner as in Example 1, 274 mg of the title compound were formed as colorless crystals from 260 mg of 6-carboxy-1-(2-chloro-4-(methylthio)benzyl)-2-methylbenzimidazole and 170 mg of 1-pentanesulfonamide.

[Properties of Compound (72)]
$^1$H-NMR (CDCl$_3$, δ ppm): 0.88 (3H, t, J=7 Hz), 1.28–1.48 (4H, m), 1.81–1.92 (2H, m), 2.46 (3H, s), 2.60 (3H, s), 3.55–3.60 (2H, m), 5.41 (2H, s), 6.29 (1H, d, J=8 Hz), 6.95 (1H, dd, J=1, 8 Hz), 7.32 (1H, d, J=1 Hz), 7.67 (1H, dd, J=1, 8 Hz), 7.76–7.81 (2H, m).
MASS(ESI): m/z 478 (M−1).

EXAMPLE 73

<Synthesis of 1-(2-chloro-4-(methylthio)benzyl)-2-methyl-6-((4-methylbenzene)sulfonylcarbamoyl)benzimidazole (73)>

In the same manner as in Example 1, 267 mg of the title compound were formed as colorless crystals from 250 mg of 6-carboxy-1-(2-chloro-4-(methylthio)benzyl)-2-methylbenzimidazole and 185 mg of (4-methylbenzene)sulfonamide.

[Properties of Compound (73)]
$^1$H-NMR (DMSO-d$_6$, δ ppm): 2.38 (3H, s), 2.46 (3H, s), 2.48 (3H, s), 5.54 (2H, s), 6.36 (1H, d, J=8 Hz), 7.11 (1H, dd, J=1, 8 Hz), 7.40–7.43 (3H, m), 7.63 (1H, d, J=8 Hz), 7.71 (1H, d, J=8 Hz), 7.87 (2H, d, J=8 Hz), 8.04 (1H, s).
MASS(ESI): m/z 498 (M−1).

EXAMPLE 74

<Synthesis of 1-(2-chloro-4-(trifluoromethyl)benzyl)-2-methyl-6-((N-1-propylaminosulfonyl)carbamoyl)benzimidazole (74)>

In the same manner as in Example 1, 174 mg of the title compound were formed as a white powder from 204 mg of 6-carboxy-1-(2-chloro-4-(trifluoromethyl)benzyl)-2-methylbenzimidazole and 118 mg of N-1-propylsulfamide.

[Properties of Compound (74)]
$^1$H-NMR(DMSO-d$_6$, δ ppm): 0.79(3H, t, J=7 Hz), 1.43 (2H, m), 2.50(3H, s), 2.84(2H, q, J=7 Hz), 5.69(2H, s), 6.59(1H, d, J=8 Hz), 7.63(1H, d, J=8 Hz), 7.69(1H, d, J=8 Hz), 7.69(1H, brs), 7.80(1H, d, J=8 Hz), 8.02(1H, s), 8.08 (1H, s), 11.57(1H, brs).
Mass(ESI): m/e 487 (M−H).
mp: 202–203° C.

EXAMPLE 75

<Synthesis of 1-(2-chloro-4-phenylbenzyl)-2-methyl-6-((N-1-propylaminosulfonyl)carbamoyl)benzimidazole (75)>

In the same manner as in Example 1, 0.238 g of the title compound were formed from 0.200 g of 6-carboxy-1-(2-chloro-4-phenylbenzyl)-2-methylbenzimidazole and 0.122 g of N-1-propylsulfamide.

[Properties of Compound (75)]
$^1$H-NMR(DMSO-d$_6$, δ ppm): 0.77(3H, t, J=7.4 Hz), 1.38–1.46(2H, m), 2.52(3H, s), 2.84(2H, d, J=6.7 Hz), 5.63(2H, s), 6.52(1H, d, J=8.2 Hz), 7.37(1H, t, J=7.3 Hz), 7.44(2H, t, J=7.3 Hz), 7.53(1H, dd, J=8.2 and 1.7 Hz), 7.62–7.68(4H, m), 7.80(1H, dd, J=8.5 and 1.5 Hz), 7.85(1H, d, J=1.6 Hz), 8.12(1H, s), 11.61(1H, brs).
IR(Nujol): 1661 cm$^{-1}$.
mp: 193.5–193.8° C.

EXAMPLE 76

<Synthesis of 6-((N-1-butylaminosulfonyl)carbamoyl)-1-(2-chloro-4-phenylbenzyl)-2-methylbenzimidazole (76)>

In the same manner as in Example 1, 0.222 g of the title compound were formed from 0.200 g of 6-carboxy-1-(2-chloro-4-phenylbenzyl)-2-methylbenzimidazole and 0.121 g of N-1-butylsulfamide.

[Properties of Compound (76)]
$^1$H-NMR(DMSO-d$_6$, δ ppm): 0.74(3H, t, J=7.3 Hz), 1.18–1.24(2H, m), 1.35–1.42(2H, m), 2.52(3H, s), 2.87(2H, q, J=6.6 Hz), 5.63(2H, s), 6.52(1H, d, J=8.2 Hz), 7.37(1H, t, J=7.1 Hz), 7.45(2H, t, J=7.7 Hz), 7.53(1H, d, J=8.1 Hz), 7.61–7.71(4H, m), 7.79(1H, dd, J=8.6 and 1.4 Hz), 7.85(1H, d, J=1.7 Hz), 8.12(1H, s), 11.61(1H, brs).
IR(Nujol): 1667 cm$^{-1}$.
mp: 187.7–189.0° C.

EXAMPLE 77

<Synthesis of 1-(2-chloro-4-phenylbenzyl)-6-((N-1-hexylaminosulfonyl)carbamoyl)-2-methylbenzimidazole (77)>

In the same manner as in Example 1, 0.159 g of the title compound were formed from 0.125 g of 6-carboxy-1-(2-chloro-4-phenylbenzyl)-2-methylbenzimidazole and 0.084 g of N-1-hexylsulfamide.

[Properties of Compound (77)]
$^1$H-NMR(DMSO-d$_6$, δ ppm): 0.74(3H, t, J=7.1 Hz), 1.09–1.22(6H, m), 1.37–1.43(2H, m), 2.53(3H, s), 2.87(2H, q, J=6.9 Hz), 5.63(2H, s), 6.51(1H, d, J=8.1 Hz), 7.38(1H, t, J=7.2 Hz), 7.45(2H, t, J=7.4 Hz), 7.53(1H, dd, J=8.1 and 1.6 Hz), 7.61–7.71(4H, m), 7.80(1H, dd, J=8.4 and 1.5 Hz), 7.85(1H, d, J=1.7 Hz), 8.12(1H, d, J=1.4 Hz), 11.58(1H, brs).
IR(Nujol): 1661 cm$^{-1}$.
mp: 178.2–180.0° C.

EXAMPLE 78

<Synthesis of 6-((benzylaminosulfonyl)carbamoyl)-1-(2-chloro-4-phenylbenzyl)-2-methylbenzimidazole (78)>

In the same manner as in Example 1, 0.163 g of the title compound were formed from 0.130 g of 6-carboxy-1-(2-chloro-4-phenylbenzyl)-2-methylbenzimidazole and 0.098 g of N-benzylsulfamide.

[Properties of Compound (78)]

$^1$H-NMR(DMSO-d$_6$, δ ppm): 2.53(3H, s), 4.14(2H, d, J=5.9 Hz), 5.62(2H, s), 6.49(1H, d, J=8.1 Hz), 7.06(1H, t, J=7.2 Hz), 7.15(2H, t, J=7.4 Hz), 7.26(2H, d, J=7.3 Hz), 7.38(1H, t, J=7.2 Hz), 7.45(2H, t, J=7.3 Hz), 7.55(1H, d, J=8.2 Hz), 7.65(3H, m), 7.72(1H, d, J=8.6 Hz), 7.87(1H, d, J=1.6 Hz), 7.99(1H, s), 8.31(1H, brt), 11.58(1H, brs).

IR(Nujol): 1650 cm$^{-1}$.

mp: 178.8–180.3° C.

EXAMPLE 79

<Synthesis of 1-(4-bromo-2-chlorobenzyl)-6-((N-ethylaminosulfonyl)carbamoyl)-2-methylbenzimidazole (79)>

In the same manner as in Example 1, 0.13 g of the title compound were formed from 0.20 g of 1-(4-bromo-2-chlorobenzyl)-6-carboxy-2-methylbenzimidazole and 0.08 g of N-ethylsulfamide.

[Properties of Compound (79)]

$^1$H-NMR(DMSO-d$_6$, δ ppm): 1.02(3H, t, J=7.2 Hz), 2.48 (3H, s), 2.91–2.97(2H, m), 5.55(2H, s), 6.39(1H, d, J=8.4 Hz), 7.45(1H, dd, J=8.4 and 2.0 Hz), 7.65(1H, d, J=8.4 Hz), 7.66(1H, brs), 7.78(1H, dd, J=8.4 and 1.7 Hz), 7.85(1H, d, J=2.0 Hz), 8.06(1H, d, J=1.4 Hz), 11.57(1H, brs).

IR(Nujol): 1661 cm$^{-1}$.

mp: 200.7–201.3° C.

EXAMPLE 80

<Synthesis of 1-(4-bromo-2-chlorobenzyl)-2-methyl-6-((N-1-propylaminosulfonyl)carbamoyl )benzimidazole (80)>

In the same manner as in Example 1, 0.12 g of the title compound were formed from 0.25 g of 1-(4-bromo-2-chlorobenzyl)-6-carboxy-2-methylbenzimidazole and 0.10 g of N-1-propylsulfamide.

[Properties of Compound (80)]

$^1$H-NMR(DMSO-d$_6$, δ ppm): 0.79(3H, t, J=7.4 Hz), 1.41–1.48(2H, m), 2.48(3H, s), 2.85(2H, q, J=6.9 Hz), 5.54(2H, s), 6.39(1H, d, J=8.4 Hz), 7.45(1H, dd, J=8.4 and 2.0 Hz), 7.65(1H, d, J=8.5 Hz), 7.68(1H, brs), 7.78(1H, dd, J=8.4 and 1.5 Hz), 7.85(1H, d, J=1.9 Hz), 8.06(1H, d, J=1.4 Hz), 11.57(1H, brs).

IR(Nujol): 1661 cm$^{-1}$.

mp: 198.1–198.7° C.

EXAMPLE 81

<Synthesis of 1-(4-bromo-2-chlorobenzyl)-6-((N-1-butylaminosulfonyl)carbamoyl)-2-methylbenzimidazole (81)>

In the same manner as in Example 1, 0.151 g of the title compound were formed from 0.200 g of 1-(4-bromo-2-chlorobenzyl)-6-carboxy-2-methylbenzimidazole and 0.080 g of N-1-butylsulfamide.

[Properties of Compound (81)]

$^1$H-NMR(DMSO-d$_6$, δ ppm): 0.77(3H, t, J=7.3 Hz), 1.20–1.28(2H, m), 1.37–1.44(2H, m), 2.87–2.92(2H, m), 5.54(2H, s), 6.38(1H, d, J=8.3 Hz), 7.44(1H, d, J=8.3 Hz), 7.66(1H, d, J=8.5 Hz), 7.69(1H, brs), 7.78(1H, d, J=8.5 Hz), 7.86(1H, s), 8.06(1H, s), 11.55(1H, brs).

IR(Nujol): 1661 cm$^{-1}$.

mp: 199.6–200.4° C.

EXAMPLE 82

<Synthesis of 1-(4-bromo-2-chlorobenzyl)-2-methyl-6-((N-1-pentylaminosulfonyl)carbamoyl)benzimidazole (82)>

In the same manner as in Example 1, 0.16 g of the title compound were formed from 0.20 g of 1-(4-bromo-2-chlorobenzyl)-6-carboxy-2-methylbenzimidazole and 0.08 g of N-1-pentylsulfamide.

[Properties of Compound (82)]

$^1$H-NMR(DMSO-d$_6$, δ ppm): 0.76(3H, t, J=6.8 Hz), 1.17–1.22(4H, m), 1.38–1.44(2H, m), 2.49(3H, s), 2.87(2H, q, J=6.9 Hz), 5.54(2H, s), 6.38(1H, d, J=8.4 Hz), 7.44(1H, d, J=8.3 Hz), 7.62–7.71(2H, m), 7.78(1H, d, J=8.4 Hz), 7.85(1H, d, J=1.5 Hz), 8.06(1H, s), 11.55(1H, brs).

IR(Nujol): 1661 cm$^{-1}$.

mp: 194.9–196.0° C.

EXAMPLE 83

<Synthesis of 6-((benzylaminosulfonyl)carbamoyl)-1-(4-bromo-2-chlorobenzyl)-2-methylbenzimidazole (83)>

In the same manner as in Example 1, 0.09 g of the title compound were formed from 0.200 g of 1-(4-bromo-2-chlorobenzyl)-6-carboxy-2-methylbenzimidazole and 0.098 g of N-benzylsulfamide.

[Properties of Compound (83)]

$^1$H-NMR(DMSO-d$_6$, δ ppm): 4.15(2H, d, J=6.0 Hz), 5.54(2H, s), 6.36(1H, d, J=8.4 Hz), 7.08(1H, t, J=7.2 Hz), 7.17(2H, t, J=7.6 Hz), 7.28(2H, d, J=7.8 Hz), 7.47(1H, d, J=8.2 Hz), 7.63(1H, d, J=8.4 Hz), 7.71(1H, d, J=8.5 Hz), 7.86(1H, s), 7.94(1H, s), 8.33(1H, brt), 11.57(1H, brs).

IR(Nujol): 1672 cm$^{-1}$.

mp: 191.1–191.8° C.

EXAMPLE 84

<Synthesis of 6-((N-1-butylaminosulfonyl)carbamoyl)-1-(2-chloro-4-(methyloxy)benzyl)-2-methylbenzimidazole (84)>

In the same manner as in Example 1, 0.16 g of the title compound were formed from 0.18 g of 6-carboxy-1-(2-chloro-4-(methyloxy)benzyl)-2-methylbenzimidazole and 0.126 g of N-1-butylsulfamide.

[Properties of Compound (84)]

$^1$H-NMR(DMSO-d$_6$, δ ppm): 0.77(3H, t, J=7.3 Hz), 1.23 (2H, m), 1.40(2H, m), 1.40(2H, m), 2.49(3H, s), 2.88(2H, m), 3.73(3H, s), 5.50(2H, s), 6.50(1H, d, J=8.7 Hz), 6.82 (1H, dd, J=8.7 and 2.5 Hz), 7.13(1H, d, J=2.5 Hz), 7.64(1H, d, J=8.5 Hz), 7.69(1H, t, J=5.7 Hz), 7.77(1H, dd, J=1.6 and 8.4 Hz), 8.07(1H, s), 11.57(1H, brs).

IR(Nujol): 1667 cm$^{-1}$.

mp: 185–188° C.

EXAMPLE 85

<Synthesis of 1-(2-chloro-4-(ethyloxy)benzyl)-6-((N-ethylaminosulfonyl)carbamoyl)-2-methylbenzimidazole (85)>

In the same manner as in Example 1, 0.086 g of the title compound were formed from 0.150 g of 6-carboxy-1-(2-chloro-4-(ethyloxy)benzyl)-2-methylbenzimidazole and 0.070 g of N-ethylsulfamide.

[Properties of Compound (85)]

$^1$H-NMR(DMSO-d$_6$, δ ppm): 1.03(3H, t, J=7.3 Hz), 1.28 (3H, t, J=6.9 Hz), 2.91–2.97(2H, m), 3.99(2H, q, J=7.0 Hz), 5.49(2H, s), 6.48(1H, d, J=8.6 Hz), 6.81(1H, dd, J=8.9 and 2.5 Hz), 7.11(1H, d, J=2.5 Hz), 7.64(1H, d, J=8.6 Hz), 7.66–7.70(1H, m), 7.77(1H, dd, J=8.6 and 1.5 Hz), 8.08(1H, s), 11.59(1H, brs).

IR(Nujol): 1667 cm$^{-1}$.

mp: 181.4–183.2° C.

EXAMPLE 86

<Synthesis of 1-(2-chloro-4-(ethyloxy)benzyl)-2-methyl-6-((N-1-propylaminosulfonyl)carbamoyl)benzimidazole (86)>

In the same manner as in Example 1, 0.084 g of the title compound were formed from 0.150 g of 6-carboxy-1-(2-chloro-4-(ethyloxy)benzyl)-2-methylbenzimidazole and 0.065 g of N-1-propylsulfamide.

[Properties of Compound (86)]
$^1$H-NMR(DMSO-d$_6$, δ ppm): 0.79(3H, t, J=7.4 Hz), 1.27 (3H, t, J=7.0 Hz), 1.43(2H, q, J=7.1 Hz), 2.82–2.87(2H, m), 3.99(2H, q, J=7.1 Hz), 5.49(2H, s), 6.48(1H, d, J=8.8 Hz), 6.81(1H, dd, J=8.8 and 2.4 Hz), 7.11(1H, d, J=2.5 Hz), 7.63(1H, d, J=8.5 Hz), 7.71(1H, brs), 7.77(1H, d, J=8.3 Hz), 8.06(1H, s), 11.56(1H, brs).
IR(Nujol): 1667 cm$^{-1}$.
MASS(FD): m/z 464 (M).
mp: 175.3–176.2° C.

EXAMPLE 87

<Synthesis of 6-((N-1-butylaminosulfonyl)carbamoyl)-1-(2-chloro-4-(ethyloxy)benzyl)-2-methylbenzimidazole (87)>

In the same manner as in Example 1, 0.200 g of the title compound were formed from 0.200 g of 6-carboxy-1-(2-chloro-4-(ethyloxy)benzyl)-2-methylbenzimidazole and 0.115 g of N-1-butylsulfamide.

[Properties of Compound (87)]
$^1$H-NMR(DMSO-$_6$, δ ppm): 0.77(3H, t, J=7.4 Hz), 1.20–1.30(5H, m), 1.37–1.44(2H, m), 2.48(3H, s), 2.88(2H, q, J=6.8 Hz), 3.99(2H, q, J=7.0 Hz), 5.49(2H, s), 6.48(1H, d, J=8.7 Hz), 6.80(1H, dd, J=8.7 and 2.5 Hz), 7.11(1H, d, J=2.5 Hz), 7.66–7.70(2H, m), 7.77(1H, dd, J=8.4 and 1.6 Hz), 8.07(1H, d, J=1.4 Hz), 11.56(1H, brs).
IR(Nujol): 1667 cm$^{-1}$.
mp: 180.0–181.3° C.

EXAMPLE 88

<Synthesis of 1-(2-chloro-4-(pentyloxy)benzyl)-6-((N-ethylaminosulfonyl)carbamoyl)-2-methylbenzimidazole (88)>

In the same manner as in Example 1, 0.188 g of the title compound were formed from 0.200 g of 6-carboxy-1-(2-chloro-4-(pentyloxy)benzyl)-2-methylbenzimidazole and 0.090 g of N-ethylsulfamide.

[Properties of Compound (88)]
$^1$H-NMR(DMSO-d$_6$, δ ppm): 0.86(3H, t, J=6.9 Hz), 1.02 (3H, t, J=7.1 Hz), 1.27–1.37(4H, m), 1.62–1.70(2H, m), 2.90–2.97(2H, m), 3.93(2H, t, J=6.6 Hz), 5.49(2H, s), 6.48 (1H, d, J=8.5 Hz), 6.81(1H, dd, J=8.6 and 2.0 Hz), 7.11(1H, d, J=2.5 Hz), 7.62–7.69(2H, m), 7.77(1H, d, J=8.6 Hz), 8.08(1H, s), 11.59(1H, brs).
IR(Nujol): 1667 cm$^{-1}$.
mp: 179.2–181.4° C.

EXAMPLE 89

<Synthesis of 1-(2-chloro-4-(pentyloxy)benzyl)-2-methyl-6-((N-1-propylaminosulfonyl)carbamoyl)benzimidazole (89)>

In the same manner as in Example 1, 0.142 g of the title compound were formed from 0.200 g of 6-carboxy-1-(2-chloro-4-(pentyloxy)benzyl)-2-methylbenzimidazole and 0.100 g of N-1-propylsulfamide.

[Properties of Compound (89)]
$^1$H-NMR(DMSO-d$_6$, δ ppm): 0.79(3H, t, J=7.4 Hz), 0.86 (3H, t, J=6.8 Hz), 1.25–1.38(4H, m), 1.39–1.47(2H, m), 1.62.–1.69(2H, m), 2.82–2.88(2H, m), 3.93(2H, t, J=6.5 Hz), 5.49(2H, s), 6.48(1H, d, J=8.7 Hz), 6.81(1H, dd, J=8.7 and 2.5 Hz), 7.11(1H, d, J=2.4 Hz), 7.64(1H, d, J=8.5 Hz), 7.68–7.72(1H, m), 7.77(1H, d, J=8.5 Hz), 8.07(1H, s), 11.57(1H, brs).
IR(Nujol): 1667 cm$^{-1}$.
MASS(FD): m/z 506 (M).
mp: 176.4–179.1° C.

EXAMPLE 90

<Synthesis of 6-((N-1-butylaminosulfonyl)carbamoyl)-1-(2-chloro-4-(pentyloxy)benzyl)-2-methylbenzimidazole (90)>

In the same manner as in Example 1, 0.14 g of the title compound were formed from 0.200 g of 6-carboxy-1-(2-chloro-4-(pentyloxy)benzyl)-2-methylbenzimidazole and 0.10 g of N-1-butylsulfamide.

[Properties of Compound (90)]
$^1$H-NMR(DMSO-d$_6$, δ ppm): 0.77(3H, t, J=7.4 Hz), 0.86 (3H, t, J=7.2 Hz), 1.19–1.43(8H, m), 1.63–1.69(2H, m), 2.48(3H, s), 2.88(2H, q, J=6.8 Hz), 3.93(2H, t, J=6.5 Hz), 5.49(2H, s), 6.47(1H, d, J=8.6 Hz), 6.80(1H, dd, J=8.8 and 2.5 Hz), 7.11(1H, d, J=2.6 Hz), 7.62–7.69(2H, m), 7.77(1H, dd, J=8.4 and 1.6 Hz), 8.07(1H, s), 11.56(1H, brs).
IR(Nujol): 1672 cm$^{-1}$.
mp: 173.5–175.2° C.

EXAMPLE 91

<Synthesis of 1-(2-chloro-4-(2-furyl)benzyl)-6-((N-ethylaminosulfonyl)carbamoyl)-2-methylbenzimidazole (91)>

In the same manner as in Example 1, 0.141 g of the title compound were formed from 0.200 g of 6-carboxy-1-(2-chloro-4-(2-furyl)benzyl)-2-methylbenzimidazole and 0.088 g of N-ethylsulfamide.

[Properties of Compound (91)]
$^1$H-NMR(DMSO-d$_6$, δ ppm): 1.01(3H, t, J=7.2 Hz), 2.89–2.95(2H, m), 5.59(2H, s), 6.56(1H, d, J=8.1 Hz), 6.59(1H, dd, J=3.4 and 1.9 Hz), 7.05(1H, d, J=3.4 Hz), 7.55(1H, dd, J=8.1 and 2.0 Hz), 7.64(1H, brs), 7.66(1H, d, J=8.4 Hz), 7.75(1H, d, J=1.8 Hz), 7.79(1H, dd, J=8.4 and 1.5 Hz), 7.87(1H, d, J=1.6 Hz), 8.09(1H, d, J=1.4 Hz), 11.59 (1H, brs).
IR(Nujol): 1667 cm$^{-1}$.
MASS(FD): m/z 472 (M).
mp: 190.5–192.2° C.

EXAMPLE 92

<Synthesis of 1-(2-chloro-4-(2-furyl)benzyl)-2-methyl-6-((N-1-propylaminosulfonyl)carbamoyl)benzimidazole (92)>

In the same manner as in Example 1, 0.105 g of the title compound were formed from 0.200 g of 6-carboxy-1-(2-chloro-4-(2-furyl)benzyl)-2-methylbenzimidazole and 0.098 g of N-1-propylsulfamide.

[Properties of Compound (92)]
$^1$H-NMR(DMSO-d$_6$, δ ppm): 0.77(3H t, J=7.4 Hz), 1.37–1.46(2H, m), 2.51(3H, s), 2.84(2H, q, J=6.4 Hz), 5.59(2H, s), 6.56(1H, d, J=8.2 Hz), 6.59(1H, dd, J=3.5 and 1.7 Hz), 7.05(1H, d, J=3.4 Hz), 7.54(1H, d, J=8.1 Hz), 7.66(1H, d, J=8.5 Hz), 7.68–7.71(1H, m), 7.76(1H, d, J=1.5 Hz), 7.78(1H, dd, J=8.3 and 1.5 Hz), 7.87(1H, d, J=1.5 Hz), 8.10(1H, s), 11.56(1H, brs).
IR(Nujol): 1656 cm$^{-1}$.
MASS(FD): m/z 486 (M).
mp: 177.8–180.2° C.

EXAMPLE 93

<Synthesis of 6-((N-1-butylaminosulfonyl)carbamoyl)-1-(2-chloro-4-(2-furyl)benzyl)-2-methylbenzimidazole (93)>

In the same manner as in Example 1, 0.23 g of the title compound were formed from 0.337 g of 6-carboxy-1-((2-chloro-4-(2-furyl)benzyl)-2-methylbenzimidazole and 0.228 g of N-1-butylsulfamide.

[Properties of Compound (93)]

$^1$H-NMR(DMSO-d$_6$, δ ppm): 0.74(3H, t, J=7.3 Hz), 1.21 (2H, m), 1.37(2H, m), 2.51(3H, s), 2.87(2H, m), 5.59(2H, s), 6.56(1H, d, J=8.1 Hz), 6.59(1H, m), 7.04(1H, d, J=3.3 Hz), 7.54(1H, d, J=8.2 Hz), 7.66(2H, m), 7.75(1H, s), 7.78(1H, d, J=8.4 Hz), 7.87(1H, s), 8.09(1H, s), 11.58(1H, brs).

IR(Nujol): 1667 cm$^{-1}$.

mp: 205.0–205.3° C.

EXAMPLE 94

<Synthesis of 6-((benzylaminosulfonyl)carbamoyl)-1-(2-chloro-4-(2-furyl)benzyl)-2-methylbenzimidazole (94)>

In the same manner as in Example 1, 0.23 g of the title compound were formed from 0.337 g of 6-carboxy-1-((2-chloro-4-(2-furyl)benzyl)-2-methylbenzimidazole and 0.279 g of N-benzylsulfamide.

[Properties of Compound (94)]

$^1$H-NMR(DMSO-d$_6$, δ ppm): 2.51(3H, s), 4.14(2H, d, J=5.7 Hz), 5.58(2H, s), 6.53(1H, d, J=8.2 Hz), 6.59(1H, m), 7.06(2H, m), 7.15(2H, t, J=7.5 Hz), 7.27(2H, d, J=7.4 Hz), 7.57(1H, dd, J=8.1 and 1.4 Hz), 7.64(1H, d, J=8.5 Hz), 7.72(1H, dd, J=8.6 and 1.4 Hz), 7.76(1H, d, J=1.1 Hz), 7.89(1H, d, J=1.5 Hz), 7.98(1H, s), 8.31(1H, m), 11.59(1H, brs).

IR(Nujol): 1656 cm$^{-1}$.

mp: 187.3–187.5° C.

EXAMPLE 95

<Synthesis of 1-(2-chloro-4-ethylbenzyl)-2-methyl-6-((N-1-propylaminosulfonyl)carbamoyl)benzimidazole (95)>

In the same manner as in Example 1, 0.045 g of the title compound were formed from 0.150 g of 6-carboxy-1-(2-chloro-4-ethylbenzyl)-2-methylbenzimidazole and 0.082 g of N-1-propylsulfamide.

[Properties of Compound (95)]

$^1$H-NMR(DMSO-d$_6$, δ ppm): 0.79(3H, t, J=7.4 Hz), 1.13 (3H, t, J=7.3 Hz), 1.39–1.47(2H, m), 2.54–2.59(2H, m), 2.82–2.87(2H, m), 5.54(2H, s), 6.39(1H, d, J=8.1 Hz), 7.06(1H, d, J=8.5 Hz), 7.40(1H, s), 7.65(1H, d, J=8.5 Hz), 7.67–7.71(1H, m), 7.78(1H, d, J=8.8 Hz), 8.07(1H, s), 11.55(1H, brs).

mp: 174.3–175.7° C.

EXAMPLE 96

<Synthesis of 6-((N-1-butylaminosulfonyl)carbamoyl)-1-(2-chloro-4-ethylbenzyl)-2-methylbenzimidazole (96)>

In the same manner as in Example 1, 0.076 g of the title compound were formed from 0.150 g of 6-carboxy-1-(2-chloro-4-ethylbenzyl)-2-methylbenzimidazole and 0.090 g of N-1-butylsulfamide.

[Properties of Compound (96)]

$^1$H-NMR(DMSO-d$_6$, δ ppm): 0.77(3H, t, J=7.3 Hz), 1.13 (3H, t, J=7.4 Hz), 1.19–1.27(2H, m), 1.36–1.43(2H, m), 2.54–2.59(2H, m), 2.88(2H, q, J=7.4 Hz), 5.53(2H, s), 6.38(1H, d, J=8.3 Hz), 7.06(1H, d, J=7.5 Hz), 7.40(1H, s), 7.63–7.68(2H, m), 7.77(1H, d, J=8.5 Hz), 8.06(1H, s), 11.55(1H, brs).

IR(Nujol): 1667 cm$^{-1}$.

mp: 169.3–171.0° C.

EXAMPLE 97

<Synthesis of 6-((N-1-butylaminosulfonyl)carbamoyl)-1-(2-chloro-4-n-hexylbenzyl)-2-methylbenzimidazole (97)>

In the same manner as in Example 1, 0.092 g of the title compound were formed from 0.150 g of 6-carboxy-1-(2-chloro-4-hexylbenzyl)-2-methylbenzimidazole and 0.077 g of N-1-butylsulfamide.

[Properties of Compound (97)]

$^1$H-NMR(DMSO-d$_6$, δ ppm): 0.76(3H, t, J=7.4 Hz), 0.75–0.84(3H, m), 1.20–1.27(8H, m), 1.36–1.43(2H, m), 1.47–1.54(2H, m), 2.50–2.55(2H, m), 2.86–2.90(2H, m), 5.53(2H, s), 6.38(1H, d, J=8.0 Hz), 7.04(1H, d, J=8.1 Hz), 7.38(1H, s), 7.64–7.71(2H, m), 7.78(1H, dd, J=8.4 and 2.0 Hz), 8.08(1H, s), 11.55(1H, brs).

IR(Nujol): 1667 cm$^{-1}$.

mp: 172.1–173.4° C.

TEST EXAMPLE

<Activity of Decreasing Blood Sugar Using db/db Mice>

TEST COMPOUNDS 1-(2-Chloro-4-(n-pentyloxy)benzyl)-2-methyl-6-((4-methylbenzene)sulfonylcarbamoyl)benzimidazole—Compound(15)

6-((N-1-butylaminosulfonyl)carbamoyl)-1-(2-chloro-4-phenylbenzyl)-2-methylbenzimidazole—Compound(76)

Animal Used

Five-week-old female mice [C57BL/KsJ-dbm db+/db+, C57BL/KsJ-dbm +m/+m (Jackson Laboratory)] were purchased, and were kept for 2 to 3 weeks. Then, these mice were used in the test.

Preparation of an Agent

A test compound was mixed with a powdered chow (CE-2, made by Nippon Clea) using a mortar. The mixing ratio was 0.01%. The mixed chow was changed twice a week for each group. The feed amount and the remaining amount were recorded, and the intake was calculated from the difference therebetween.

Test Schedule

The female db/db mice were grouped according to the body weight, the plasma glucose, and the plasma triglyceride concentrations. Then, the mixture containing the test compound was administered to the mice for 14 days (from 8 to 10 weeks old). In the morning on day 7 and day 14, blood was collected from the orbital venous plexus using heparinized glass capillary tubes (Chase Heparinized Capillary Tubes), and a plasma fraction was obtained through centrifugal separation. Plasma glucose, triglyceride, and insulin concentrations were measured on day 0 and day 14. Plasma glucose and triglyceride concentrations were measured on day 7. The body weight was measured on day 0, day 7, and day 14. After the final collection of the blood, the mice were killed using CO$_2$ gas.

Measurement Method

The plasma glucose was measured by a glucose oxidase method (Glucose CII-Test Wako made by Wako Pure Chemical Industries, Ltd.) using from 10 to 15 μl of plasma. The plasma triglyceride concentration was measured by a GPO-p-chlorophenol method (Triglyceride G-Test Wako made by Wako Pure Chemical Industries, Ltd.) or a GPO-DAOS method (Triglyceride E-Test Wako) using from 10 to 15 μl of plasma. The above-mentioned measurements were conducted immediately after the blood collection. The plasma insulin concentration was measured by radioimmunoassay method (Phadesef Insulin RIA Kit made by Cabi Pharmacia) using 20 μl of plasma (which can be stored at −20° C.).

Results

The difference in the plasma glucose and the plasma triglyceride concentrations between the db/db mouse and the +/+ mouse was defined as 100%, and the rate (%) of decrease in the plasma glucose and the plasma triglyceride concentrations of the group to which the test compound was administered was calculated. The results were as follows: when 1 mg/kg of Compound (15) was administered, the rate of decrease in the plasma glucose was 79% and the rate of decrease in the plasma triglyceride was 69%; when 1 mg/kg of Compound (76) was administered, the rate of decrease in the plasma glucose was 71% and the rate of decrease in the plasma triglyceride was 98%.

INDUSTRIAL APPLICABILITY

Herein provided are novel benzimidazole derivatives and their pharmaceutically acceptable salts. These compounds and their salts, which are acceptable as medicine, have blood sugar level-depressing activity or PDE5-inhibiting activity, and are useful as therapeutic agents for impaired glucose tolerance, diabetes (type II diabetes), diabetic complications (e.g. diabetic gangrene, diabetic arthropathy, diabetic osteopenia, diabetic glomerulosclerosis, diabetic nephropathy, diabetic dermopathy, diabetic neuropathy, diabetic cataract, diabetic retinopathy, etc.), insulin-resistant syndrome (e.g., insulin receptor disorders, Rabson-Mendenhall syndrome, leprechaunism, Kobberling-Dunnigan syndrome, Seip syndrome, Lawrence syndrome, Cushing syndrome, acromegaly, etc.), polycystic ovary syndrome. hyperlipidemia, atherosclerosis, cardiovascular disorders (e.g., stenocardia, cardiac failure, etc.), hyperglycemia (e.g., abnormal saccharometabolism such as feeding disorders, etc.), pancreatitis, osteoporosis, hyperuricemia, hypertension, inflammatory bowel disease, skin disease accompanying abnormal differentation of epidermal cells, stenocardia, pulmonary hypertension, congestive heart failure, glomerulopathy (e.g., diabetic glomerulosclerosis, etc.), tubulointerstitial disorders (e.g., renopathy induced by FK506, cyclosporin, etc.), renal failure, atherosclerosis, angiostenosis (e.g., angiostenosis after percutaneous arterioplasty), distal angiopathy, cerebral apoplexy, chronic reversible obstructions (e.g., bronchitis, asthma (chronic asthma, allergic asthma), etc.), autoimmune disease, allergic rhinitis, urticaria, glaucoma, diseases characterized by enteromotility disorders (e.g., hypersensitive enteropathy syndrome, etc.), impotence (e.g., organic impotence, psychic impotence, etc.), nephritis, cachexia (e.g. progressive weight reduction due to lipolysis, myodegeneration, anaemia, edema, anorexia, and such in chronic diseases such as cancer, tuberculosis, endocrine diseases, and AIDS), pancreatitis, or post-PTCA restenosis. In addition, they, in combination with a retinoid, are effective for treating diseases associated with cell proliferative disorders including cancer, restenosis, and atherosclerosis.

What is claimed is:
1. A benzimidazole derivative of the following formula (I), or its salt:

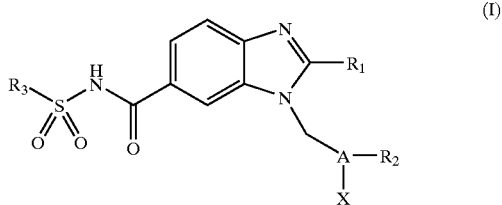

wherein
R$_1$ represents a lower alkyl group or a lower alkyloxy-lower alkyl group; R$_2$ represents an ethyl group, an n-butyl group, an n-pentyl group, an n-heptyl group, a methoxy group, an ethoxy group, and n-propyloxy group, an n-pentyloxy group, an n-hexyloxy group, an n-octyloxy group, a lower alkyloxy-lower alkyloxy group, a (cyclopentylmethyl)oxy group, an alkynyl group having 3 to 8 carbon atoms, a methylthio group, a lower alkanoylamino group, an N-substituted lower alkylamino group, or a morpholino group; R$_3$ represents a lower alkyl group, a lower alkenyl group, an aryl group, a lower alkylaryl group, an aryl-lower alkenyl group, or a halothienyl group;

A represents a benzene ring; and

X represents a halogen atom.

2. The benzimidazole derivative or its salt of claim 1, wherein X represents a chlorine atom.

3. The benzimidazole derivative or its salt of claim 2, wherein an aryl moiety of an aryl group, an aryl-lower alkyl group, an aryloxy-lower alkyl group, an aryl-lower alkyloxy group, and and an aryl-lower alkylamino group is a phenyl group.

4. The benzimidazole derivative or its salt of claim 3, wherein R$_1$ is a methyl group; and R$_3$ is a butyl group, a pentyl group, a pentenyl group, a phenyl group, a methylphenyl group, a phenylethenyl group, or a chlorothienyl group.

5. The benzimidazole derivative or its salt of claim 1, wherein the benzimidazole derivative or its salt is selected from the group consisting of 1-(2-chloro-4-(n-octyloxy)benzyl)-2-methyl-6-(1-pentane-sulfonylcarbamoyl)benzimidazole,
1-(2-chloro-4-(n-octyloxy)benzyl)-2-methyl-6-((4-methylbenzene)sulfonylcarbamoyl)benzimidazole,
1-(2-chloro-4-(n-hexyloxy)benzyl)-2-methyl-6-(1-pentane-sulfonylcarbamoyl)benzimidazole,
1-(2-chloro-4-(n-pentyloxy)benzyl)-2-methyl-6-((4-pentane-sulfonylcarbamoyl)benzimidazole,
1-(2-chloro-4-(n-pentyloxy)benzyl)-2-methyl-6-((1-methylbenzene)sulfonylcarbamoyl)benzimidazole;
1-(2-chloro-4-(n-propyloxy)benzyl)-2-methyl-6-(1-pentane-sulfonylcarbamoyl)benzimidazole,
1-(2-chloro-4-(n-propyloxy)benzyl)-2-methyl-6-((4-methylbenzene)sulfonylcarbamoyl)benzimidazole,
1-(2-chloro-4-(methyloxy)benzyl)-2-methyl-6-(1-pentane-sulfonylcarbamoyl)benzimidazole,
1-(2-chloro-4-(methyloxy)benzyl)-2-methyl-6-((4-methylbenzene)sulfonylcarbamoyl)benzimidazole,
1-(2-chloro-4-(2-methyloxyethyl)oxy)benzyl)-2-methyl-6-(1-pentanesulfonylcarbamoyl)benzimidazole,
1-(2-chloro-4-((2-methyloxyethyl)oxy)benzyl)-2-methyl-6-((4-methylbenzene)sulfonylcarbamoyl)benzimidazole, 1-(2-chloro-4-(cyclopentylmethyloxy)benzyl)-2-methyl-6-(1-pentanesulfonylcarbamoyl)benzimidazole,
1-(2-chloro-4-(cyclopentylmethyloxy)benzyl)-2-methyl-6-((4-methylbenzene)sulfonylcarbamoyl)benzimidazole,
1-(2-chloro-4-(cyclopentylmethyloxy)benzyl)-2-methyl-6-((E)-1-pent-1-enesulfonylcarbamoyl)benzimidazole,
1-(2-chloro-4-(1-pentyn-1-yl)benzyl)-2-methyl-6-(1-pentane-sulfonylcarbamoyl)benzimidazole,
1-(2-chloro-4-(1-pentyn-1-yl)benzyl)-2-methyl-6-((4-methylbenzene)sulfonylcarbamoyl)benzimidazole,
1-(2-chloro-4-(1-hexyn-1-yl)benzyl)-2-methyl-6-(1-pentane-sulfonylcarbamoyl)benzimidazole,
1-(2-chloro-4-(1-hexyn-1-yl)benzyl)-2-methyl-6-(4-methylbenzene)sulfonylcarbamoyl)benzimidazole,
1-(2-chloro-4-(1-heptyn-1-yl)benzyl)-2-methyl-6-(1-pentane-sulfonylcarbamoyl)benzimidazole,
1-(2-chloro-4-(1-heptyn-1-yl)benzyl)-2-methyl-6-(4-methylbenzene)sulfonylcarbamoyl)benzimidazole,
1-(2-chloro-4-ethylbenzyl)-2-methyl-6-(1-pentanesulfonyl-carbamoyl)benzimidazole,
1-(2-chloro-4-ethylbenzyl)-2-methyl-6-((4-methylbenzene)-sulfonylcarbamoyl)benzimidazole,
1-(4-n-butyl-2-chlorobenzyl)-2-methyl-6-(1-pentanesulfonyl-carbamoyl)benzimidazole,
1-(4-n-butyl-2-chlorobenzyl)-2-methyl-6-((4-methylbenzene)-sulfonylcarbamoyl)benzimidazole,
1-(2-chloro-4-(1-pentyl)benzyl)-2-methyl-6-(1-pentane-sulfonylcarbamoyl)benzimidazole,
1-(2-chloro-4-(1-pentyl)benzyl)-2-methyl-6-((4-methylbenzene)sulfonylcarbamoyl)benzimidazole,
1-(2-chloro-4-(1-heptyl)benzyl)-2-methyl-6-(1-pentane-sulfonylcarbamoyl)benzimidazole,
1-(2-chloro-4-(1-heptyl)benzyl)-2-methyl-6-((4-methylbenzene)sulfonylcarbamoyl)benzimidazole,
1-(2-chloro-4-(N-methyl-N-(1-pentyl)amino)benzyl)-2-methyl-6-(1-pentanesulfonylcarbamoyl)benzimidazole,
1-(2-chloro-4-(N-methyl-N-(1-pentyl)amino)benzyl)-2-methyl-6-((4-methylbenzene)sulfonylcarbamoyl)benzimidazole,
1-(4-(N-1-butyrylamino)-2-chlorobenzyl)-2-methyl-6-(1-pentanesulfonylcarbamoyl)benzimidazole,
1-(4-(N-1-butyrylamino)-2-chlorobenzyl)-2-methyl-6-((4-methylbenzene)sulfonylcarbamoyl)benzimidazole,
1-(2-chloro-4-morpholinobenzyl)-2-methyl-6-((4-methylbenzene)sulfonylcarbamoyl)benzimidazole,
1-(2-chloro-4-morpholinobenzyl)-2-methyl-6-(1-pentane-sulfonylcarbamoyl)benzimidazole,
1-(2-chloro-4-(methylthio)benzyl)-2-methyl-6-(1-pentanesulfonylcarbamoyl)benzimidazole, and
1-(2-chloro-4-(methylthio)benzyl)-2-methyl-6-((4-methylbenzene)sulfonylcarbamoyl)benzimidazole.

6. A pharmaceutical composition comprising, as an active ingredient, the benzimidazole derivative of any one of claims 1 to 5 or a pharmaceutically acceptable salt thereof.

\* \* \* \* \*